US012679833B2

(12) United States Patent
Luckhurst et al.

(10) Patent No.: US 12,679,833 B2
(45) Date of Patent: Jul. 14, 2026

(54) N-CYANOPYRROLIDINES WITH ACTIVITY AS USP30 INHIBITORS

(71) Applicant: MISSION THERAPEUTICS LIMITED, Cambridge (GB)

(72) Inventors: Christopher Andrew Luckhurst, Cambridge (GB); Mark Ian Kemp, Cambridge (GB); Paul William Thompson, Cambridge (GB)

(73) Assignee: Mission Therapeutics Limited, Cambridge (GB)

( * ) Notice: Subject to any disclaimer, the term of this patent is extended or adjusted under 35 U.S.C. 154(b) by 677 days.

(21) Appl. No.: 18/007,641

(22) PCT Filed: Jun. 3, 2021

(86) PCT No.: PCT/EP2021/064897

§ 371 (c)(1),
(2) Date: Dec. 1, 2022

(87) PCT Pub. No.: WO2021/245186

PCT Pub. Date: Dec. 9, 2021

(65) Prior Publication Data

US 2023/0303547 A1 Sep. 28, 2023

(30) Foreign Application Priority Data

Jun. 4, 2020 (GB) ..................................... 2008401
Oct. 21, 2020 (GB) ..................................... 2016689
Feb. 11, 2021 (GB) ..................................... 2101935

(51) Int. Cl.

| | |
|---|---|
| ***C07D 413/12*** | (2006.01) |
| ***A61P 13/12*** | (2006.01) |
| ***A61P 19/04*** | (2006.01) |
| *A61K 31/422* | (2006.01) |
| *A61P 11/00* | (2006.01) |
| *A61P 25/28* | (2006.01) |
| *A61P 35/00* | (2006.01) |
| *A61P 43/00* | (2006.01) |

(52) U.S. Cl.

CPC ............ *C07D 413/12* (2013.01); *A61P 13/12* (2018.01); *A61P 19/04* (2018.01)

(58) Field of Classification Search

CPC .................................................... C07D 413/12

See application file for complete search history.

(56) References Cited

U.S. PATENT DOCUMENTS

2004/0073029 A1 4/2004 Pruitt et al.
2008/0300268 A1 12/2008 Singh et al.
2009/0326020 A1 12/2009 Miller et al.
2012/0077806 A1 3/2012 Donato et al.

FOREIGN PATENT DOCUMENTS

WO 95/08534 A1 3/1995
WO 0177073 A1 10/2001
WO 2004022536 A1 3/2004
WO 2006067165 A2 6/2006
WO 2007119214 A2 10/2007
WO 2009026197 A1 2/2009
WO 2009129365 A1 10/2009

(Continued)

OTHER PUBLICATIONS

Chevalier et al, "Ureteral obstruction as a model of renal interstitial fibrosis and obstructive nephropathy," Apr. 1, 2009, Kidney Int 75(11): 1145-1152.

(Continued)

*Primary Examiner* — Bruck Kifle
*Assistant Examiner* — Kevin S Martin

(57) ABSTRACT

The present invention relates to a class of N-cyanopyrrolidines with activity as inhibitors of the deubiquitylating enzyme USP30, having utility in a variety of therapeutic areas, including conditions involving mitochondrial dysfunction, cancer and fibrosis: (formulae (I)(i) and (I)(ii)).

(I)(i)

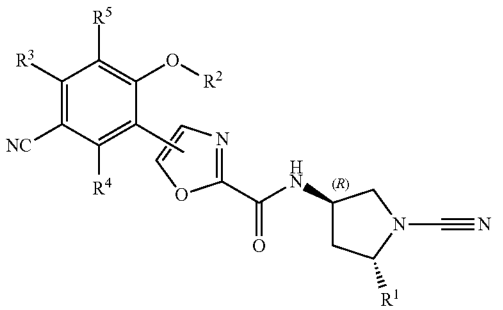

(I)(ii)

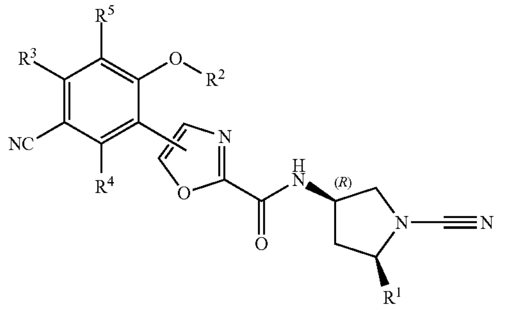

20 Claims, No Drawings

(56) References Cited

FOREIGN PATENT DOCUMENTS

| | | | | |
|---|---|---|---|---|
| WO | 2009129370 | A1 | 10/2009 | |
| WO | 2009129371 | A1 | 10/2009 | |
| WO | 2010051188 | A1 | 5/2010 | |
| WO | 2010111059 | A1 | 9/2010 | |
| WO | 2012040527 | A2 | 3/2012 | |
| WO | 2012170290 | A1 | 12/2012 | |
| WO | 2013030218 | A1 | 3/2013 | |
| WO | 2013106643 | A2 | 7/2013 | |
| WO | 2014152588 | A1 | 9/2014 | |
| WO | 2015017502 | A1 | 2/2015 | |
| WO | 2015179190 | A1 | 11/2015 | |
| WO | 2015183987 | A1 | 12/2015 | |
| WO | 2016019237 | A1 | 2/2016 | |
| WO | 2016021629 | A1 | 2/2016 | |
| WO | 2016046530 | A1 | 3/2016 | |
| WO | 2016156816 | A1 | 10/2016 | |
| WO | 2017/009650 | A1 | 1/2017 | |
| WO | 2017/093718 | A1 | 6/2017 | |
| WO | 2017/109488 | A1 | 6/2017 | |
| WO | 2017103614 | A1 | 6/2017 | |
| WO | 2017/141036 | A1 | 8/2017 | |
| WO | 2017/149313 | A1 | 9/2017 | |
| WO | 2017/158381 | A1 | 9/2017 | |
| WO | 2017/158388 | A1 | 9/2017 | |
| WO | 2017/163078 | A1 | 9/2017 | |
| WO | 2018060689 | A1 | 4/2018 | |
| WO | 2018060691 | A1 | 4/2018 | |
| WO | 2018060742 | A1 | 4/2018 | |
| WO | 2018065768 | A1 | 4/2018 | |
| WO | 2018213150 | A1 | 11/2018 | |
| WO | 2018220355 | A1 | 12/2018 | |
| WO | 2018234775 | A1 | 12/2018 | |
| WO | 2019071073 | A1 | 4/2019 | |
| WO | 2019171042 | A1 | 9/2019 | |
| WO | 2019222468 | A1 | 11/2019 | |
| WO | 2020036940 | A1 | 2/2020 | |
| WO | 2020072964 | A1 | 4/2020 | |
| WO | 2020212351 | A1 | 10/2020 | |
| WO | WO-2020212350 | A1 * | 10/2020 | ........... C07D 413/12 |
| WO | 2021043870 | A1 | 3/2021 | |
| WO | 2021204856 | A1 | 10/2021 | |
| WO | 2021239863 | A1 | 12/2021 | |
| WO | 2021249909 | A1 | 12/2021 | |

OTHER PUBLICATIONS

Lu et al., “C57BL/6 and 129/Sv mice: genetic difference to renal ischemia-reperfusion,” 2012. J Nephrol. 25 (5): 738-45.
Harrigan J.A. et al, “Deubiquitylating enzymes and drug discovery: emerging opportunities.”, Nat Rev Drug Discov. Jan. 2018;17(1):57-78.
Morgan et al, “A Solid-Phase Route to N-Cyanoamides,” Organic Letters, 2002, 4(4), 597-598.
Kemp et al, “Recent Advances in the Discovery of Deubiquitinating Enzyme Inhibitors”, Progress in Medicinal Chemistry, 2016, 55, 149-192.
Jacq et al, “Deubiquitylating Enzymes and DNA Damage Response Pathways,” Cell Biochem Biophys, May 28, 2013, 67:25-43.
Rusilowicz-Jones, “USP30 sets a trigger threshold for PINK1-PARKIN amplification of mitochondrial ubiquitylation.”, Life Science Alliance Jul. 2020, 3 (8) e202000768; DOI: 10.26508/lsa.202000768.
Liu et al., “Deubiquitinase Activity Profiling Identifies UCHL1 as a Candidate Oncoprotein That Promotes TGFb-Induced Breast Cancer Metastasis”, Clin Cancer Res 2020;26:1460-1473.
Bashore et al, “Cyanopyrrolidine Inhibitors of Ubiquitin Specific Protease 7 Mediate Desulfhydration of the Active-Site Cysteine”, ACS Chem. Biol. 2020, 15, 6, 1392-1400.
Bashore et al, “Cyanopyrrolidine Inhibitors of Ubiquitin Specific Protease 7 Mediate Desulfhydration of the Active-Site Cysteine”, ACS Chem. Biol. 2020, 15, 6, 1392-1400. (Supporting Information).
Yue et al, “A small natural molecule promotes mitochondrial fusion through inhibition of the deubiquitinase USP30”, Cell Research, 2014, 24, 482-496.
Tsefou et al, “Investigation of USP30 inhibition to enhance Parkin-mediated mitophagy: tools and approaches,” bioRxiv, Feb. 2, 2021, https://doi.org/10.1101/2021.02.02.429344.
Kellum et al, “Targeting acute kidney injury in COVID-19,” Nephrol Dial Transplant (2020) 35: 1652-1662.
Mora et al., “Mitochondria in the spotlight of aging and idiopathic pulmonary fibrosis,” J Clin Invest, Feb. 1, 2017, 127(2), pp. 405-414.
The International Search Report and Written Opinion, mailed on Aug. 20, 2021, in the corresponding PCT Appl. No. PCT/EP2021/064897.
Falgueyret et al., “Novel, Nonpeptidic Cyanamides as Potent and Reversible Inhibitors of Human Cathepsins K and L,” J. Med. Chem. 2001, 44, 94-104.
Laine et al., “Discovery of Novel Cyanamide-Based Inhibitors of Cathepsin C,” ACS Med. Chem. Lett. 2011, 2, 142-147.
Clague et al., “Deubiquitylases from genes to organism”, Physiol. Rev. 93:1289-1315, 2013.
Rydzewski et al, “Peptidic 1-Cyanopyrrolidines: Synthesis and SAR of a Series of Potent, Selective Cathepsin Inhibitors”, Bioorganic & Medicinal Chemistry 10 (2002) 3277-3284.
Deaton et al, “Novel and potent cyclic cyanamide-based cathepsin K inhibitors”, Bioorganic & Medicinal Chemistry Letters 15 (2005) 1815-1819.
Oballa et al, “A generally applicable method for assessing the electrophilicity and reactivity of diverse nitrile-containing compounds”, Bioorganic & Medicinal Chemistry Letters 17 (2007) 998-1002.
Zapf et al, “Covalent Inhibitors of Interleukin-2 Inducible T Cell Kinase (Itk) with Nanomolar Potency in a Whole-Blood Assay”, J. Med. Chem. 2012, 55, 10047-10063.
Nakamura et al, “Regulation of Mitochondrial Morphology by USP30, a Deubiquitinating Enzyme Present in the Mitochondrial Outer Membrane”, Molecular Biology of the Cell, vol. 19, 1903-1911, May 2008.
Bingol et al, “The mitochondrial deubiquitinase USP30 opposes parkin-mediated mitophagy”, Nature vol. 510, 370-375, 2014.
Liang et al, “USP30 deubiquitylates mitochondrial Parkin substrates and restricts apoptotic cell death”, EMBO Reports, 1-10, 2015; DOI 10.15252/embr.201439820.
Bedford et al., “Ubiquitin-like protein conjugation and the ubiquitin-proteasome system as drug targets,” Nat Rev Drug Discov. Jan. 2011;10(1):29-46.
Wynn, Thomas A., “Fibrotic disease and the TH1/TH2 paradigm”, Nat Rev Immunol. Aug. 2004 ; 4(8): 583-594.
Ward et al., “Quantitative Chemical Proteomic Profiling of Ubiquitin Specific Proteases in Intact Cancer Cells,” ACS Chem. Biol. 2016, 11, 3268-3272.
Cai Yu et al, “Smurf2, an E3 ubiquitin ligase, interacts with PDE4B and attenuates liver fibrosis through miR-132 mediated CTGF inhibition”, Biochimica et Biophysica Acta. Molecular Cell Research, vol. 1865, No. 2, Oct. 31, 2017, pp. 297-308.
Krabill et al, “Biochemical and cellular characterization of a cyanopyrrolidine covalent Ubiquitin C-terminal hydrolase L1 inhibitor”, ChemBioChem, Aug. 2019, 21(5).
Kurita Y., et al., “Pirfenidone inhibits myofibroblast differentiation and lung fibrosis development during insufficient mitophagy”, Respiratory Research (2017) 18:114.
Williams J.A. et.al. “Targeting Pink1-Parkin-Mediated Mitophagy for Treating Liver Injury”, Pharmacol Res. Dec. 2015, 102: 264-269.
Williams J.A. et.al. “A Mechanistic Review of Mitophagy and Its Role in Protection against Alcoholic Liver Disease”, Biomolecules 2015, 5, 2619-2642.
Williams J.A. et.al. “Parkin regulates mitophagy and mitochondrial function to protect against alcohol-induced liver injury and steatosis in mice”, Am J Physiol Gastrointest Liver Physiol 309: G324-G340, 2015.

(56) References Cited

OTHER PUBLICATIONS

Larson-Casey et al., "Macrophage Akt1 Kinase-Mediated Mitophagy Modulates Apoptosis Resistance and Pulmonary Fibrosis," 2016, Immunity 44, 582-596.
Tang et al., "Mitophagy: Basic Mechanism and Potential Role in Kidney Diseases," Kidney Diseases 2015, 1, 71-79.
Kluge, "Novel highly selective inhibitors of ubiquitin specific protease 30 (USP30) accelerate mitophagy", Bioorganic & Medicinal Chemistry Letters, 2018, 28 2655-2659.
Thompson, www.Mednous.com, "Mitochondrial-quality-control-as-potential-therapy," Mar. 2018.
Silverman, R. "The Organic Chemistry of Drug Design and Drug Action", 2004, NY Elsevier, pp. 29-32.
Meanwell, N.,"Synopsis of Some Recent Tactical Application of Bioisosteres in Drug Design," J.Med.Chem., 54, 2011, pp. 2529-2591.
Phu et al, "Dynamic Regulation of Mitochondrial Import by the Ubiquitin System," 2020, Molecular Cell 77, 1107-1123.
Rusilowicz-Jones, "A novel USP30 inhibitor recapitulates genetic loss of USP30 and sets the trigger for PINK1-Parkin amplification of mitochondrial ubiquitylation," 2020, bioRxiv 2020.04.16.
Gersch et al, "Mechanism and regulation of the Lys6-selective deubiquitinase USP30," 2017, Nat Struct Mol Biol 24(11): 920-930.
Cunningham et al, "USP30 and parkin homeostatically regulate atypical ubiquitin chains on mitochondria," 2015, Nat Cell Biol 17(2): 160-169.
Jacoupy et al, "The PINK1 kinase-driven ubiquitin ligase Parkin promotes mitochondrial protein import through the presequence pathway in living cells," 2019, Sci Rep 9(1): 11829.
Riccio et al, "Deubiquitinating enzyme USP30 maintains basal peroxisome abundance by regulating pexophagy," 2019, J Cell Biol 218(3): 798-807.
Luciani et al,"Impaired mitophagy links mitochondrial disease to epithelial stress in methylmalonyl-CoA mutase deficiency," 2020, Nat. Commun. 11, 970.
Mehta et al,International Society of Nephrology's 0by25 initiative for acute kidney injury (zero preventable deaths by 2025): a human rights case for nephrology, 2015, Lancet 385(9987): 2616-2643.
Chawla et al, "Acute kidney disease and renal recovery: consensus report of the Acute Disease Quality Initiative (ADQI) 16 Workgroup," Apr. 2017, Nat Rev Nephrol 13(4): 241-257.
McWilliams et al, "Basal Mitophagy Occurs Independently of PINK1 in Mouse Tissues of High Metabolic Demand," Feb. 6, 2018, Cell Metab 27(2): 439-449 e435.
Emma et al, "Mitochondrial dysfunction in inherited renal disease and acute kidney injury," May 2016, Nat Rev Nephrol 12(5): 267-280.
Eirin et al, "The Emerging Role of Mitochondrial Targeting in Kidney Disease," Aug. 12, 2017, Handb Exp Pharmacol 240: 229-250.
Kawakami et al, "Deficient Autophagy Results in Mitochondrial Dysfunction and FSGS," 2015, J Am Soc Nephrol 26(5): 1040-1052.
Connor et al, "Mutations in mitochondrial DNA causing tubulointerstitial kidney disease," Mar. 7, 2017, PLoS Genet 13(3): e1006620.
Tang et al, "PINK1-PRKN/PARK2 pathway of mitophagy is activated to protect against renal ischemia-reperfusion injury," 2018, Autophagy 14(5): 880-897.
Wang et al, "PINK1/Parkin-mediated mitophagy is activated in cisplatin nephrotoxicity to protect against kidney injury," 2018, Cell Death Dis 9(11): 1113.
Kobayashi et al, "Involvement of PARK2-Mediated Mitophagy in Idiopathic Pulmonary Fibrosis Pathogenesis," Jun. 2016, J Immunol, 197:504-516.
Araya et al, "PRKN-regulated mitophagy and cellular senescence during COPD pathogenesis," 2019, Autophagy 15(3): 510-526.
Nishida et al, "Spontaneous onset of nonalcoholic steatohepatitis and hepatocellular carcinoma in a mouse model of metabolic syndrome," 2013, Lab Invest; Feb. 93(2):230-41.
Karuppagouner et al, "The c-Abl inhibitor, Nilotinib, protects dopaminergic neurons in a preclinical animal model of Parkinson's disease," Sci Rep. May 2, 2014;4:4874.
Kruse et al, "Mice with Mitochondrial Complex I Deficiency Develop a Fatal Encephalomyopathy," Apr. 2008, Cell Metab. Apr;7(4):312-20.
Kobilo et al, "AMPK agonist AICAR improves cognition and motor coordination in young and aged mice," 2014, Learn Mem. Jan. 17;21(2):119-26.
Creed et al,"Basal and Evoked Neurotransmitter Levels in Parkin, DJ-1, PINK1 and LRRK2 Knockout Rat Striatum," Neuroscience. Jun. 15, 2019;409:169-179.
Van Skike et al, "mTOR drives cerebrovascular, synaptic, and cognitive dysfunction in normative aging," Jun. 18, 2019, Aging Cell. 19; e13057.

* cited by examiner

N-CYANOPYRROLIDINES WITH ACTIVITY AS USP30 INHIBITORS

CROSS-REFERENCE TO RELATED APPLICATIONS

This application is a National Stage Application of PCT/EP2021/064897 filed Jun. 3, 2021, which claims priority from UK Patent Applications GB 2008401.8 filed on Jun. 4, 2020, GB 2016689.8 filed on Oct. 21, 2020 and GB 2101935.1 filed on Feb. 21, 2021. The priority of said PCT and UK Patent Applications are claimed. Each of the prior mentioned applications is hereby incorporated by reference herein in its entirety.

FIELD OF THE INVENTION

The present invention relates to a class of N-cyanopyrrolidines with activity as inhibitors of the deubiquitylating enzyme ubiquitin C-terminal hydrolase 30, also known as ubiquitin specific peptidase 30 (USP30), uses thereof, processes for the preparation thereof and composition containing said inhibitors. These inhibitors have utility in a variety of therapeutic areas, including conditions involving mitochondrial dysfunction, cancer and fibrosis.

All documents cited or relied upon below are expressly incorporated herein by reference.

BACKGROUND OF THE INVENTION

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein by deubiquitylating enzymes (DUBs), of which there are approximately 100 DUBs in human cells, divided into sub-families based on sequence homology. The USP family are characterised by their common Cys and His boxes which contain Cys and His residues critical for their DUB activities. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis.

Ubiquitin is a master regulator of mitochondrial dynamics. Mitochondria are dynamic organelles whose biogenesis, fusion and fission events are regulated by the post-translational regulation via ubiquitylation of many key factors such as mitofusins. In humans, USP30 is a 517 amino acid protein which is found in the mitochondrial outer membrane (Nakamura et al, 2008, Mol Biol 19:1903-11). It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy (Bingol et al, 2015, Nature 510:370-5; Gersch et al, 2017, Nat Struct Mol Biol 24(11): 920-930; Cunningham et al, 2015, Nat Cell Biol 17(2): 160-169). USP30 inactivation can also increase mitochondrial protein import, potentially through ubiquitylation of TOM proteins (Jacoupy et al, 2019, Sci Rep 9(1): 11829). A small proportion of USP30 has been localized to peroxisomes, which are generated through fusion of mitochondrial and ER vesicles, with USP30 potentially antagonizing the Pex2/pexophagy pathway (Riccio et al, 2019, J Cell Biol 218(3): 798-807). The E3 Ub ligase March5 and the deubiquitinase USP30 associate with the translocase and regulate mitochondrial import, and while March5 opposes mitochondrial import and directs degradation of substrates, USP30 deubiquitinates substrates to promote their import (Phu et al, 2020, Molecular Cell 77, 1107-1123).

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of a number of proteins that have been implicated with early onset PD. While most PD cases are linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and also enhances parkin-induced cell death. USP30 has also been shown to regulate BAX/BAK-dependent apoptosis independently of parkin overexpression. Depletion of USP30 sensitises cancer cells to BH-3 mimetics such as ABT-737, without the need for parkin overexpression. Thus, an anti-apoptotic role has been demonstrated for USP30 and USP30 is therefore a potential target for anti-cancer therapy.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteasome, such as DUBs, are predicted to be better tolerated (Bedford et al, 2011, Nature Rev 10:29-46).

Fibrotic diseases, including renal, hepatic and pulmonary fibrosis, are a leading cause of morbidity and mortality and can affect all tissues and organ systems. Fibrosis is considered to be the result of acute or chronic stress on the tissue or organ, characterized by extracellular matrix deposition, reduction of vascular/tubule/duct/airway patency and impairment of function ultimately resulting in organ failure. Many fibrotic conditions are promoted by lifestyle or environmental factors; however, a proportion of fibrotic conditions can be initiated through genetic triggers or indeed are considered idiopathic (i.e. without a known cause). Certain fibrotic disease, such as idiopathic pulmonary fibrosis (IPF), can be treated with non-specific kinase inhibitor (nintedanib) or drugs without a well-characterized mechanism of action (pirfenidone). Other treatments for organ fibrosis, such as kidney or liver fibrosis, alleviate pressure on the organ itself (e.g. beta blockers for cirrhosis, angiotensin receptor blockers for chronic kidney disease). Attention to lifestyle factors, such as glucose and diet control, may also influence the course and severity of disease.

Mitochondrial dysfunction has been implicated in a number of fibrotic diseases, with oxidative stress downstream of dysfunction being the key pathogenic mediator, alongside decreased ATP production. In preclinical models, disruption of the mitophagy pathway (through mutation or knockout of either parkin or PINK1) exacerbates lung fibrosis and kidney fibrosis, with evidence of increased oxidative stress.

Kurita et al, 2017, Respiratory Research 18:114, discloses that accumulation of profibrotic myofibroblasts is a crucial process for fibrotic remodelling in IPF. Recent findings are said to show participation of autophagy/mitophagy, part of the lysosomal degradation machinery, in IPF pathogenesis, and that mitophagy has been implicated in myofibroblast differentiation through regulating mitochondrial reactive oxygen species (ROS)-mediated platelet-derived growth factor receptor (PDGFR) activation. Kurita's results suggested that pirfenidone induces PARK2-mediated mitophagy and also inhibits lung fibrosis development in the setting of insufficient mitophagy, which may at least partly explain the anti-fibrotic mechanisms for IPF treatment.

Williams et al, 2015, Pharmacol Res. December; 102: 264-269, discuss the role of PINK1-Parkin-mediated autophagy in protecting against alcohol and acetaminophen-induced liver injury by removing damaged mitochondria via mitophagy. It is suggested that pharmacological stabilization of USP8 or inactivation of USP15 and USP30 may be potential therapeutic targets for upregulating Parkin-induced mitophagy and in turn protect against drug-induced liver injury. However, it is noted that the DUBs are regulated both transcriptionally and post-translationally, which may make drug development for targeting these specific enzymes challenging, and in addition, phosphorylated ubiquitin was shown to be resistant to DUBs. The authors conclude that upregulating PINK1 stabilization or kinase activity may be a more effective target than inhibiting DUBs.

Williams et al, 2015, Biomolecules 5, 2619-2642, and Williams et al, 2015, Am J Physiol Gastrointest Liver Physiol 309: G324-G340, review mechanisms involved in regulation of mitochondrial homeostasis in the liver and how these mechanisms may protect against alcohol-induced liver disease.

Luciani et al, 2020, Nat. Commun. 11, 970, reports deregulation of mitochondrial network in terminally differentiated cells contributes to a broad spectrum of disorders, including methylmalonic acidemia (MMA). MMA is one of the most common inherited metabolic disorders, due to deficiency of the mitochondrial methylmalonyl-coenzyme A mutase (MMUT). MMUT deficiency induces metabolic and mitochondrial alterations that are exacerbated by anomalies in PINK1/Parkin-mediated mitophagy, causing the accumulation of dysfunctional mitochondria that trigger epithelial stress and ultimately cell damage. A link is suggested between primary MMUT deficiency, diseased mitochondria, mitophagy dysfunction and epithelial stress, and potential therapeutic perspectives for MMA is provided.

Kluge et al, Bioorganic & Medicinal Chemistry Letters, 2018, 28 2655-2659, reports that selective inhibitors of USP30 accelerate mitophagy.

Series of derivatives of N-cyano-substituted heterocycles are disclosed as deubiquitylating enzyme inhibitors in PCT applications WO 2016/046530 (U.S. Ser. No. 15/513,125, U.S. Ser. No. 15/894,025, U.S. Ser. No. 16/448,066), WO 2016/156816 (U.S. Ser. No. 15/558,632, U.S. Ser. No. 16/297,937, U.S. Ser. No. 16/419,558, U.S. Ser. No. 16/419,747, U.S. Ser. No. 16/788,446), WO 2017/009650 (U.S. Ser. No. 15/738,900), WO 2017/093718 (U.S. Ser. No. 15/776,149), WO 2017/103614 (U.S. Ser. No. 15/781,615), WO 2017/149313 (U.S. Ser. No. 16/078,518), WO 2017/109488 (U.S. Ser. No. 16/060,299), WO 2017/141036 (U.S. Ser. No. 16/070,936), WO 2017/163078 (U.S. Ser. No. 16/087,515), WO 2017/158381 (U.S. Ser. No. 16/080,229), WO 2017/158388 (U.S. Ser. No. 16/080,506), WO 2018/065768 (U.S. Ser. No. 16/336,685), WO 2018/060742 (U.S. Ser. No. 16/336,202), WO 2018/060689 (U.S. Ser. No. 16/334,836), WO 2018/060691 (U.S. Ser. No. 16/336,363), WO 2018/220355 (U.S. Ser. No. 16/615,040), WO 2018/234755 (U.S. Ser. No. 16/615,709), WO 2020/212350, WO 2020/212351, WO 2021/043870 and PCT/EP2021/064166, each of which are expressly incorporated herein by reference. PCT application WO 2019/171042 (U.S. Ser. No. 16/977,019), which is expressly incorporated herein by reference, discloses the use of N-cyanopyrrolidines as inhibitors of USP30 for the treatment of fibrotic diseases.

Falgueyret et al, 2001, J. Med. Chem. 44, 94-104, and PCT application WO 01/77073 refer to cyanopyrrolidines as inhibitors of Cathepsins K and L, with potential utility in treating osteoporosis and other bone-resorption related conditions. PCT application WO 2015/179190 refers to N-acylethanolamine hydrolysing acid amidase inhibitors, with potential utility in treating ulcerative colitis and Crohn's disease. PCT application WO 2013/030218 refers to quinazolin-4-one compounds as inhibitors of ubiquitin specific proteases, such as USP7, with potential utility in treating cancer, neurodegenerative diseases, inflammatory disorders and viral infections. PCT applications WO 2015/017502 and WO 2016/019237 refer to inhibitors of Bruton's tyrosine kinase with potential utility in treating disease such as autoimmune disease, inflammatory disease and cancer. PCT applications WO 2009/026197, WO 2009/129365, WO 2009/129370, and WO 2009/129371, refer to cyanopyrrolidines as inhibitors of Cathepsin C with potential utility in treating COPD. United States patent application US 2008/0300268 refers to polyaromatic compounds as inhibitors of tyrosine kinase receptor PDGFR. PCT applications WO 2019/222468, WO 2019/071073, WO 2020/036940 and WO 2020/072964, Rusilowicz-Jones et al, 2020, bioRxiv 2020.04.16.044206 (20 Apr. 2020), and Tsefou et al, bioRxiv 2021.02.02.429344 (2 Feb. 2021), refer to cyanamide-containing compounds as USP30 inhibitors. Yue et al, 2014, Cell Research, 24, 482-496, refers to a diterpenoid derivative 15-oxospiramilactone as a USP30 inhibitor that induced mitochondrial fusion.

PCT application WO 2015/183987 refers to pharmaceutical compositions comprising deubiquitinase inhibitors and human serum albumin in methods of treating cancer, fibrosis, an autoimmune disease or condition, an inflammatory disease or condition, a neurodegenerative disease or condition or an infection. It is noted that deubiquitinases, including UCHL5/UCH37, USP4, USP9X, USP11 and USP15, are said to have been implicated in the regulation of the TGF-beta signalling pathway, the disruption of which gives rise to neurodegenerative and fibrotic diseases, autoimmune dysfunction and cancer.

PCT application WO 2006/067165 refers to a method for treating fibrotic diseases using indolinone kinase inhibitors.

PCT application WO 2007/119214 refers to a method for treating early stage pulmonary fibrosis using an endothelin receptor antagonist. PCT application WO 2012/170290 refers to a method for treating fibrotic diseases using THC acids. PCT application WO 2018/213150 refers to sulfonamide USP30 inhibitors with potential utility in the treatment of conditions involving mitochondrial defects. Larson-Casey et al, 2016, Immunity 44, 582-596, concerns macrophage Akt1 kinase-mediated mitophagy, apoptosis resistance and pulmonary fibrosis. Tang et al, 2015, Kidney Diseases 1, 71-79, reviews the potential role of mitophagy in renal pathophysiology.

There exists a need for safe, alternative, and/or improved methods and compositions for the treatment or prevention of conditions involving mitochondrial dysfunction, cancer and fibrosis, and the various symptoms and conditions associated therewith. While not wishing to be bound by any particular theory or mechanism, it is believed that the compounds of the present invention act to inhibit the enzyme USP30, which in turn upregulates Parkin-induced mitophagy.

Acute Kidney Injury (AKI) is defined as an abrupt decrease in kidney function occurring over 7 days or less, with severity of injury staged based on increased serum creatinine (SCr) and decreased urine output as described in the Kidney Disease Improving Global Outcomes (KDIGO) guidelines. AKI occurs in about 13.3 million people per year, 85% of whom live in the developing world and it is thought to contribute to about 1.7 million deaths every year (Mehta et al, 2015, Lancet 385(9987): 2616-2643). AKI more than likely results in permanent kidney damage (i.e., chronic kidney disease; CKD) and may also result in damage to non-renal organs. AKI is a significant public health concern particularly when considering the absolute number of patients developing incident CKD, progressive CKD, end-stage renal disease and cardiovascular events. AKI has been found to be prevalent in patients hospitalised by COVID-19 and is strongly associated with hospital mortality, with mitochondrial damage and dysfunction reported as a potential pathophysiological mechanism and therapeutic target (Kellum et al, Nephrol Dial Transplant (2020) 35: 1652-1662).

AKI and CKD are viewed as a continuum on the same disease spectrum (Chawla et al, 2017, Nat Rev Nephrol 13(4): 241-257). Patients undergoing coronary artery bypass graft (CABG) are at high risk for kidney injury. There is an obvious unmet medical need in the development of medicinal products for the treatment and/or prevention of AKI.

The kidney is a site of high metabolic demand, with high mitophagy rates demonstrated in vivo (McWilliams et al, 2018, Cell Metab 27(2): 439-449 e435). Renal Proximal Tubule Epithelial Cells (RPTECs), a cell type with significant ATP requirement for solute/ion exchange, are rich in mitochondria and are the primary effector cells of Acute Kidney Injury (AKI) in the kidney. Mitochondrial dysfunction has been implicated in AKI/CKD mechanisms, both through multiple lines of evidence from preclinical AKI and CKD models and also through data demonstrating abnormal mitochondrial phenotypes in patient biopsies (Emma et al, 2016, Nat Rev Nephrol 12(5): 267-280; Eirin et al, 2017, Handb Exp Pharmacol 240: 229-250). Furthermore, Primary mitochondrial disease often manifest in renal symptoms, such as focal segmental glomerulosclerosis (Kawakami et al, 2015, J Am Soc Nephrol 26(5): 1040-1052) in patients with MELAS/MIDD, and also primary tubular pathologies in patients with Coenzyme Q deficiencies. Mutations in mtDNA can cause maternally inherited tubulointerstitial disease (Connor et al, 2017, PLoS Genet 13(3): e1006620).

Regarding mitochondrial quality control in renal injury (Tang et al, 2018, Autophagy 14(5): 880-897) demonstrated that renal injury was exacerbated following ischemic AKI in both PINK1 KO and PARK2 KO mice, suggesting that PINK1/PARKIN-mediated mitophagy plays a protective role following IRI in the kidney. In addition, parkin/PINK1 mitophagy protects against cisplatin induced kidney injury (Wang et al, 2018, Cell Death Dis 9(11): 1113). Limited models of CKD are available for mitophagy investigation, supportive evidence for mitochondrial quality control in fibrosis comes from studies on fibrotic lung conditions such as COPD and IPF. Parkin knockout animals show exacerbated lung fibrosis in response to bleomycin (Kobayashi et al, 2016, J Immunol, 197:504-516). Similarly, airway epithelial cells from parkin knockout (KO) animals show exacerbated fibrotic and senescent responses to cigarette smoke (Araya et al, 2019, Autophagy 15(3): 510-526).

Preclinical models are available to study potential novel therapeutics, through their ability to model fibrosis pathology (e.g. collagen deposition) consistent with the human condition. Preclinical models can be toxin-mediated (e.g. bleomycin for lung and skin fibrosis), surgical (e.g. ischemia/reperfusion injury model and unilateral ureter obstruction model for acute tubulointerstitial fibrosis), and genetic (e.g. diabetic (db/db) mice for diabetic nephropathy). For example, both examples previously given for indicated IPF treatments (nintedanib and pirfenidone) show efficacy in the bleomycin lung fibrosis model.

Accordingly, there is a need for compounds that are inhibitors of USP30 for the treatment or prevention of conditions where inhibition of USP30 is indicated. In particular, there exists a need for USP30 inhibitors that have suitable and/or improved properties in order to maximise efficacy against the target disease.

SUMMARY OF THE INVENTION

The present invention is directed to a compound of formula (I), which is selected from formula (I)(i) and formula (I)(ii):

(I)(i)

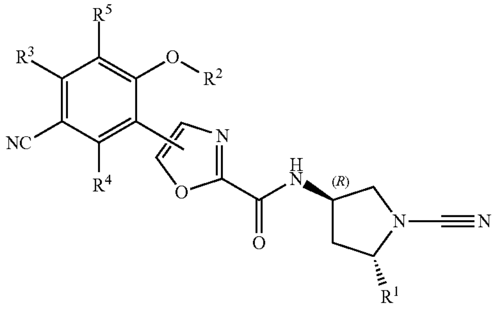

-continued (I)(ii)

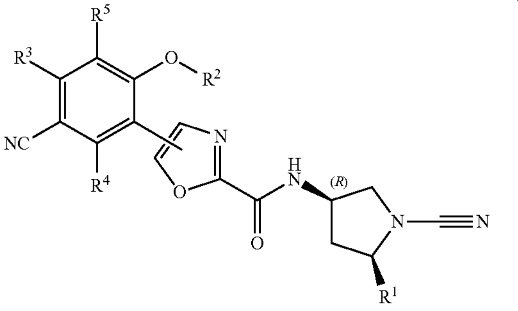

a tautomer thereof, or a pharmaceutically acceptable salt of said compound or tautomer, wherein:

$R^1$ is selected from $(C_1\text{-}C_4)$alkyl, $(C_1\text{-}C_4)$fluoroalkyl and $CH_2OCH_3$;

$R^2$ is selected from $(C_1\text{-}C_4)$alkyl, $CF_3$ and cyclopropyl; and $R^3$, $R^4$ and $R^5$ are each independently selected from hydrogen and halogen.

The present invention is also directed to uses of the compounds of formula (I), particularly in the treatment of conditions involving mitochondrial dysfunction, cancer and fibrosis, and also processes for the preparation thereof and pharmaceutical compositions containing said compounds.

DETAILED DESCRIPTION OF THE INVENTION

The present invention is directed to USP30 inhibitors that have suitable and/or improved properties in order to maximise efficacy against the target disease. Such properties include, for example, potency, selectivity, physicochemical properties, ADME (absorption, distribution, metabolism and excretion) properties, including PK (pharmacokinetic) profile, and safety profile.

It is generally desirable to maximise the potency of a drug molecule against the target enzyme in relevant assays in order to lower the effective/efficacious dosage that is to be administered to patients. Compounds of the invention may be tested for USP30 affinity using the in vitro biochemical fluorescence polarization (FP) assay described herein.

USP30 is a transmembrane protein located in the outer membrane of mitochondria, which are energy-producing organelles present inside cells. Therefore, being able to demonstrate cellular activity in vitro is advantageous, as this is one of a number of components that may indicate a greater ability to engage the target in its physiological setting, i.e. where the USP30 inhibitor compound is able to penetrate cells. The USP30 cellular western blot (WB) assay described herein aims to test the activity of compounds against USP30 in cells using an irreversible activity probe to monitor USP30 activity. Analogously to the cellular western blot assay, target engagement assessment (ex vivo) may be carried out in either brain or kidney tissue samples from compound-dosed animals.

To extend target binding knowledge to downstream pharmacodynamics, assessment of TOM20 (an outer mitochondrial membrane protein) ubiquitylation may be made.

In general, it is important for a drug to be as selective as possible for its desired target enzyme; additional activities give rise to the possibility of side effects. The exact physiological role of many DUBs has yet to be fully determined, however, irrespective of whatever role these DUBs may or may not play, it is a sound medicinal chemistry precept to ensure that any drug has selectivity over related mechanistic targets of unknown physiological function. Representative examples of DUB enzymes for which the compounds of the present invention may be screened against are UCHL1, UCHL3, UCHL5, YOD1, SENP2, SENP6, TRABID, BAP1, Cezanne, MINDY2/FAM63B, OTU1, OTUD3, OTUD5, OTUD6A, OTUD6B, OTUB1/UBCH5B, OTUB2, CYLD, VCPIP, AMSH-LP, JOSD1, JOSD2, USP1/UAF1, USP2, USP4, USP5, USP6, USP7, USP8, USP9x, USP10, USP11, USP12/UAF1, USP13, USP14, USP15, USP16, USP19, USP20, USP21, USP22, USP24, USP25, USP28, USP32, USP34, USP35, USP36, USP45, USP46/UAF1, USP47 and USP48. Preferably, compounds of the invention have good selectivity for USP30 over one or more of these DUB enzymes.

Aside from selectivity over other DUB enzymes, it is important for a drug to have low affinity for other targets, and pharmacological profiling may be performed against panels of targets to assess the potential for, and to minimise, potential off-target effects. Examples of targets for which the compounds of the present invention may be screened against are those of the industry standard Eurofins-Cerep Safety-Screen44 panel, which includes 44 targets as a representative selection of GPCR receptors, transporters, ion channels, nuclear receptors, and kinase and non-kinase enzymes. Preferably, compounds of the invention have insignificant affinity against targets of this screening panel. Further examples of targets for which the compounds of the present invention may be screened against are kinases of the Thermo Fisher SelectScreen kinase profiling panel, which includes 39 targets as a representative selection of kinase enzymes. Preferably, compounds of the invention have insignificant affinity against targets of this screening panel. Additionally, examples of a particular enzyme class for which the compounds of the present invention may be screened against are the cathepsins (e.g. cathepsin A, B, C, H, K, L, L2, S, V and Z). Preferably, compounds of the invention have good selectivity for USP30 over one or more of these enzymes.

There is also a need for compounds that have favourable pharmacokinetic properties such that they are suitable for oral administration. An orally administered drug should have good bioavailability; that is an ability to readily cross the gastrointestinal (GI) tract and not be subject to extensive metabolism as it passes from the GI tract into the systemic circulation. Once a drug is in the systemic circulation the rate of metabolism is also important in determining the time of residence of the drug in the body.

Thus, it is clearly favourable for drug molecules to have the properties of being readily able to cross the GI tract and being only slowly metabolised in the body. The Caco-2 assay is a widely accepted model for predicting the ability of a given molecule to cross the GI tract. The majority of metabolism of drug molecules generally occurs in the liver, and in vitro assays using whole cell hepatocytes (animal or human) are widely accepted methods for measuring the susceptibility of a given molecule towards metabolism in the liver. Such assays aim to predict in vivo clearance from the hepatocyte calculated clearance value.

Compounds which have good Caco-2 flux and are stable towards hepatocytes are predicted to have good oral bioavailability (good absorption across the GI tract and minimal extraction of compound as it passes through the liver) and a long residence time in the body that is sufficient for the drug to be efficacious.

The solubility of a compound is an important factor in achieving a desired concentration of drug in systemic circulation for the anticipated pharmacological response. Low aqueous solubility is a problem encountered with formulation development of new chemical entities and to be absorbed a drug must be present in the form of solution at the site of absorption. The kinetic solubility of a compound may be measured using a turbidimetric solubility assay, the data from which may also be used in conjunction with Caco-2 permeability data to predict dose dependent human intestinal absorption.

Other parameters that may be measured using standard assays that are indicative of a compound's exposure profile include, for example plasma stability (half-life measurement), blood AUC, $C_{max}$, $C_{min}$ and $T_{max}$ values.

The treatment of CNS disorders, including Alzheimer's disease, Parkinson's disease, and other disorders described herein, requires drug molecules to target the brain, which requires adequate penetration of the blood brain barrier. There is, therefore, a need for USP30 inhibitors that possess effective blood brain penetration properties and provide suitable residence time in the brain to be efficacious. The probability that a compound can cross the blood brain barrier may be measured by an in vitro flux assay utilizing a MDR1-MDCK cell monolayer (Madin-Darby Canine Kidney cells transfected with MDR-1 resulting in overexpression of the human efflux transporter P-glycoprotein). Additionally, exposure may also be measured directly in brain and plasma using in vivo animal models.

There is also a need for compounds that have a favourable safety profile, which may be measured by a variety of standard in vitro and in vivo methods. A cell toxicity counter-screen may be used to assay the anti-proliferative/cytotoxic effect in a particular cell line (e.g. HCT116) by fluorometric detection of rezasurin (alamarBlue™) to resofurin in response to mitochondrial activity.

Toxicology and safety studies may also be conducted to identify potential target organs for adverse effects and define the Therapeutic Index to set the initial starting doses in clinical trials. Regulatory requirements generally require studies to be conducted in at least two laboratory animal species, one rodent (rat or mouse) and one nonrodent (rabbit, dog, non-human primate, or other suitable species).

The bacterial reverse mutation assay (Ames Test) may be used to evaluate the mutagenic properties of compounds of the invention, commonly by using the bacterial strain *Salmonella typhimurium*, which is mutant for the biosynthesis of the amino acid histidine.

The micronucleus assay may be used to determine if a compound is genotoxic by evaluating the presence of micronuclei. Micronuclei may contain chromosome fragments produced from DNA breakage (clastogens) or whole chromosomes produced by disruption of the mitotic apparatus (aneugens).

The hERG predictor assay provides valuable information about the possible binding of test compounds to the potassium channel and potential QT prolongation on echocardiogram. Inhibition of the hERG current causes QT interval prolongation resulting in potentially fatal ventricular tachyarrhythmia (Torsades de Pointes). Typically, assay data may be generated from an automated patch-clamp assay platform.

The present invention is therefore directed to USP30 inhibitors that have suitable and/or improved properties in order to maximise efficacy against the target disease. Such properties include, for example, potency, selectivity, physicochemical properties, ADME (absorption, distribution, metabolism and excretion) properties, including PK (pharmacokinetic) profile, and safety profile.

Compounds of the present invention have been found to demonstrate one or more of the above identified properties that are both significant and unexpected. For instance, Examples 1 to 12 of the present invention are highly potent for USP30, as measured in the biochemical assay described herein. All of these Examples (1 to 12) of the present invention are significantly more selective for USP30 over other DUBs and cathepsins. The significant and unexpected properties of the compounds of the present invention make them particularly suitable for use in the treatment and/or prevention of diseases linked to USP30 activity.

According to a first aspect, the present invention provides a compound of formula (I), which is selected from formula (I)(i) and formula (I)(ii):

(I)(i)

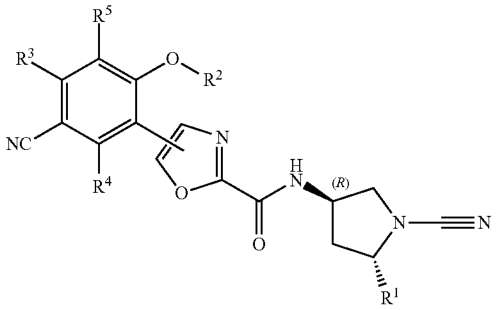

(I)(ii)

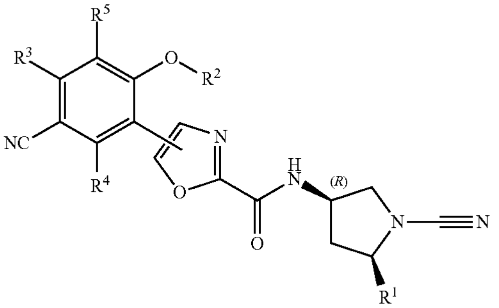

a tautomer thereof, or a pharmaceutically acceptable salt of said compound or tautomer, wherein:

$R^1$ is selected from $(C_1-C_4)$alkyl, $(C_1-C_4)$fluoroalkyl and $CH_2OCH_3$;

$R^2$ is selected from $(C_1-C_4)$alkyl, $CF_3$ and cyclopropyl; and $R^3$, $R^4$ and $R^5$ are each independently selected from hydrogen and halogen.

The compound of formula (I) exists as a single stereoisomer with the absolute stereochemistry shown.

Alkyl groups may be straight or branched and contain 1 to 4 carbon atoms. Examples of alkyl include methyl, ethyl, n-propyl, isopropyl, n-butyl, isobutyl, and sec-butyl.

Halogen means fluorine, chlorine, bromine or iodine, in particular, fluorine or chlorine. Fluoroalkyl groups may contain one or more fluorine substituents. Examples are fluoromethyl, difluoromethyl and trifluoromethyl.

Unless otherwise indicated, the term substituted means substituted by one or more defined groups. In the case where groups may be selected from more than one alternative, the selected groups may be the same or different. The term 'independently' means that where more than one substituent is selected from more than one possible substituent, those substituents may be the same or different.

Preferred embodiments of the compound of formula (I) are defined below.

Preferably, $R^1$ is selected from methyl, $CH_2F$, $CHF_2$, $CF_3$ and $CH_2OCH_3$.

More preferably, $R^1$ is selected from methyl, $CH_2F$ and $CH_2OCH_3$.

Most preferably, $R^1$ is selected from methyl and $CH_2OCH_3$.

Preferably, $R^2$ is selected from methyl, $CF_3$ and cyclopropyl.

Most preferably, $R^2$ is selected from methyl and cyclopropyl.

Preferably, $R^3$ is selected from hydrogen, chlorine and fluorine.

More preferably, $R^3$ is selected from hydrogen and fluorine.

Most preferably, $R^3$ is hydrogen.

Preferably, $R^4$ and $R^5$ are each independently selected from hydrogen and fluorine.

Most preferably, $R^4$ and $R^5$ are each hydrogen.

According to one aspect of the invention, the compound of formula (I) has the formula (I)(i):

(I)(i)

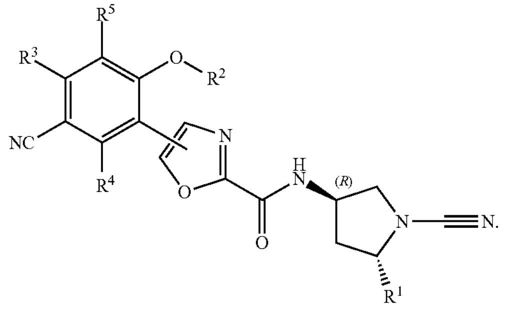

According to another aspect of the invention, the compound of formula (I) has the formula (I)(ii):

(I)(ii)

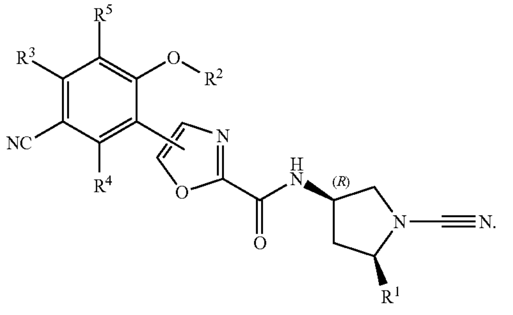

According to a first preferred aspect of the invention is the compound of formula (IA)(i):

(IA)(i)

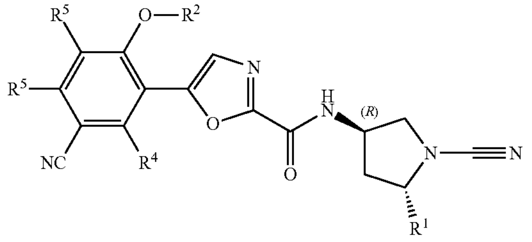

a tautomer thereof, or a pharmaceutically acceptable salt of said compound or tautomer, wherein:

$R^1$ is selected from $(C_1\text{-}C_4)$alkyl, $(C_1\text{-}C_4)$fluoroalkyl and $CH_2OCH_3$;

$R^2$ is selected from $(C_1\text{-}C_4)$alkyl, $CF_3$ and cyclopropyl; and $R^3$, $R^4$ and $R^5$ are each independently selected from hydrogen and halogen.

Preferred embodiments of the compound of formula (IA)(i) are defined below.

Preferably, $R^1$ is selected from methyl, $CH_2F$, $CHF_2$, $CF_3$ and $CH_2OCH_3$.

More preferably, $R^1$ is selected from methyl, $CH_2F$ and $CH_2OCH_3$.

Most preferably, $R^1$ is selected from methyl and $CH_2OCH_3$.

Preferably, $R^2$ is selected from methyl, $CF_3$ and cyclopropyl.

Most preferably, $R^2$ is selected from methyl and cyclopropyl.

Preferably, $R^3$ is selected from hydrogen, chlorine and fluorine.

More preferably, $R^3$ is selected from hydrogen and fluorine.

Most preferably, $R^3$ is hydrogen.

Preferably, $R^4$ and $R^5$ are each independently selected from hydrogen and fluorine.

Most preferably, $R^4$ and $R^5$ are each hydrogen.

Preferred compounds of formula (IA)(i) of the present invention are selected from:

5-(5-cyano-2-cyclopropoxyphenyl)-N-((3R,5R)-1-cyano-5-methylpyrrolidin-3-yl)oxazole-2-carboxamide;

5-(5-cyano-2-cyclopropoxyphenyl)-N-((3R,5S)-1-cyano-5-(methoxymethyl)pyrrolidin-3-yl)oxazole-2-carboxamide;

5-(5-cyano-2-cyclopropoxyphenyl)-N-((3R,5S)-1-cyano-5-(fluoromethyl)pyrrolidin-3-yl)oxazole-2-carboxamide;

5-(5-cyano-2-methoxyphenyl)-N-((3R,5R)-1-cyano-5-methylpyrrolidin-3-yl)oxazole-2-carboxamide;

5-(5-cyano-2-methoxyphenyl)-N-((3R,5S)-1-cyano-5-(methoxymethyl)pyrrolidin-3-yl)oxazole-2-carboxamide;

5-(5-cyano-2-(trifluoromethoxy)phenyl)-N-((3R,5S)-1-cyano-5-(methoxymethyl)pyrrolidin-3-yl)oxazole-2-carboxamide;

5-(5-cyano-2-(trifluoromethoxy)phenyl)-N-((3R,5R)-1-cyano-5-methylpyrrolidin-3-yl)oxazole-2-carboxamide; and 5-(5-cyano-4-fluoro-2-methoxyphenyl)-N-((3R,5R)-1-cyano-5-methylpyrrolidin-3-yl)oxazole-2-carboxamide;

or a pharmaceutically acceptable salt thereof.

Most preferred compounds of formula (IA)(i) of the present invention are selected from:

5-(5-cyano-2-cyclopropoxyphenyl)-N-((3R,5R)-1-cyano-5-methylpyrrolidin-3-yl)oxazole-2-carboxamide; and 5-(5-cyano-2-cyclopropoxyphenyl)-N-((3R,5S)-1-cyano-5-(methoxymethyl)pyrrolidin-3-yl)oxazole-2-carboxamide;

or a pharmaceutically acceptable salt thereof.

According to a second preferred aspect of the invention is the compound of formula (IB)(i):

(IB)(i)

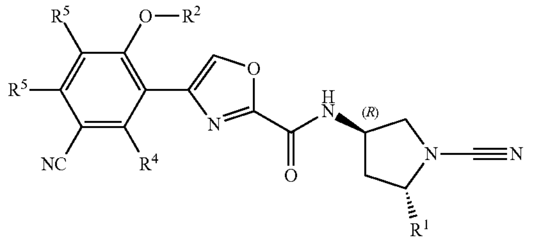

a tautomer thereof, or a pharmaceutically acceptable salt of said compound or tautomer, wherein:

$R^1$ is selected from $(C_1-C_4)$alkyl, $(C_1-C_4)$fluoroalkyl and $CH_2OCH_3$;

$R^2$ is selected from $(C_1-C_4)$alkyl, $CF_3$ and cyclopropyl; and $R^3$, $R^4$ and $R^5$ are each independently selected from hydrogen and halogen.

Preferred embodiments of the compound of formula (IB)(i) are defined below.

Preferably, $R^1$ is selected from methyl, $CH_2F$, $CHF_2$, $CF_3$ and $CH_2OCH_3$.

More preferably, $R^1$ is selected from methyl, $CH_2F$ and $CH_2OCH_3$.

Most preferably, $R^1$ is $CH_2OCH_3$.

Preferably, $R^2$ is selected from methyl, $CF_3$ and cyclopropyl.

Most preferably, $R^2$ is methyl.

Preferably, $R^3$ is selected from hydrogen, chlorine and fluorine.

More preferably, $R^3$ is selected from hydrogen and fluorine.

Most preferably, $R^3$ is hydrogen.

Preferably, $R^4$ and $R^5$ are each independently selected from hydrogen and fluorine.

Most preferably, $R^4$ and $R^5$ are each hydrogen.

Preferred compounds of formula (IB)(i) of the present invention are selected from:

4-(5-cyano-2-methoxyphenyl)-N-((3R,5S)-1-cyano-5-(methoxymethyl)pyrrolidin-3-yl)oxazole-2-carboxamide; and 4-(5-cyano-2-cyclopropoxyphenyl)-N-((3R,5S)-1-cyano-5-(methoxymethyl)pyrrolidin-3-yl)oxazole-2-carboxamide;

or a pharmaceutically acceptable salt thereof.

According to a third preferred aspect of the invention is the compound of formula (IA)(ii):

(IA)(ii)

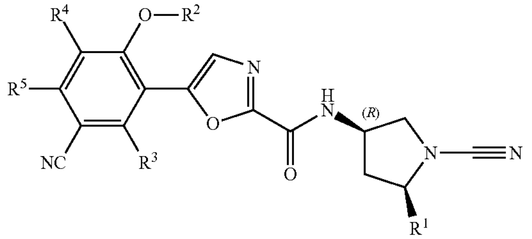

a tautomer thereof, or a pharmaceutically acceptable salt of said compound or tautomer, wherein:

$R^1$ is selected from $(C_1-C_4)$alkyl, $(C_1-C_4)$fluoroalkyl and $CH_2OCH_3$;

$R^2$ is selected from $(C_1-C_4)$alkyl, $CF_3$ and cyclopropyl; and $R^3$, $R^4$ and $R^5$ are each independently selected from hydrogen and halogen.

Preferred embodiments of the compound of formula (IA)(ii) are defined below.

Preferably, $R^1$ is selected from methyl, $CH_2F$, $CHF_2$, $CF_3$ and $CH_2OCH_3$.

More preferably, $R^1$ is selected from methyl, $CH_2F$ and $CH_2OCH_3$.

Most preferably, $R^1$ is selected from methyl and $CH_2OCH_3$.

Preferably, $R^2$ is selected from methyl, $CF_3$ and cyclopropyl.

Most preferably, $R^2$ is selected from methyl and cyclopropyl.

Preferably, $R^3$ is selected from hydrogen, chlorine and fluorine.

More preferably, $R^3$ is selected from hydrogen and fluorine.

Most preferably, $R^3$ is hydrogen.

Preferably, $R^4$ and $R^5$ are each independently selected from hydrogen and fluorine.

Most preferably, $R^4$ and $R^5$ are each hydrogen.

Preferred compounds of formula (IA)(ii) of the present invention are selected from:

5-(5-cyano-2-cyclopropoxyphenyl)-N-((3R,5R)-1-cyano-5-(methoxymethyl)pyrrolidin-3-yl)oxazole-2-carboxamide;

5-(5-cyano-2-cyclopropoxyphenyl)-N-((3R,5S)-1-cyano-5-methylpyrrolidin-3-yl)oxazole-2-carboxamide;

5-(5-cyano-2-methoxyphenyl)-N-((3R,5S)-1-cyano-5-methylpyrrolidin-3-yl)oxazole-2-carboxamide;

5-(5-cyano-2-methoxyphenyl)-N-((3R,5R)-1-cyano-5-(methoxymethyl)pyrrolidin-3-yl)oxazole-2-carboxamide;

5-(5-cyano-2-(trifluoromethoxy)phenyl)-N-((3R,5R)-1-cyano-5-(methoxymethyl)pyrrolidin-3-yl)oxazole-2-carboxamide;

5-(5-cyano-2-(trifluoromethoxy)phenyl)-N-((3R,5S)-1-cyano-5-methylpyrrolidin-3-yl)oxazole-2-carboxamide;

5-(5-cyano-4-fluoro-2-methoxyphenyl)-N-((3R,5S)-1-cyano-5-methylpyrrolidin-3-yl)oxazole-2-carboxamide; and 5-(5-cyano-2-cyclopropoxyphenyl)-N-((3R,5R)-1-cyano-5-(fluoromethyl)pyrrolidin-3-yl)oxazole-2-carboxamide;

or a pharmaceutically acceptable salt thereof.

According to a fourth preferred aspect of the invention is the compound of formula (IB)(ii):

(IB)(ii)

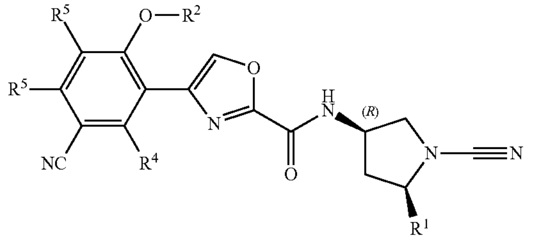

a tautomer thereof, or a pharmaceutically acceptable salt of said compound or tautomer, wherein:

$R^1$ is selected from $(C_1-C_4)$alkyl, $(C_1-C_4)$fluoroalkyl and $CH_2OCH_3$;

$R^2$ is selected from $(C_1-C_4)$alkyl, $CF_3$ and cyclopropyl; and $R^3$, $R^4$ and $R^5$ are each independently selected from hydrogen and halogen.

Preferred embodiments of the compound of formula (IB)(ii) are defined below.

Preferably, $R^1$ is selected from methyl, $CH_2F$, $CHF_2$, $CF_3$ and $CH_2OCH_3$.

More preferably, $R^1$ is selected from methyl, $CH_2F$ and $CH_2OCH_3$.

Most preferably, $R^1$ is $CH_2OCH_3$.

Preferably, $R^2$ is selected from methyl, $CF_3$ and cyclopropyl.

Most preferably, $R^2$ is methyl.

Preferably, $R^3$ is selected from hydrogen, chlorine and fluorine.

More preferably, $R^3$ is selected from hydrogen and fluorine.

Most preferably, $R^3$ is hydrogen.

Preferably, $R^4$ and $R^5$ are each independently selected from hydrogen and fluorine.

Most preferably, $R^4$ and $R^5$ are each hydrogen.

Preferred compounds of formula (IB)(ii) of the present invention are selected from:

4-(5-cyano-2-cyclopropoxyphenyl)-N-((3R,5R)-1-cyano-5-(methoxymethyl)pyrrolidin-3-yl)oxazole-2-carboxamide; and 4-(5-cyano-2-methoxyphenyl)-N-((3R,5R)-1-cyano-5-(methoxymethyl)pyrrolidin-3-yl)oxazole-2-carboxamide; or a pharmaceutically acceptable salt thereof.

Pharmaceutical acceptable salts of the compounds of formula (I) include the acid addition and base salts (including di-salts) thereof.

Suitable acid addition salts are formed from acids which form non-toxic salts. Examples include the acetate, aspartate, benzoate, besylate, bicarbonate/carbonate, bisulfate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D- and L-lactate, malate, maleate, malonate, mesylate, methylsulfate, 2-napsylate, nicotinate, nitrate, orotate, palmate, phosphate, saccharate, stearate, succinate sulfate, D- and L-tartrate, and tosylate salts.

Suitable base salts are formed from bases which form non-toxic salts. Examples include the aluminium, ammonium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of Pharmaceutical Salts: Properties, Selection, and Use, Wiley-VCH, Weinheim, Germany (2002).

A pharmaceutical acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent.

Pharmaceutical acceptable solvates in accordance with the invention include hydrates and solvates wherein the solvent of crystallization may be isotopically substituted, e.g. $D_2O$, acetone-$d_6$, DMSO-$d_6$.

Also, within the scope of the invention are clathrates, drug-host inclusion complexes wherein, in contrast to the aforementioned solvates, the drug and host are present in non-stoichiometric amounts.

For a review of such complexes, see J. Pharm Sci, 64 (8), 1269-1288 by Haleblian (August 1975).

Hereinafter all references to compounds of formula (I) include references to salts thereof and to solvates and clathrates of compounds of formula (I) and salts thereof.

The invention includes all polymorphs of the compounds of formula (I) as hereinbefore defined.

Also, within the scope of the invention are so-called "prodrugs" of the compounds of formula (I). Thus, certain derivatives of compounds of formula (I) which have little or no pharmacological activity themselves can, when metabolised upon administration into or onto the body, give rise to compounds of formula (I) having the desired activity. Such derivatives are referred to as "prodrugs".

Prodrugs in accordance with the invention can, for example, be produced by replacing appropriate functionalities present in the compounds of formula (I) with certain moieties known to those skilled in the art as "pro-moieties" as described, for example, in "Design of Prodrugs" by H Bundgaard (Elsevier, 1985).

Finally, certain compounds of formula (I) may themselves act as prodrugs of other compounds of formula (I).

Certain derivatives of compounds of formula (I) which contain a nitrogen atom may also form the corresponding N-oxide, and such compounds are also within the scope of the present invention.

Included within the scope of the present invention are all tautomeric forms of the compounds of formula (I).

Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of propan-2-ol, typically from 2% to 20%, and from 0 to 5% by volume of an alkylamine, typically 0.1% diethylamine. Concentration of the eluate affords the enriched mixture.

The present invention includes all crystal forms of the compounds of formula (I) including racemates and racemic mixtures (conglomerates) thereof. Stereoisomeric conglomerates may be separated by conventional techniques known to those skilled in the art—see, for example, "Stereochemistry of Organic Compounds" by E. L. Eliel and S. H. Wilen (Wiley, New York, 1994).

The compounds of formula (I) contain two chiral centres at the carbon atoms of the pyrrolidine ring that are substituted by $R^1$ and the amide and said stereocentres could exist in either the (R) or (S) configuration. The designation of the absolute configuration (R) and (S) for stereoisomers in accordance with IUPAC nomenclature is dependent on the nature of the substituents and application of the sequence-rule procedure. The compounds of formula (I) could, therefore, exist in four stereoisomeric forms.

The compounds of formula (I) of the present invention exist as a single stereoisomer. The pyrrolidine carbon atom of the amide substituent exists as the (R)-stereocentre, whereas the designation of the pyrrolidine carbon atom of the $R^1$ group is dependent on the nature of the substituent. The compound of formula (I) is isolated as a single stereoisomer and may exist with a stereoisomeric excess of at least 60%, preferably at least 80%, more preferably at least 90%, more preferably at least 95%, for example 96%, 97%, 98%, 99%, or 100%.

Additional chiral centres may exist in the compounds of formula (I) within the $R^1$ substituent itself. Included within the scope of the present invention are all such stereoisomeric forms of the compounds of formula (I).

The present invention also includes all pharmaceutically acceptable isotopic variations of a compound of formula (I). An isotopic variation is defined as one in which at least one atom is replaced by an atom having the same atomic number, but an atomic mass different from the atomic mass usually found in nature.

Examples of isotopes suitable for inclusion in the compounds of the invention include isotopes of hydrogen, such as $^{2}H$ and $^{3}H$, carbon, such as $^{13}C$ and $^{14}C$, nitrogen, such as $^{15}N$, oxygen, such as $^{17}O$ and $^{18}O$, phosphorus, such as $^{32}P$, sulfur, such as $^{35}S$, fluorine, such as $^{18}F$, and chlorine, such as $^{36}Cl$.

Substitution of the compounds of the invention with isotopes such as deuterium may afford certain therapeutic advantages resulting from greater metabolic stability, for example, increased in vivo half-life or reduced dosage requirements, and hence may be preferred in some circumstances.

Certain isotopic variations of the compounds of formula (I), for example, those incorporating a radioactive isotope, are useful in drug and/or substrate tissue distribution studies. The radioactive isotopes tritium, and $^{14}C$, are particularly useful for this purpose in view of their ease of incorporation and ready means of detection.

Isotopic variations of the compounds of formula (I) can generally be prepared by conventional techniques known to those skilled in the art or by processes analogous to those described in the accompanying Examples and Preparations using appropriate isotopic variations of suitable reagents.

The compounds of formula (I) are inhibitors of the deubiquitylating enzyme USP30.

According to a further aspect, the present invention provides a compound of formula (I) as defined herein, a tautomer thereof, or a pharmaceutically acceptable salt of said compound or tautomer for use as a medicament.

According to a further aspect, the present invention provides a method of treatment or prevention of a disorder or condition where inhibition of USP30 is known, or can be shown, to produce a beneficial effect, in a mammal, comprising administering to said mammal a therapeutically effective amount of a compound of formula (I) as defined herein, a tautomer thereof, or a pharmaceutically acceptable salt of said compound or tautomer.

According to a further aspect, the present invention provides the use of a compound of formula (I) as defined herein, a tautomer thereof, or a pharmaceutically acceptable salt of said compound or tautomer, in the manufacture of a medicament for the treatment or prevention of a disorder or condition where inhibition of USP30 is known, or can be shown, to produce a beneficial effect. The manufacture of a medicament may include, inter alia, the chemical synthesis of the compound of formula (I) or a salt thereof, or the preparation of a composition or formulation comprising the compound or salt, or the packaging of any medicament comprising the compound.

According to a further aspect, the present invention provides a method of inhibition of USP30 in a patient comprising administering to the patient a therapeutically effective amount of a compound of formula (I) as defined herein, a tautomer thereof, or a pharmaceutically acceptable salt of said compound or tautomer.

The disorder or condition benefiting from USP30 activity is selected from a condition involving mitochondrial dysfunction, cancer and fibrosis.

In one preferred embodiment of all aspects of the invention, the disorder or condition benefiting from USP30 activity is a condition involving mitochondrial dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS); mitochondrial encephalopathy, lactic acidosis and stroke-like episodes (MELAS) syndrome; materially-inherited diabetes and deafness (MIDD); Leber's hereditary optic neuropathy (LHON); cancer (including, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, metastatic carcinoma, osteosarcoma, chondosarcoma, Ewing's sarcoma, nasopharyngeal carcinoma, colorectal cancer, and non-small cell lung carcinoma); neuropathy, ataxia, retinitis pigmentosa, maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; Leigh syndrome French Canadian (LSFC) variant; lethal infantile cardiomyopathy (LIC); Luft disease; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; very long-chain acyl-CoA dehydrogenase (VLCAD) deficiency; peroxisomal disorders; methylmalonic acidemia; mevalonate kinase deficiency; age-dependent decline in cognitive function and muscle strength; and cognitive impairment associated with neurodegenerative and neuropsychiatric disorders.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, multiple system atrophy (MSA), progressive supranuclear palsy (PSP), corticobasal degeneration (CBD), and frontotemporal dementia.

In particular, the compounds of the invention may be useful in the treatment or prevention of Parkinson's disease, including, but not limited to, PD related to mutations in α-synuclein, parkin, PINK1, GBA, and LRRK2, and autosomal recessive juvenile Parkinson's disease (AR-JP) or early onset Parkinson's disease (EOPD), where parkin or PINK1 is mutated, truncated, or deleted.

In particular, the compounds of the invention may be useful in treatment of cognitive impairment associated with neurodegenerative and neuropsychiatric disorders, including, for example, cognitive impairment associated with Alzheimer's disease and Parkinson's disease, preclinical or prodromal forms of AD and PD, Huntington's disease, dementia with lewy body disease, cognitive impairment associated with schizophrenia, mood disorders, bipolar and major depressive disorders.

The compounds of the invention or pharmaceutical compositions thereof as described herein may be combined with one or more additional agents when used for the treatment or prevention of conditions involving mitochondrial dysfunction. The compounds may be combined with one or more additional agents selected from levodopa, a dopamine agonist, a monoamino oxygenase (MAO) B inhibitor, a catechol O-methyltransferase (COMT) inhibitor, an anticholinergic, riluzole, amantadine, a cholinesterase inhibitor, memantine, tetrabenazine, an antipsychotic, diazepam, clonazepam, an antidepressant, and an anti-convulsant. The compounds may be combined with agents which reduce/remove pathogenic protein aggregates in neurodegenerative diseases, such as agents which reduce/remove alpha-synuclein in Parkinson's disease, multiple system atrophy or dementia with Lewy bodies; agents which reduce/remove Tau in Alzheimer's disease or progressive supranuclear palsy; agents which reduce/remove TDP-43 in ALS or frontotemporal dementia.

In another preferred embodiment of all aspects of the invention, the disorder or condition benefiting from USP30 activity is cancer. The cancer may be linked to mitochondrial dysfunction. Preferred cancers include, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, metastatic carcinoma, osteosarcoma, chondosarcoma, Ewing's sarcoma, nasopharyngeal carcinoma, colorectal cancer, colorectal cancer, and non-small cell lung carcinoma.

In particular, the compounds of the invention may be useful in the treatment or prevention of cancer where apoptotic pathways are dysregulated and more particularly where proteins of the BCL-2 family are mutated, or over or under expressed.

Fibrosis refers to the accumulation of extracellular matrix constituents that occurs following trauma, inflammation, tissue repair, immunological reactions, cellular hyperplasia, and neoplasia. Fibrotic disorders that may be treated by the compounds and compositions of the present invention include, inter alia, fibrosis/fibrotic disorders associated with major organ diseases, for example, interstitial lung disease (ILD), liver cirrhosis, non-alcoholic fatty liver disease (NAFLD) and non-alcoholic steatohepatitis (NASH) (hepatic fibrosis), kidney disease (renal fibrosis), acute kidney injury (AKI), acute kidney disease (AKD), chronic kidney disease (CKD), delayed kidney graft function, heart or vascular disease (cardiac fibrosis) and diseases of the eye; fibroproliferative disorders, for example, systemic and local scleroderma, keloids and hypertrophic scars, atherosclerosis, restenosis, and Dupuytren's contracture; scarring associated with trauma, for example, surgical complications, chemotherapeutics drug-induced fibrosis (e.g. bleomycin-induced fibrosis), radiation-induced fibrosis, accidental injury and burns); retroperitoneal fibrosis (Ormond's disease); and peritoneal fibrosis/peritoneal scarring in patients receiving peritoneal dialysis, usually following renal transplantation. See, for example, Wynn et al, 2004, Nat Rev Immunol. August; 4(8): 583-594. The present invention therefore relates to methods of treatment or prevention, and compounds and compositions used in said methods, of fibrosis/fibrotic disorders of and/or associated with the major organs, including for example, the lung, liver, kidney, heart, skin, eye, gastrointestinal tract, peritoneum and bone marrow, and other diseases/disorders herein described.

The compounds may be combined with agents which are used as treatments for kidney disease, including anti-diabetic agents, cardiovascular disease agents, and novel agents targeting disease relevant pathways such as oxidative stress (including, but not limited to, the nrf2/keap-1 pathway) and anti-apoptotic pathways (including, but not limited to, anti p53 agents).

Interstitial lung disease (ILD) includes disorders in which pulmonary inflammation and fibrosis are the final common pathways of pathology, for example, sarcoidosis, silicosis, drug reactions, infections and collagen vascular diseases, such as rheumatoid arthritis and systemic sclerosis (scleroderma). The fibrotic disorder of the lung includes, for example, pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, and bronchiectasis.

Idiopathic pulmonary fibrosis (IPF) is the most common type of ILD and has no known cause.

The compounds may be combined with agents which are treatments for IPF and potentially for ILD, including nintedanib and pirfenidone.

Liver cirrhosis has similar causes to ILD and includes, for example, cirrhosis associated with viral hepatitis, schistosomiasis and chronic alcoholism.

Kidney disease may be associated with diabetes, which can damage and scar the kidneys leading to a progressive loss of function, and also hypertensive diseases. Kidney fibrosis may occur at any stage of kidney disease, from acute kidney disease (AKD) post injury and chronic kidney disease (CKD), such as incident CKD and progressive CKD, through to end-stage renal disease (ESRD). Kidney fibrosis can develop as a result of cardiovascular disease such as hypertension or diabetes, both of which place immense strain on kidney function which promotes a fibrotic response. However, kidney fibrosis can also be idiopathic (without a known cause), and certain genetic mitochondrial diseases also present kidney fibrosis manifestations and associated symptoms.

Heart disease may result in scar tissue that can impair the ability of the heart to pump.

Diseases of the eye include, for example, macular degeneration and retinal and vitreal retinopathy, which can impair vision.

In a preferred embodiment, the present invention is directed to the treatment or prevention of idiopathic pulmonary fibrosis (IPF).

In another preferred embodiment, the present invention is directed to the treatment or prevention of kidney fibrosis.

In another preferred embodiment, the present invention is directed to the treatment or prevention of acute kidney injury (AKI), especially in high risk patients. Examples include post-surgical AKI, for example organ transplantation, such as due to ischemia reperfusion injury, delayed graft function; oncology, such as AKI due to chemotherapy; contrast medium-induced nephropathy, such as direct-tubular cytotoxicity, hemodynamic ischemia and osmotic effects; acute interstitial nephritis, such as due to drugs or infection; AKI due to obstruction such as kidney stones; and COVID-19-induced AKI. A particular high risk patient sub-group are those undergoing cardiac surgery, for example, coronary artery bypass graft and/or valve surgery. There are established static risk factors for AKI such as age 65 years or over, insulin dependent diabetes, CKD (adults with an estimated glomerular filtration rate [eGFR] less than 60 ml/min/1.73 $m^2$ are at particular risk), heart failure, liver disease, history of AKI.

In another preferred embodiment, the present invention is directed to the treatment or prevention of acute kidney disease (AKD) or chronic kidney disease (CKD) stemming from such AKI, including, for example, tubulointerstitial fibrosis and diabetic nephropathy.

In another preferred embodiment, the present invention is directed to the treatment or prevention of liver diseases, including, for example, NAFLD, NASH, liver cirrhosis, portal hypertension, acute liver failure, and hepatocellular carcinoma. Liver disease such as NAFLD and NASH may be associated with various metabolic conditions such as metabolic syndrome and Type II diabetes, which also would increase risk for various diabetes associated pathologies, including diabetic retinopathy and peripiheral neuropathies.

The compounds of the invention or pharmaceutical compositions thereof as described herein may be combined with one or more additional agents when used for the treatment or prevention of conditions involving liver disease and metabolic dysfunction, including metformin, sulfonylureas, DPP-4 inhibitors, GLP-1 agonists, PPAR agonists, SGLT2 inhibitors, angiotensin-converting enzyme (ACE) inhibitors and angiotensin II receptor blockers (ARBs).

Leigh syndrome is a rare inherited neurometabolic disorder that affects the central nervous system. This progressive disorder begins in infants between the ages of three months and two years. Rarely, it occurs in teenagers and adults. Leigh syndrome can be caused by mutations in nuclear DNA encoding for mitochondrial proteins, mutations in mitochondrial DNA (maternally inherited Leigh syndrome—MILS), or by deficiencies of an enzyme called pyruvate dehydrogenase located on the short arm of the X Chromosome (X-linked Leigh syndrome). Symptoms of Leigh syndrome usually progress rapidly. The earliest signs may be poor sucking ability, and the loss of head control and motor skills. These symptoms may be accompanied by loss of appetite, vomiting, irritability, continuous crying, and seizures. As the disorder progresses, symptoms may also include generalized weakness, lack of muscle tone, and episodes of lactic acidosis, which can lead to impairment of respiratory and kidney function.

In maternally inherited Leigh syndrome (MILS), genetic mutations in mitochondrial DNA (at a high proportion of >90%) interfere with the energy sources that run cells in an area of the brain that plays a role in motor movements. Genetic mutations in mitochondrial DNA result in a chronic lack of energy in these cells, which in turn affects the central nervous system and causes progressive degeneration of motor functions. When the genetic mutations in mitochondrial DNA that causes MILS are less abundant (less than 90%), the condition is known as neuropathy ataxia and retinitis pigmentosa (NARP). There is also a form of Leigh's disease (called X-linked Leigh's disease) which is the result of mutations in a gene that produces another group of substances that are important for cell metabolism. A further variant of Leigh syndrome exists which is called French Canadian variant, characterized by mutations in a gene called LRPPRC. Similar neurological symptoms are expressed as those for Leigh syndrome, although Liver Steatosis is commonly also observed in the French Canadian variant.

In a preferred embodiment, the present invention is directed to the treatment or prevention of Leigh syndrome or disease, including for example, X-linked Leigh's disease, Leigh syndrome French Canadian variant, and/or the symptoms associated with Leigh's disease.

The compounds may be combined with novel agents which may be used as treatments for mitochondrial disease, including, but not limited to, nicotinamide riboside.

References to 'treatment' includes means to ameliorate, alleviate symptoms, eliminate the causation of the symptoms either on a temporary or permanent basis. The compounds of the invention are useful in the treatment of the diseases disclosed herein in humans and other mammals.

In another embodiment, the invention encompasses prophylactic therapy of the diseases disclosed herein and includes means to prevent or slow the appearance of symptoms of the named disorder or condition. The compounds of the invention are useful in the prevention of the diseases disclosed herein in humans and other mammals.

A patient in need of treatment or prevention may, for example, be a human or other mammal suffering from the condition or at risk of suffering from the condition.

According to a further aspect, the present invention provides a pharmaceutical composition comprising a compound of formula (I) as defined herein, or a pharmaceutically acceptable salt of said compound or tautomer, together with a pharmaceutically acceptable diluent or carrier.

Pharmaceutical compositions of the invention comprise any of the compounds of the invention combined with any pharmaceutically acceptable carrier, adjuvant or vehicle. Examples of pharmaceutically acceptable carriers are known to those skilled in the art and include, but are not limited to, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of the invention or pharmaceutical compositions thereof, as described herein, may be used alone or combined with one or more additional pharmaceutical agents. The compounds may be combined with an additional anti-tumour therapeutic agent, for example, chemotherapeutic drugs or inhibitors of other regulatory proteins. In one embodiment, the additional anti-tumour therapeutic agent is a BH-3 mimetic. In a further embodiment, BH-3 mimetics may be selected from but not limited to one or more of ABT-737, ABT-199, ABT-263, and Obatoclax. In a further embodiment, the additional anti-tumour agent is a chemotherapeutic agent. Chemotherapeutic agents may be selected from but not limited to, olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

For the treatment or prevention of fibrotic disorders, for example, the compounds of the invention or pharmaceutical compositions thereof, as described herein, may be used alone or combined with one or more additional pharmaceutical agents selected from the group consisting of anticholinergic agents, beta-2 mimetics, steroids, PDE-IV inhibitors, p38 MAP kinase inhibitors, NK1 antagonists, LTD4 antagonists, EGFR inhibitors and endothelin antagonists.

In particular, the compounds of the invention or pharmaceutical compositions thereof, as described herein, may be used alone or combined with one or more additional pharmaceutical agents selected from the group consisting of general immunosuppressive drugs, such as a corticosteroid, immunosuppressive or cytotoxic agents, or antifibrotics, such as pirfenidone or a non-specific kinase inhibitor (e.g. nintedanib).

The pharmaceutical compositions of the invention may be administered in any suitably effective manner, such as oral, parenteral, topical, inhaled, intranasal, rectal, intravaginal, ocular and aural. Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolat and silicates, lubricating agents, for example, magnesium stearate and stearic acid, wetting agents, for example, sodium lauryl sulfate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25 (2), 1-14 (2001). Other modified release formulations are described in U.S. Pat. No. 6,106,864.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates, and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by suitable processing, for example, the use of high energy spray-dried dispersions and/or by the use of appropriate formulation techniques, such as the use of solubility-enhancing agents.

Formulations for parenteral administration may be formulated to be immediate and/or modified release. Modified release formulations include delayed, sustained, pulsed, controlled dual, targeted and programmed release.

Pharmaceutical compositions of the present invention also include compositions and methods known in the art for bypassing the blood brain barrier or can be injected directly into the brain. Suitable areas for injection include the cerebral cortex, cerebellum, midbrain, brainstem, hypothalamus, spinal cord and ventricular tissue, and areas of the PNS including the carotid body and the adrenal medulla.

Dosage

The magnitude of an effective dose of a compound will, of course, vary with the nature of the severity of the condition to be treated and the route of administration. The selection of appropriate dosages is within the remit of the physician. The daily dose range is about 10 µg to about 100 mg per kg body weight of a human and non-human animal and in general may be around 10 µg to 30 mg per kg body weight per dose. The above dose may be given from one to three times per day.

For example, oral administration may require a total daily dose of from 5 mg to 1000 mg, such as from 5 to 500 mg, while an intravenous dose may only require from 0.01 to 30 mg/kg body weight, such as from 0.1 to 10 mg/kg, more preferably from 0.1 to 1 mg/kg body weight. The total daily dose may be administered in single or divided doses. The skilled person will also appreciate that, in the treatment or prevention of certain conditions, compounds of the invention may be taken as a single dose on an "as required" basis (i.e. as needed or desired).

Synthetic Methodologies

Compounds of formula (I) may be prepared using methods as described below in the general reaction schemes and the representative examples. Where appropriate, the individual transformations within a scheme may be completed in a different order. The invention is illustrated by the following non-limiting examples in which the following abbreviations and definitions are used. Compounds were characterised by liquid chromatography-mass spectroscopy (LCMS) or $^1$H NMR or both.

According to a further aspect, the present invention provides a process for the preparation of a compound of formula (I)(i) comprising reacting a compound of formula (IV), where Y is OH with an amine of formula (V)(i), where PG is a protecting group, such as BOC or CBZ, to give an amide of formula (III)(i) (Scheme 1). The amide-coupling reaction can be performed using standard methodology, for example by reaction using a coupling reagent such as DCC, HATU, HBTU, EDC or via a mixed anhydride. Alternatively, the acid (IV), where Y is OH, can be converted into the acid chloride (IV), where Y is Cl, using $SOCl_2$, $PCl_3$, or $PCl_5$, which can then be reacted with the amine (V)(i), preferably in a suitable solvent in the presence of a suitable base. Alternatively, the compound (IV), where Y forms the ester, can be reacted directly with the amine (V)(i), preferably in a suitable solvent. The compound of formula (III)(i) may be deprotected using standard methods to give amine (II)(i) which may then be reacted with cyanogen bromide to give the corresponding compound of formula (I)(i).

Scheme 1

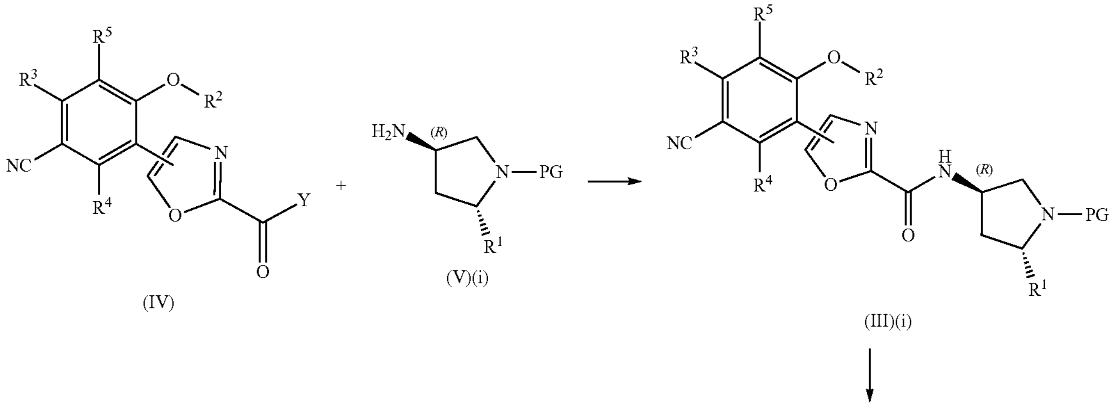

(IV) (V)(i) (III)(i)

-continued

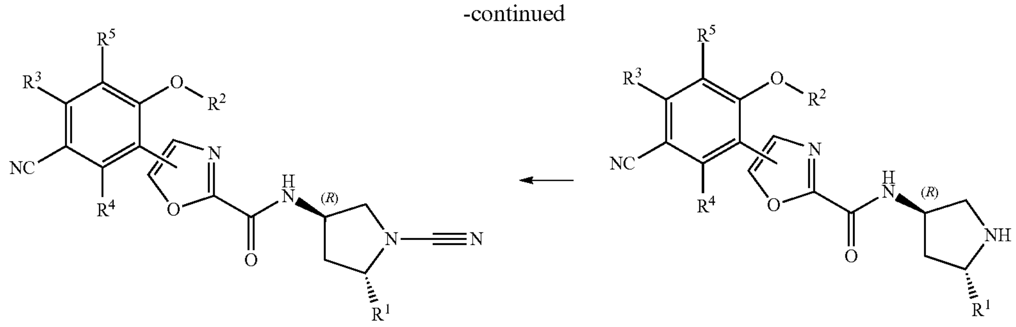

(I)(i) (II)(i)

In a further aspect, the present invention provides a compound, which is selected from formulae (II)(i) and (III)(i):

(II)(i)

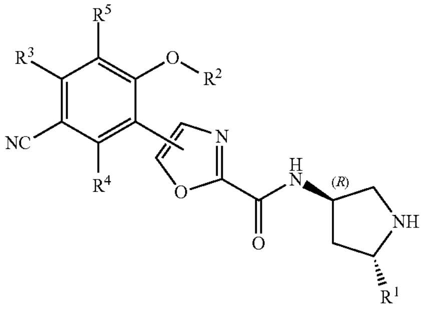

(III)(i)

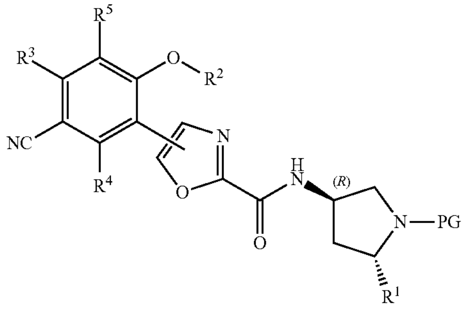

wherein PG is a protecting group, preferably BOC or CBZ, and $R^1$, $R^2$, $R^3$, $R^4$ and $R^5$ are as defined herein for the compound of formula (I) and preferred embodiments thereof, a tautomer thereof, or a salt of said compound or tautomer.

When the compound of formula (I)(i) has formula (IA)(i), formulae (II)(i), (III)(i) and (IV) are (IIA)(i), (IIIA)(i) and (IVA), respectively. When the compound of formula (I)(i) has formula (IB)(i), formulae (II)(i), (III)(i) and (IV) are (IIB)(i), (IIIB)(i) and (IVB)(i), respectively.

According to a further aspect, the present invention provides a process for the preparation of a compound of formula (I)(ii) comprising reacting a compound of formula (IV), where Y is OH with an amine of formula (V)(ii), where PG is a protecting group, such as BOC or CBZ, to give an amide of formula (III)(ii) (Scheme 2). The amide-coupling reaction can be performed using standard methodology, for example by reaction using a coupling reagent such as DCC, HATU, HBTU, EDC or via a mixed anhydride. Alternatively, the acid (IV), where Y is OH, can be converted into the acid chloride (IV), where Y is Cl, using $SOCl_2$, $PCl_3$, or $PCl_5$, which can then be reacted with the amine (V)(ii), preferably in a suitable solvent in the presence of a suitable base. Alternatively, the compound (IV), where Y forms the ester, can be reacted directly with the amine (V)(ii), preferably in a suitable solvent. The compound of formula (III)(ii) may be deprotected using standard methods to give amine (II)(ii) which may then be reacted with cyanogen bromide to give the corresponding compound of formula (I)(ii).

Scheme 2

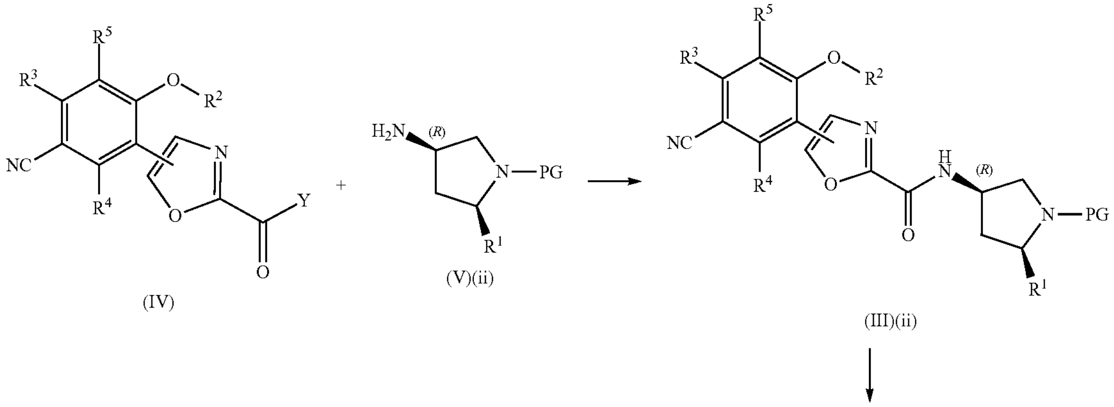

(IV) (V)(ii) (III)(ii)

-continued

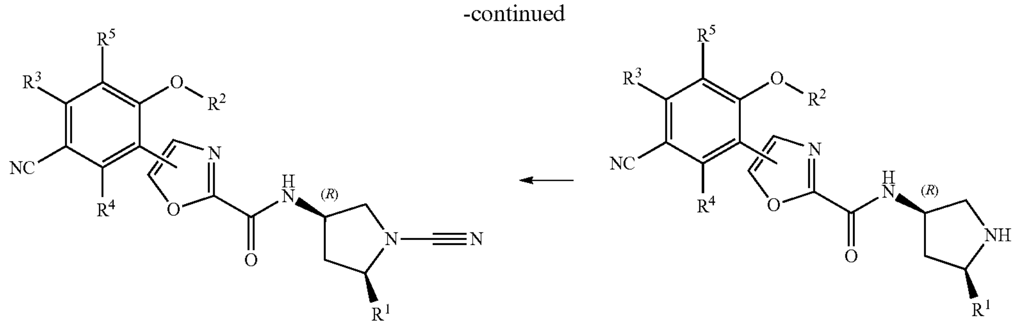

(I)(ii) (II)(ii)

In a further aspect, the present invention provides a compound, which is selected from formulae (II)(ii) and (III)(ii):

(II)(ii)

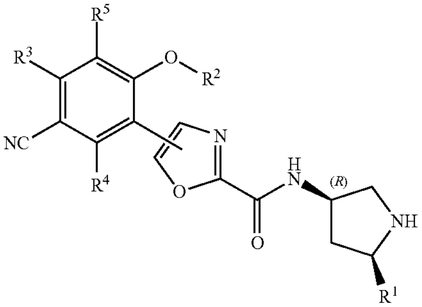

(III)(ii)

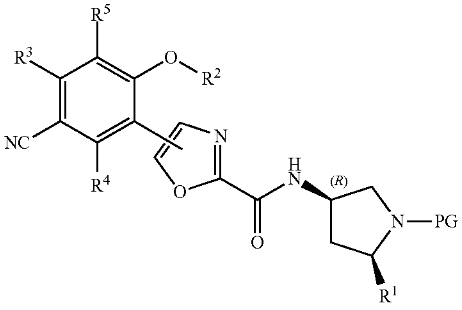

wherein PG is a protecting group, preferably BOC or CBZ, and $R^1$, $R^2$, $R^3$, $R^4$ and $R^5$ are as defined herein for the compound of formula (I) and preferred embodiments thereof, a tautomer thereof, or a salt of said compound or tautomer.

When the compound of formula (I)(ii) has formula (IA)(ii), formulae (II)(ii), (III)(ii) and (IV) are (IIA)(ii), (IIIA)(ii) and (IVA), respectively. When the compound of formula (I)(ii) has formula (IB)(ii), formulae (II)(ii), (III)(ii) and (IV) are (IIB)(ii), (IIIB)(ii) and (IVB)(ii), respectively.

Protecting groups are preferably selected from tert-butyloxycarbonyl (BOC), benzyloxycarbonyl (Cbz), p-methoxybenzyl carbonyl (MeOZ), 9-fluorenylmethyloxycarbonyl (Fmoc), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts), trichloroethoxycarbonyl (Troc), 4-nitrobenzenesulfonyl (Nosyl) and 2-nitrophenylsulfenyl (Nps). Most preferred are BOC and Cbz.

Abbreviations

| | |
|---|---|
| br s | broad singlet (NMR signal) |
| CO | carbon monoxide |
| d | doublet (NMR signal) |
| dba | dibenzylacetone |
| DCM | dichloromethane |
| DMF | N,N-dimethylformamide |
| DMSO | dimethylsulfoxide |
| ES | electrospray |
| EtOAc | ethyl acetate |
| h | hour(s) |
| $H_2$ | hydrogen |
| HPLC | High performance liquid chromatography |
| LCMS | Liquid chromatography - mass spectrometry |
| m | multiplet (NMR signal) |
| MsCl | methanesulfonyl chloride |
| MeCN | acetonitrile |
| MeOH | methanol |
| min | minute(s) |
| $N_2$ | nitrogen |
| NMP | N-methylpyrrolidone |
| rac | racemic |
| rt | room temperature |
| S | singlet (NMR signal) |
| SFC | Supercritical fluid chromatogaphy |
| $SOCl_2$ | thionyl chloride |
| TBD | 1,5,7-triazabicyclo[4.4.0]dec-5-ene |
| TEA | triethylamine |
| TFA | trifluoroacetic acid |
| THF | tetrahydrofuran |
| TsCl | 4-toluenesulfonyl chloride |
| vol | volumes |

LCMS/HPLC/SFC Methods

| Method C | | |
|---|---|---|
| Mobile phase | (A) | 2 mM Ammonium acetate & 0.1% formic acid in water |
| | (B) | 0.1% Formic acid in acetonitrile |
| Instrument | | Waters ACQUITY H Class with PDA and SQ detector |

-continued

| Method C | |
|---|---|
| Column | BEH C18 (50 mm × 2.1 mm) 1.7 μm |
| Flow rate | 0.550 mL/min |
| Column oven temperature | Ambient |
| Run time | 3.0 min |

Gradient

| TIME (min) | Flow Rate (mL/min) | % A | % B |
|---|---|---|---|
| 0.01 | 0.55 | 98 | 2 |
| 0.30 | 0.55 | 98 | 2 |
| 0.60 | 0.55 | 50 | 50 |
| 1.10 | 0.55 | 25 | 75 |
| 2.00 | 0.60 | 0 | 100 |
| 2.70 | 0.60 | 0 | 100 |
| 2.71 | 0.55 | 98 | 2 |
| 3.00 | 0.55 | 98 | 2 |

| Method C1 | | |
|---|---|---|
| Mobile phase | (A) | 2 mM Ammonium acetate & 0.1% formic acid in water |
| | (B) | 0.1% Formic acid in acetonitrile |
| Instrument | | Waters ACQUITY UPLC H Class with PDA and SQ detector |
| Column | | BEH C18 (50 mm × 2.1 mm) 1.7 μm |
| Flow rate | | 0.550 mL/min |
| Column oven temperature | | Ambient |
| Run time | | 2.0 min |

Gradient

| TIME (min) | Flow Rate (mL/min) | % A | % B |
|---|---|---|---|
| 0.00 | 0.55 | 95 | 5 |
| 0.60 | 0.60 | 30 | 70 |
| 0.80 | 0.65 | 10 | 90 |
| 1.10 | 0.65 | 0 | 100 |
| 1.70 | 0.65 | 0 | 100 |
| 1.71 | 0.55 | 95 | 5 |
| 2.00 | 0.55 | 95 | 5 |

| Method C2 | | |
|---|---|---|
| Mobile phase | (A) | 2 mM Ammonium acetate & 0.1% formic acid in water & acetonitrile (90:10) |
| | (B) | 0.1% Formic acid in acetonitrile |
| Instrument | | Waters ACQUITY H Class with PDA and SQ detector |
| Column | | BEH C18 (50 mm × 2.1 mm) 1.7 μm |
| Flow rate | | 0.600 mL/min |
| Column oven temperature | | Ambient |
| Run time | | 1.5 min |

Gradient

| TIME (min) | Flow Rate (mL/min) | % A | % B |
|---|---|---|---|
| 0.01 | 0.600 | 95 | 5 |
| 0.40 | 0.600 | 0 | 100 |
| 0.50 | 0.650 | 0 | 100 |
| 1.30 | 0.700 | 0 | 100 |
| 1.31 | 0.600 | 95 | 5 |
| 1.50 | 0.600 | 95 | 5 |

| Method H | | |
|---|---|---|
| Mobile phase | (A) | 5 mM Ammonium bicarbonate in water |
| | (B) | 100% Acetonitrile |
| Instrument | | Shimadzu Nexera UFLC with 2020 single quadrupole mass detector |
| Column | | Waters X-Bridge C18 (50 × 4.6 mm) 3.5 μm |
| Column oven temperature | | Ambient |
| Flow rate | | 1.0 mL/min |
| Run time | | 8.0 min |

Gradient

| TIME (min) | Flow Rate (mL/min) | % A | % B |
|---|---|---|---|
| 0.01 | 1.0 | 95 | 5 |
| 3.50 | 1.0 | 10 | 90 |
| 4.50 | 1.0 | 5 | 95 |
| 6.00 | 1.0 | 5 | 95 |
| 6.01 | 1.0 | 95 | 5 |
| 8.00 | 1.0 | 95 | 5 |

| Method H1 | | |
|---|---|---|
| Mobile phase | (A) | 5 mM Ammonium bicarbonate in water |
| | (B) | 100% Acetonitrile |
| Instrument | | Shimadzu Nexera UFLC with 2020 single quadrupole mass detector |
| Column | | Waters X-Bridge C18 (50 × 4.6 mm) 3.5 μm |
| Column oven temperature | | Ambient |
| Flow rate | | 1.0 mL/min |
| Run time | | 6.0 min |

Gradient

| TIME (min) | Flow Rate (mL/min) | % A | % B |
|---|---|---|---|
| 0.01 | 1.0 | 95 | 5 |
| 2.80 | 1.0 | 15 | 85 |
| 3.50 | 1.0 | 5 | 95 |
| 5.00 | 1.0 | 5 | 95 |
| 5.01 | 1.0 | 95 | 5 |
| 6.00 | 1.0 | 95 | 5 |

| Method J | | |
|---|---|---|
| Mobile phase | (A) | 2 mM Ammonium acetate & 0.1% formic acid in water |
| | (B) | 0.1% Formic acid in acetonitrile |
| Instrument | | Waters Acquity H Class with PDA and SQ detector |
| Column | | BEH C18 (50 × 2.1 mm) 1.7 μm |
| Column oven temperature | | Ambient |
| Flow rate | | 0.45 mL/min |
| Run time | | 8.0 min |

Gradient

| TIME (min) | Flow Rate (mL/min) | % A | % B |
|---|---|---|---|
| 0.01 | 0.45 | 98 | 2 |
| 0.50 | 0.45 | 98 | 2 |
| 5.00 | 0.45 | 10 | 90 |
| 6.00 | 0.45 | 5 | 95 |
| 7.00 | 0.45 | 5 | 95 |
| 7.01 | 0.45 | 98 | 2 |
| 8.00 | 0.45 | 98 | 2 |

| Method F | | |
|---|---|---|
| Mobile phase | (A) | 10 mM Ammonium acetate in water |
| | (B) | 100 % Acetonitrile |
| Instrument | | Agilent 1290 Infinity RRLC attached with Agilent 6120 mass detector and diode array detector |
| Column | | YMC TRAIT, C18 (150 mm × 4.6 mm), 5 μm |
| Flow rate | | 1.0 mL/min |
| Column oven temperature | | Ambient |
| Run time | | 12.0 min |

Gradient

| TIME (min) | Flow Rate (mL/min) | % A | % B |
|---|---|---|---|
| 0.01 | 1.0 | 90 | 10 |
| 5.00 | 1.0 | 10 | 90 |
| 7.00 | 1.0 | 0 | 100 |
| 11.00 | 1.0 | 0 | 100 |
| 11.01 | 1.0 | 90 | 10 |
| 12.00 | 1.0 | 90 | 10 |

| Method P3 | | |
|---|---|---|
| Mobile phase | (A) | 0.1% v/v (30% v/v Aqueous ammonia) in water |
| | (B) | 0.1% v/v (30% v/v Aqueous ammonia) in acetonitrile |
| Instrument | | Waters e2695 HPLC with PDA detector |
| Column | | X-Bridge C8 (250 × 4.6 mm), 5 μm |
| Column oven temperature | | 25° C. |
| Flow rate | | 1.0 mL/min |
| Run time | | 40.0 min |
| Diluent | | Acetonitrile:Water (8:2 v/v) |

Gradient

| TIME (min) | Flow Rate (mL/min) | % A | % B |
|---|---|---|---|
| 0.0 | 1.0 | 95 | 5 |
| 5.00 | 1.0 | 95 | 5 |
| 10.00 | 1.0 | 70 | 30 |
| 15.00 | 1.0 | 70 | 30 |
| 25.00 | 1.0 | 40 | 60 |
| 30.00 | 1.0 | 10 | 90 |
| 35.00 | 1.0 | 10 | 90 |
| 35.01 | 1.0 | 95 | 5 |
| 40.00 | 1.0 | 95 | 5 |

| Method Y3<br>Method used for analytical chiral SFC | | |
|---|---|---|
| Mobile Phase | (A) | Liquid carbon dioxide |
| | (B) | 0.1% Diethylamine in propan-2-ol: acetonitrile (50:50) |
| Instrument | | Waters SFC investigator and PDA detector |
| Column | | Chiralcel OJ-H (250 × 4.6 mm), 5 μm |
| Flow rate | | 4.0 mL/min |
| Run time | | 7.0 min |

Gradient

| TIME (min) | Flow Rate (mL/min) | % B start | % B end |
|---|---|---|---|
| 0 to 5 | 4.0 | 5 | 5 |
| 5 to 7 | 4.0 | 50 | 50 |

| Method Y4<br>Method used for analytical chiral SFC | | |
|---|---|---|
| Mobile Phase | (A) | Liquid carbon dioxide |
| | (B) | 0.1% Diethylamine in propan-2-ol: acetonitrile (50:50) |
| Instrument | | Waters SFC investigator and PDA detector |
| Column | | Chiralpak IH (250 × 4.6 mm), 5 μm |
| Flow rate | | 4.0 mL/min |
| Run time | | 10.0 min |

Gradient

| TIME (min) | Flow Rate (mL/min) | % B start | % B end |
|---|---|---|---|
| 0 to 5 | 4.0 | 5 | 5 |
| 5 to 10 | 4.0 | 50 | 50 |

| Method Y5<br>Method used for analytical chiral SFC | | |
|---|---|---|
| Mobile Phase | (A) | Liquid carbon dioxide |
| | (B) | 0.1% Diethylamine in propan-2-ol: acetonitrile (50:50) |
| Instrument | | Waters SFC investigator and PDA detector |
| Column | | Chiralpak AD-H (250 × 4.6 mm), 5 μm |
| Flow rate | | 4.0 mL/min |
| Run time | | 10.0 min |

Gradient

| TIME (min) | Flow Rate (mL/min) | % B start | % B end |
|---|---|---|---|
| 0 to 5 | 4.0 | 5 | 5 |
| 5 to 10 | 4.0 | 50 | 50 |

| Method Y6<br>Method used for analytical chiral SFC | | |
|---|---|---|
| Mobile Phase | (A) | Liquid carbon dioxide |
| | (B) | 0.1% Diethylamine in methanol |
| Instrument | | Waters SFC investigator and PDA detector |
| Column | | Chiralcel OJ-H (250 × 4.6 mm), 5 μm |
| Flow rate | | 4.0 mL/min |
| Run time | | 7.0 min |

Gradient

| TIME (min) | Flow Rate (mL/min) | % B start | % B end |
|---|---|---|---|
| 0 to 5 | 4.0 | 5 | 50 |
| 5 to 7 | 4.0 | 50 | 50 |

| Method Y7<br>Method used for analytical chiral SFC | | |
|---|---|---|
| Mobile Phase | (A) | Liquid carbon dioxide |
| | (B) | 0.1% Diethylamine in propan-2-ol:acetonitrile (50:50) |

-continued

| Method Y7 Method used for analytical chiral SFC | | | |
|---|---|---|---|
| Instrument | Waters SFC investigator and PDA detector | | |
| Column | Chiralcel OX-H (250 × 4.6 mm), 5 μm | | |
| Flow rate | 4.0 mL/min | | |
| Run time | 10.0 min | | |
| Gradient | | | |
| TIME (min) | Flow Rate (mL/min) | % B start | % B end |
| 0 to 5 | 4.0 | 5 | 50 |
| 5 to 10 | 4.0 | 50 | 50 |

| Method Y8 Method used for analytical chiral SFC | | | |
|---|---|---|---|
| Mobile | (A) | Liquid carbon dioxide | |
| Phase | (B) | 0.1% Diethylamine in propan-2-ol:acetonitrile (50:50) | |
| Instrument | | Waters SFC investigator and PDA detector | |
| Column | | Chiralpak IC (250 × 4.6 mm), 5 μm | |
| Flow rate | | 4.0 mL/min | |
| Run time | | 10.0 min | |
| Gradient | | | |
| TIME (min) | Flow Rate (mL/min) | % B start | % B end |
| 0 to 5 | 4.0 | 5 | 5 |
| 5 to 10 | 4.0 | 50 | 50 |

| Method Y12 Method used for analytical Chiral SFC | | | |
|---|---|---|---|
| Mobile | (A) | Liquid carbon dioxide | |
| Phase | (B) | 0.1% Diethylamine in propan-2-ol:acetonitrile (50:50) | |
| Instrument | | Waters SFC Investigator and PDA detector | |
| Column | | Chiralcel OJ-H (250 × 4.6 mm), 5 μm | |
| Flow rate | | 4.0 mL/min | |
| Run time | | 8.0 min | |
| Gradient | | | |
| TIME (min) | Flow Rate (mL/min) | % B start | % B end |
| 0 to 5 | 4.0 | 5 | 50 |
| 5 to 8 | 4.0 | 50 | 50 |

| Method Y15 Method used for analytical Chiral HPLC | | | |
|---|---|---|---|
| Mobile | (A) | 0.1% Diethylamine in n-hexane | |
| Phase | (B) | 0.1% Diethylamine in propan-2-ol:acetonitrile (70-30) | |
| Instrument | | Agilent 1260 series HPLC and PDA detector | |
| Column | | Chiralpak IC (250 × 4.6 mm), 5 μm | |
| Flow rate | | 1.0 mL/min | |
| Run time | | 25.0 min | |
| Gradient | | | |
| TIME (min) | Flow Rate (mL/min) | % A start | % B end |
| 0.01 | 1.0 | 80 | 20 |
| 5.00 | 1.0 | 45 | 55 |
| 10.00 | 1.0 | 30 | 70 |
| 15.00 | 1.0 | 30 | 70 |
| 20.00 | 1.0 | 80 | 20 |
| 25.00 | 1.0 | 80 | 20 |

| Method Y16 Method used for analytical Chiral SFC | | | |
|---|---|---|---|
| Mobile | (A) | Liquid carbon dioxide | |
| Phase | (B) | 0.1% Diethylamine in methanol | |
| Instrument | | Waters SFC Investigator and PDA detector | |
| Column | | Chiralpak IB-N (250 × 4.6 mm), 5 μm | |
| Flow rate | | 4.0 mL/min | |
| Run time | | 8.0 min | |
| Gradient | | | |
| TIME (min) | Flow Rate (mL/min) | % B start | % B end |
| 0 to 5 | 4.0 | 5 | 50 |
| 5 to 8 | 4.0 | 50 | 50 |

Intermediate A

Ethyl 5-(5-cyano-2-cyclopropoxyphenyl)oxazole-2-carboxylate

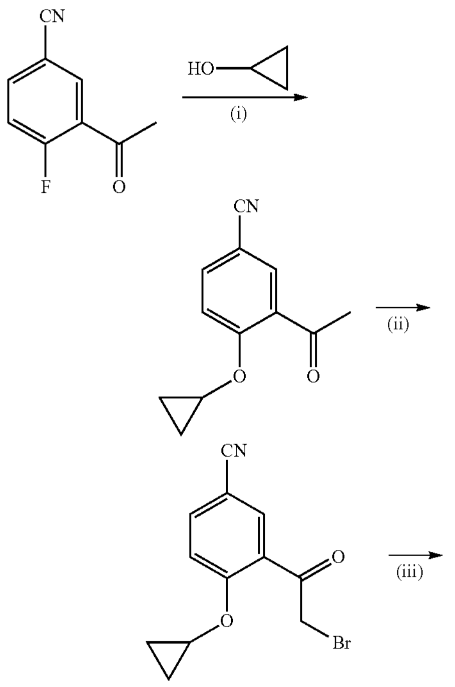

-continued

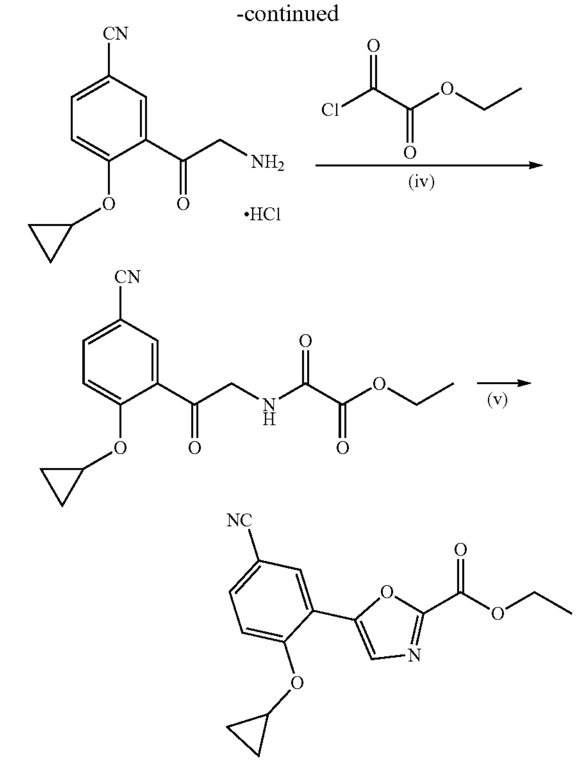

(i) NaH, THF, 0° C., 2 h; (ii) phenyl trimethylammonium tribromide, THF, 0° C. to rt, 16 h; (iii) $NaN(CHO)_2$, MeCN, 70° C., 1 h, then conc. HCl, 70° C., 16 h; (iv) $K_2CO_3$, DCM, 0° C. to rt, 2 h; (v) $POCl_3$, 100° C., 7 h.

Step (i)

3-Acetyl-4-cyclopropoxybenzonitrile

This reaction was performed in triplicate. To a stirred solution of cyclopropanol (CAS 16545-68-9, from Synthonix, 0.71 g, 12.27 mmol) in THF (6 mL) was added NaH (60% in oil, 0.49 g, 12.27 mmol) in portions at 0° C. and stirred for 30 min. A solution of 3-acetyl-4-fluorobenzonitrile (CAS 267875-54-7, from Combi-blocks, 1.0 g, 6.13 mmol) in THF (4 mL) was added dropwise at 0° C. and the mixture was stirred at 0° C. for 2 h. The reaction mixture was combined with two more identical batches and then poured into ice-cold water (500 mL) and extracted with EtOAc (2×500 mL). The combined organic phases were dried over $Na_2SO_4$ and concentrated under reduced pressure. The residue was purified by flash column chromatography (silica gel, 12% EtOAc in n-hexanes) to yield to afford 3-acetyl-4-cyclopropoxybenzonitrile (3.18 g, 15.82 mmol, 85% yield).

LCMS: m/z not supportive; $^1H$ NMR (400 MHz, DMSO-$d_6$) δ ppm: 8.05 (dd, J=8.8, 2.4 Hz, 1H), 7.96 (d, J=2.0 Hz, 1H), 7.64 (d, J=8.8 Hz, 1H), 4.13-4.17 (m, 1H), 2.50 (s, 3H), 0.81-0.93 (m, 4H).

Step (ii)

3-(2-Bromoacetyl)-4-cyclopropoxybenzonitrile

To a stirred solution of 3-acetyl-4-cyclopropoxybenzonitrile (3.18 g, 15.82 mmol) in THF (40 mL) was added phenyl trimethylammonium tribromide (5.94 g, 15.82 mmol) at 0° C. The mixture was slowly warmed to rt and stirred for 16 h, then poured into water (200 mL) and extracted with EtOAc (2×200 mL). The combined organic phases were dried over $Na_2SO_4$ and concentrated under reduced pressure to afford 3-(2-bromoacetyl)-4-cyclopropoxybenzonitrile (4.3 g, 15.41 mmol, 97% yield). This crude material was used directly in the next step.

LCMS: Method F, 6.61 min; MS: ES+: 297.0, 299.0 (M+18).

Step (iii)

4-Cyclopropoxy-3-glycylbenzonitrile hydrochloride

To a stirred solution of 3-(2-bromoacetyl)-4-cyclopropoxybenzonitrile (4.30 g, 15.41 mmol) in acetonitrile (43 mL) was added sodium diformylamide (1.75 g, 18.49 mmol) and heated at 70° C. for 3 h. The reaction mixture was cooled to rt and concentrated under reduced pressure. The residue was diluted with MeOH (43 mL) and conc. HCl (4.3 mL). The mixture was further heated at 70° C. for 16 h then allowed to cool to rt. The mixture was concentrated under reduced pressure, and the residue was stirred with isopropyl alcohol (25 mL) to form a precipitate. The solid was collected by filtration under reduced pressure to afford 4-cyclopropoxy-3-glycylbenzonitrile hydrochloride (5.0 g, quantitative yield).

LCMS: Method C, 1.30 min; MS: ES+: 217.4.

Step (iv)

Ethyl 2-((2-(5-cyano-2-cyclopropoxyphenyl)-2-oxoethyl)amino)-2-oxoacetate

To a stirred solution of 4-cyclopropoxy-3-glycylbenzonitrile HCl salt (5.0 g, 19.80 mmol) in DCM (50 mL) was added $K_2CO_3$ (10.92 g, 79.2 mmol) at 0° C. Ethyl oxalyl chloride (5.4 g, 4.43 mL, 39.60 mmol) was added dropwise at 0° C. The mixture was allowed to warm to rt, stirred for 2 h, then poured into water (500 mL) and extracted with DCM (2×300 mL). The combined organic phases were dried over $Na_2SO_4$ and concentrated under reduced pressure to afford ethyl 2-((2-(5-cyano-2-cyclopropoxy phenyl)-2-oxoethyl)amino)-2-oxoacetate (5.0 g, quantitative yield).

LCMS: Method C, 1.52 min; MS: ES+316.9.

Step (v)

Ethyl 5-(5-cyano-2-cyclopropoxyphenyl)oxazole-2-carboxylate

A stirred solution of ethyl 2-((2-(5-cyano-2-cyclopropoxyphenyl)-2-oxoethyl)amino)-2-oxoacetate (5.0 g, 15.81 mmol) in $POCl_3$ (50 mL, 10 vol) was heated at 100° C. for 7 h. The mixture was cooled to rt, poured into ice-cold water (500 mL) and extracted with EtOAc (2×200 mL). The combined organic phases were dried over $Na_2SO_4$ and concentrated under reduced pressure. The residue was suspended in MeOH (40 mL) and stirred at −78° C. for 15 min. The solid was collected by filtration under reduced pressure to afford ethyl 5-(5-cyano-2-cyclopropoxyphenyl)oxazole-2-carboxylate (1.0 g, 3.35 mmol, 21% yield over three steps). LCMS: Method C, 1.77 min; MS: ES+: 299.5.

Intermediate B

Ethyl 5-(5-cyano-2-methoxyphenyl)oxazole-2-carboxylate

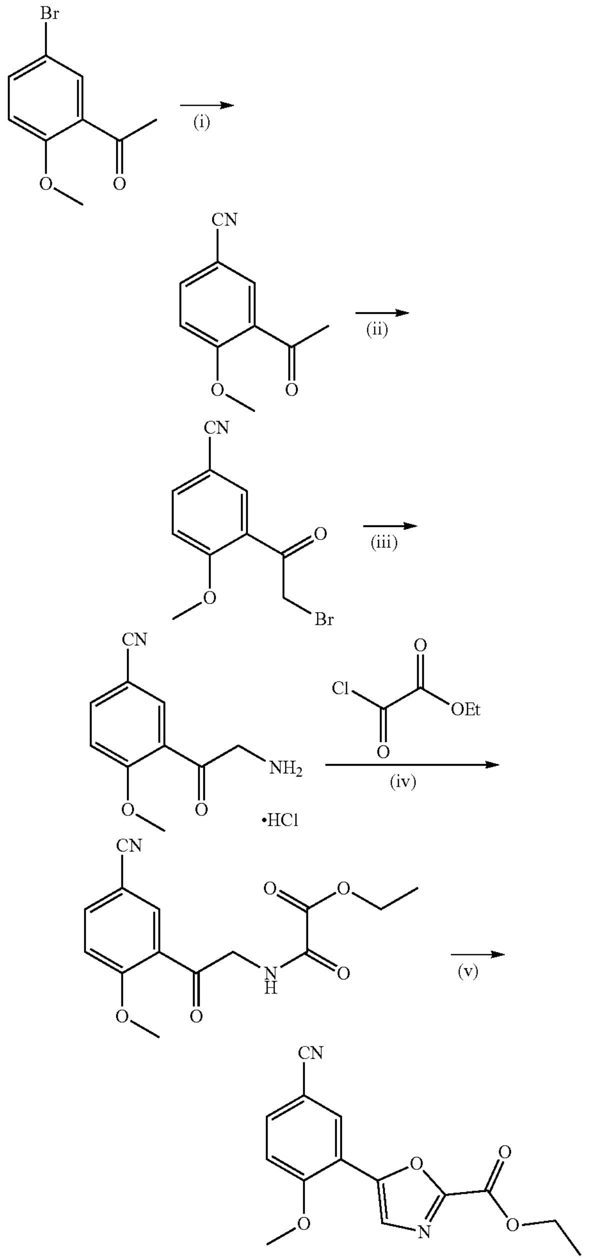

(i) $Zn(CN)_2$, Zn dust, $PdCl_2$(dppf)·DCM complex, DMA, 120° C., 16 h; (ii) pyridinium tribromide, THF, 0° C. to rt, 16 h; (iii) $NaN(CHO)_2$, MeCN, 80° C., 5 h, then conc. HCl, 80° C., 16 h; (iv) $K_2CO_3$, DCM, 0° C. to rt, 4 h; (v) $POCl_3$, 100° C., 16 h.

Step (i)

3-Acetyl-4-methoxybenzonitrile

To a stirred solution of 1-(5-bromo-2-methoxyphenyl) ethan-1-one (CAS 16740-73-1, from Combi-blocks, 60.0 g, 261.89 mmol) in DMA (600 mL) was added zinc cyanide (92.25 g, 785.67 mmol) and zinc dust (17.22 g, 261.89 mmol) at rt. The mixture was degassed with $N_2$ gas for 30 min, followed by addition of [1,1'-Bis(diphenylphosphino) ferrocene]dichloropalladium(II), complex with DCM (10.69 g, 13.09 mmol). The mixture was heated at 120° C. for 16 h. The mixture was allowed to cool to rt, filtered through Celite Hyflow™, the filtrate was poured into ice-cold water (800 mL), and extracted with EtOAc (2×1000 mL). The combined organic phases were washed with ice-cold water (4×1000 mL), dried over $Na_2SO_4$ and concentrated under reduced pressure. The residue was purified by column chromatography (60-120 #silica gel, 15% EtOAc in n-hexanes) to yield 3-acetyl-4-methoxybenzonitrile (40.0 g, 228.57 mmol, 87% yield).

LCMS: Method C, 1.52 min; MS: ES+: 176.08.

Step (ii)

3-(2-Bromoacetyl)-4-methoxybenzonitrile

To a stirred solution of 3-acetyl-4-methoxybenzonitrile (7.20 g, 41.14 mmol) in THF (72 mL) was added pyridinium tribromide (14.47 g, 45.25 mmol) at 0° C. The mixture was slowly warmed to rt and stirred for 16 h, then poured into water (400 mL) and extracted with EtOAc (2×400 mL). The combined organic phases were dried over $Na_2SO_4$ and concentrated under reduced pressure to afford 3-(2-bromo-acetyl)-4-methoxybenzonitrile (13.0 g, quantitative yield). This crude material was used directly in the next step.

Step (iii)

3-Glycyl-4-methoxybenzonitrile hydrochloride

To a stirred solution of 3-(2-bromoacetyl)-4-methoxybenzonitrile (10.5 g, 41.51 mmol) in acetonitrile (105 mL) was added sodium diformylamide (5.91 g, 62.26 mmol) and the mixture was heated at 80° C. for 8 h. The reaction mixture was cooled to rt, concentrated under reduced pressure and the residue was diluted with MeOH (105 mL) and conc. HCl (10.5 mL). The mixture was further heated at 80° C. for 16 h then allowed to cool to rt. The mixture was concentrated under reduced pressure, and the residue was stirred with isopropyl alcohol (40 mL) to form a precipitate, which was collected by filtration under reduced pressure to afford 3-glycyl-4-methoxybenzonitrile hydrochloride (9.0 g, 39.73 mmol, 95% yield).

LCMS: Method C2, 0.40 min; MS: ES+: 191.0.

Step (iv)

Ethyl 2-((2-(5-cyano-2-methoxyphenyl)-2-oxoethyl) amino)-2-oxoacetate

To a stirred solution of 3-glycyl-4-methoxybenzonitrile hydrochloride HCl salt (9.0 g, 39.73 mmol) in DCM (90 mL) was added $K_2CO_3$ (21.93 g, 158.92 mmol) at 0° C. Ethyl oxalyl chloride (10.84 g, 8.89 mL, 79.46 mmol) was added dropwise at 0° C. The mixture was allowed to warm to rt and stirred for 4 h. The mixture was poured into water (900 mL) and extracted with DCM (2×500 mL). The combined organic phases were dried over $Na_2SO_4$ and concentrated under reduced pressure to afford ethyl 2-((2-(5-cyano-2-methoxyphenyl)-2-oxoethyl)amino)-2-oxoacetate (9.0 g, 31.03 mmol, 78% yield).

LCMS: Method C, 1.34 min; MS: ES+291.1.

Step (v)

Ethyl 5-(5-cyano-2-methoxyphenyl)oxazole-2-carboxylate

A stirred solution of ethyl 2-((2-(5-cyano-2-methoxyphenyl)-2-oxoethyl)amino)-2-oxoacetate (1.2 g, 4.14 mmol) in $POCl_3$ (12 mL, 10 vol) was heated at 100° C. for 2 h. The mixture was cooled to rt, poured into ice-cold water (200 mL) and extracted with EtOAc (3×100 mL). The combined organic phases were washed with saturated $NaHCO_3$ solution (3×100 mL), dried over $Na_2SO_4$ and concentrated under reduced pressure. The residue was purified by flash column chromatography (silica gel, 32% EtOAc in n-hexanes) to afford ethyl 5-(5-cyano-2-methoxyphenyl)oxazole-2-carboxylate (0.60 g, 2.20 mmol, 53% yield).

LCMS: Method C, 1.53 min; MS: ES+: 272.6.

Intermediate C

Ethyl 5-(5-bromo-2-(trifluoromethoxy)phenyl)oxazole-2-carboxylate

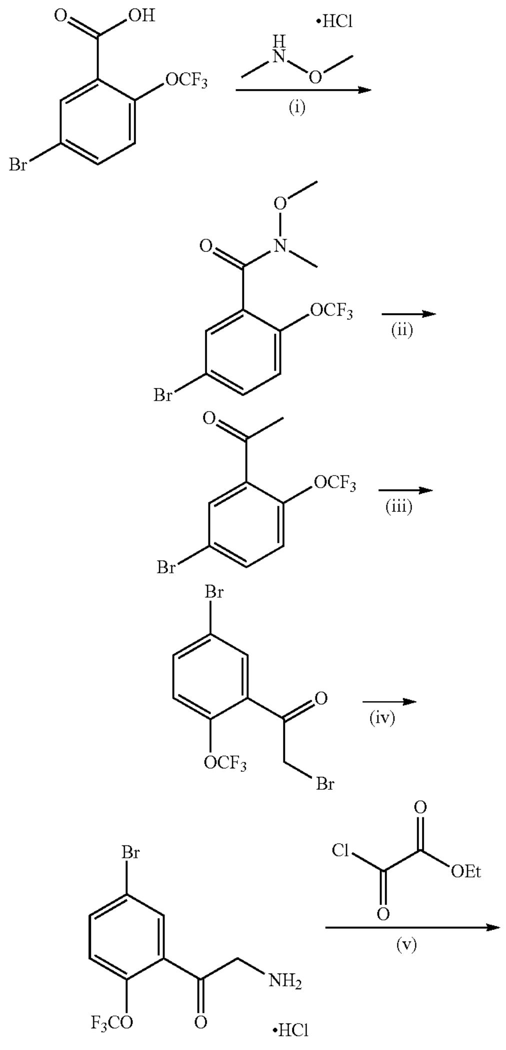

-continued

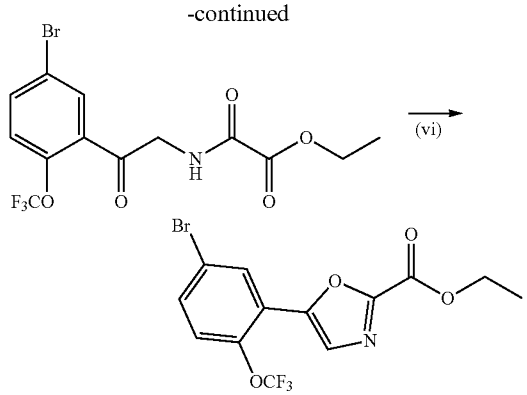

(i) HATU, DIPEA, THF, 0° C. to rt, 3 h; (ii) methyl magnesium bromide, THF, −10° C. to 0° C., 4 h; (iii) phenyl trimethylammonium tribromide, MeCN, 0° C. to rt, 9 h; (iv) $NaN(CHO)_2$, MeCN, 80° C., 1 h, then conc. HCl, 80° C., 3 h; (v) $K_2CO_3$, DCM, 0° C. to rt, 3 h; (vi) $POCl_3$, 110° C., 16 h.

Step (i)

5-Bromo-N-methoxy-N-methyl-2-(trifluoromethoxy)benzamide

To a stirred solution of 5-bromo-2-(trifluoromethoxy)benzoic acid (CAS 403646-47-9, from Combi-blocks, 10.0 g, 35.08 mmol) in THF (100 mL) was added DIPEA (13.57 g, 17.9 mL, 105.25 mmol) and HATU (20.0 g, 52.62 mmol) in portions at 0° C. After 30 min, N,O-dimethylhydroxylamine HCl (4.45 g, 45.61 mmol) was added at 0° C. The mixture was slowly warmed to rt and stirred for 3 h, then poured into ice-cold water (300 mL) and extracted with EtOAc (3×150 mL). The combined organic phases were dried over $Na_2SO_4$ and concentrated under reduced pressure to yield 5-bromo-N-methoxy-N-methyl-2-(trifluoromethoxy)benzamide (12.2 g, quantitative yield). This crude material was used directly in the next step.

LCMS: Method C, 1.69 min; MS: ES+: 327.8, 329.8.

Step (ii)

1-(5-Bromo-2-(trifluoromethoxy)phenyl)ethan-1-one

To a stirred solution of 5-bromo-N-methoxy-N-methyl-2-(trifluoromethoxy)benzamide (12.2 g, 37.31 mmol) in THF (130 mL) was added methyl magnesium bromide (3M in diethyl ether, 24.9 mL, 74.62 mmol) dropwise at −10° C. The mixture was slowly warmed to 0° C. and stirred for 4 h, then poured into saturated $NH_4Cl$ solution (300 mL) and extracted with EtOAc (3×200 mL). The combined organic phases were dried over $Na_2SO_4$ and concentrated under reduced pressure to afford 1-(5-bromo-2-(trifluoromethoxy)phenyl)ethan-1-one (10.0 g, quantitative yield). This crude material was used directly in the next step.

LCMS: Method C, m/z not supportive; $^1H$ NMR (400 MHz, $CDCl_3$) δ ppm: 7.92 (s, 1H), 7.67-7.71 (m, 1H), 7.24 (d, J=8.0 Hz, 1H), 2.62 (s, 3H).

Step (iii)

2-Bromo-1-(5-bromo-2-(trifluoromethoxy)phenyl)ethan-1-one

To a stirred solution of 1-(5-bromo-2-(trifluoromethoxy)phenyl)ethan-1-one (10.0 g, 35.46 mmol) in acetonitrile (100 mL) was added phenyl trimethylammonium tribromide (13.33 g, 35.46 mmol) in portions at 0° C. The mixture was slowly warmed to rt and stirred for 9 h, then poured into water (200 mL) and extracted with EtOAc (3x100 mL). The combined organic phases were dried over $Na_2SO_4$ and concentrated under reduced pressure. The residue was purified by column chromatography (silica gel, 5% EtOAc in n-hexanes) to yield 2-bromo-1-(5-bromo-2-(trifluoromethoxy)phenyl)ethan-1-one (11.5 g, 31.95 mmol, 91% yield over three steps).

LCMS: m/z not supportive; $^1H$ NMR (400 MHz, $CDCl_3$) δ ppm: 7.93 (s, 1H), 7.73 (dd, J=8.8, 2.4 Hz, 1H), 7.25 (d, J=8.0 Hz, 1H), 4.45 (s, 2H).

Step (iv)

2-Amino-1-(5-bromo-2-(trifluoromethoxy)phenyl) ethan-1-one hydrochloride

To a stirred solution of 2-bromo-1-(5-bromo-2-(trifluoromethoxy)phenyl)ethan-1-one (10.0 g, 27.78 mmol) in acetonitrile (100 mL) was added sodium diformylamide (5.28 g, 55.58 mmol) and mixture was heated at 80° C. for 1 h. The mixture was cooled to rt, concentrated under reduced pressure, and the residue was diluted with MeOH (100 mL) and conc. HCl (10.0 mL). The mixture was heated at 80° C. for 3 h, then allowed to cool to rt. The mixture was concentrated under reduced pressure, the residue was stirred with diethyl ether (4x30 mL) to form a precipitate, which was collected by filtration under reduced pressure to afford 2-amino-1-(5-bromo-2-(trifluoromethoxy)phenyl)ethan-1-one hydrochloride (9.41 g, quantitative yield). LCMS: Method C, 1.65 min; MS: ES+: 299.9, 301.9.

Step (v)

Ethyl 2-((2-(5-bromo-2-(trifluoromethoxy)phenyl)-2-oxoethyl)amino)-2-oxoacetate

To a stirred solution of 2-amino-1-(5-bromo-2-(trifluoromethoxy)phenyl)ethan-1-one HCl salt (9.4 g, 28.19 mmol) in DCM (94 mL) was added $K_2CO_3$ (11.67 g, 84.56 mmol) at 0° C. Ethyl oxalyl chloride (5.77 g, 4.73 mL, 42.28 mmol) was added dropwise at 0° C. The mixture was allowed to warm to rt, stirred for 3 h, then poured into water (150 mL) and extracted with DCM (3x120 mL). The combined organic phases were dried over $Na_2SO_4$ and concentrated under reduced pressure to afford ethyl 2-((2-(5-bromo-2-(trifluoromethoxy)phenyl)-2-oxoethyl)amino)-2-oxoacetate (3.4 g, 8.56 mmol, 31% yield over two steps).

LCMS: Method C, 2.09 min; MS: ES− 396.0, 398.0.

Step (vi)

Ethyl 5-(5-bromo-2-(trifluoromethoxy)phenyl)oxazole-2-carboxylate

A stirred solution of ethyl 2-((2-(5-bromo-2-(trifluoromethoxy)phenyl)-2-oxoethyl)amino)-2-oxoacetate (3.4 g, 8.56 mmol) in $POCl_3$ (17 mL, 5 vol) was heated at 110° C. for 16 h. The mixture was cooled to rt, poured into ice-cold water (250 mL) and extracted with EtOAc (3x100 mL). The combined organic phases were washed with saturated $NaHCO_3$ solution (3x100 mL), dried over $Na_2SO_4$ and concentrated under reduced pressure. The residue was purified by flash column chromatography (silica gel, 18% EtOAc in n-hexanes) to afford ethyl 5-(5-bromo-2-(trifluoromethoxy)phenyl)oxazole-2-carboxylate (1.3 g, 3.43 mmol, 40% yield).

LCMS: Method C, 2.39 min; MS: ES+: 379.8, 381.8.

Intermediate D

Ethyl 5-(5-cyano-4-fluoro-2-methoxyphenyl)oxazole-2-carboxylate

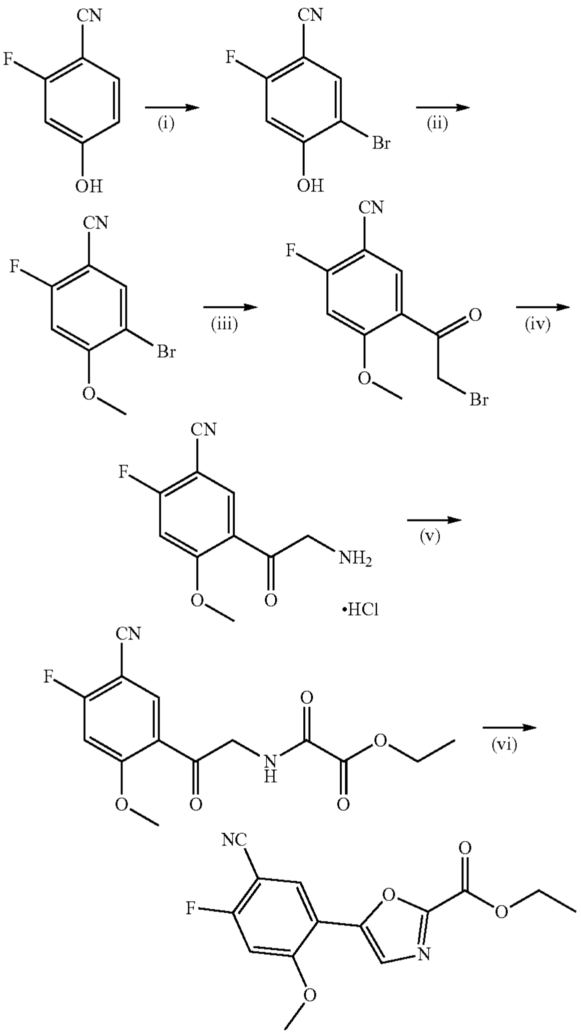

(i) triflic acid, NBS, MeCN, −30° C. to rt, 18 h; (ii) $K_2CO_3$, MeI, DMF, 0° C. to rt, 3 h; (iii) tributyl(1-ethoxyvinyl)tin, $PdCl_2(PPh_3)_2$, 1,4-dioxan, 100° C., 3 h, then NBS, THF:water, 0° C., 10 min; (iv) $NaN(CHO)_2$, MeCN, 80° C., 2 h, then conc. HCl, 80° C., 16 h; (v) ethyl chlorooxoacetate, $K_2CO_3$, DCM, 0° C. to rt, 2 h; (vi) $POCl_3$, 100° C., 5 h.

Step (i)

5-Bromo-2-fluoro-4-hydroxybenzonitrile

To a stirred solution of 2-fluoro-4-hydroxybenzonitrile (CAS 82380-18-5, from Combi-blocks, 8.0 g, 58.39 mmol) in acetonitrile (80 mL) was added triflic acid (10.51 g, 6.18 mL, 70.07 mmol) dropwise at −30° C. After 10 min, N-bromosuccinimide (10.39 g, 58.39 mmol) was added portionwise at −30° C. The mixture was slowly warmed to rt and stirred for 18 h, then poured into saturated $NaHCO_3$ solution (150 mL) and extracted with EtOAc (2x150 mL). The combined organic phases were dried over $Na_2SO_4$ and concentrated under reduced pressure to yield 5-bromo-2- fluoro-4-hydroxybenzonitrile (5.08 g, 23.63 mmol, 40% yield). This crude material was used directly in the next step.

LCMS: Method C, 1.58 min; MS: ES−: 214.0, 216.0.

Step (ii)

5-Bromo-2-fluoro-4-methoxybenzonitrile

To a stirred solution of 5-bromo-2-fluoro-4-hydroxybenzonitrile (5.08 g, 23.63 mmol) in DMF (30 mL) was added $K_2CO_3$ (6.52 g, 47.26 mmol) at 0° C. After 10 min, methyl iodide (5.03 g, 2.21 mL, 35.45 mmol) was added dropwise at 0° C. The mixture was slowly warmed to rt and stirred for 3 h, then poured into water (100 mL) and extracted with EtOAc (2×100 mL). The combined organic phases were dried over $Na_2SO_4$ and concentrated under reduced pressure. The residue was purified by column chromatography (silica gel, 2% EtOAc in n-hexanes) to yield 5-bromo-2-fluoro-4-methoxybenzonitrile (5.70 g, quantitative yield).

LCMS: m/z not supportive; $^1$H NMR (400 MHz, DMSO-$d_6$) δ ppm: 8.30 (d, J=7.2 Hz, 1H), 7.46 (d, J=12.0 Hz, 1H), 4.01 (s, 3H).

Step (iii)

5-(2-Bromoacetyl)-2-fluoro-4-methoxybenzonitrile

A stirred solution of 5-bromo-2-fluoro-4-methoxybenzonitrile (5.70 g, 24.89 mmol) and tributyl(1-ethoxyvinyl)tin (CAS 97674-02-7, from Combi-blocks, 13.46 g, 37.34 mmol) in 1,4-dioxane (70 mL) was degassed with $N_2$ for 15 min, followed by addition of bis(triphenylphosphine)palladium(II) dichloride (0.87 g, 1.24 mmol) at rt. The mixture was heated at 100° C. for 3 h. The mixture was cooled to 0° C. and THF:water (2:1, 120 mL) was added. N-bromosuccinimide (8.85 g, 49.78 mmol) was added at 0° C. The mixture was stirred at 0° C. for 10 min, then poured into water (100 mL) and extracted with EtOAc (2×100 mL). The combined organic phases were dried over $Na_2SO_4$ and concentrated under reduced pressure. The residue was purified by column chromatography (silica gel, 2% EtOAc in n-hexanes) to afford 5-(2-bromoacetyl)-2-fluoro-4-methoxybenzonitrile (6.3 g, 23.25 mmol, 98% yield over two steps).

LCMS: m/z not supportive; $^1$H NMR (400 MHz, DMSO-$d_6$) δ ppm: 8.27 (dd, J=7.6, 2.4 Hz, 1H), 7.54 (dd, J=12.0, 2.4 Hz, 1H), 4.84 (s, 2H), 4.05 (s, 3H).

Step (iv)

2-Fluoro-5-glycyl-4-methoxybenzonitrile hydrochloride

To a stirred solution of 5-(2-bromoacetyl)-2-fluoro-4-methoxybenzonitrile (6.30 g, 23.25 mmol) in acetonitrile (65 mL) was added sodium diformylamide (25.85 g, 27.9 mmol) and the mixture was heated at 80° C. for 2 h. The mixture was cooled to rt, concentrated under reduced pressure and the residue was diluted with MeOH (65 mL) and conc. HCl (6.5 mL). The mixture was heated at 80° C. for 16 h, then allowed to cool to rt. The mixture was concentrated under reduced pressure, and the residue was stirred with isopropyl alcohol (100 mL) to form a precipitate which was collected by filtration under reduced pressure to afford 2-fluoro-5-glycyl-4-methoxybenzonitrile hydrochloride (5.3 g, quantitative yield).

LCMS: Method H, 1.96 min; MS: ES+: 209.1.

Step (v)

Ethyl 2-((2-(5-cyano-4-fluoro-2-methoxyphenyl)-2-oxoethyl)amino)-2-oxoacetate To a stirred solution of 2-fluoro-5-glycyl-4-methoxybenzonitrile HCl salt (5.30 g, 21.67 mmol) in DCM (60 mL) was added $K_2CO_3$ (11.96 g, 86.68 mmol) at 0° C. Ethyl oxalyl chloride (5.89 g, 4.83 mL, 43.34 mmol) was added dropwise at 0° C. The mixture was allowed to warm to rt, stirred for 2 h, then poured into water (150 mL) and extracted with EtOAc (2×150 mL). The combined organic phases were dried over $Na_2SO_4$ and concentrated under reduced pressure to afford ethyl 2-((2-(5-cyano-4-fluoro-2-methoxyphenyl)-2-oxoethyl)amino)-2-oxoacetate (4.20 g, 13.63 mmol, 58% yield over two steps).

LCMS: Method C, 1.50 min; MS: ES+309.4.

Step (vi)

Ethyl 5-(5-cyano-4-fluoro-2-methoxyphenyl)oxazole-2-carboxylate

A stirred solution of ethyl 2-((2-(5-cyano-4-fluoro-2-methoxyphenyl)-2-oxoethyl)amino)-2-oxoacetate (4.2 g, 13.63 mmol) in $POCl_3$ (42 mL, 10 vol) was heated at 100° C. for 5 h. The mixture was cooled to rt, poured into ice-cold water (100 mL) and extracted with EtOAc (2×150 mL). The combined organic phases were washed with saturated $NaHCO_3$ solution (2×100 mL), dried over $Na_2SO_4$ and concentrated under reduced pressure. The residue was suspended in MeOH (30 mL) and stirred at −78° C. for 15 min. The solid was collected by filtration under reduced pressure to afford ethyl 5-(5-cyano-4-fluoro-2-methoxyphenyl)oxazole-2-carboxylate (1.60 g, 5.51 mmol, 40% yield).

LCMS: Method C, 1.63 min; MS: ES+: 291.2.

Example 1

5-(5-Cyano-2-cyclopropoxyphenyl)-N-((3R,5R)-1-cyano-5-methylpyrrolidin-3-yl)oxazole-2-carboxamide

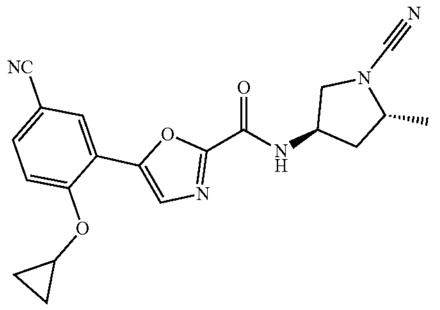

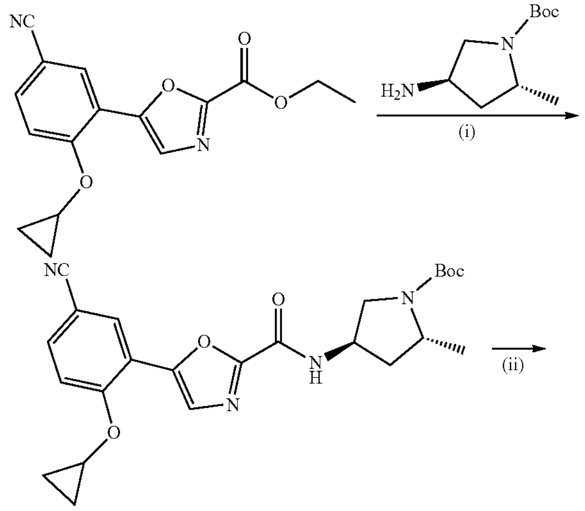

-continued

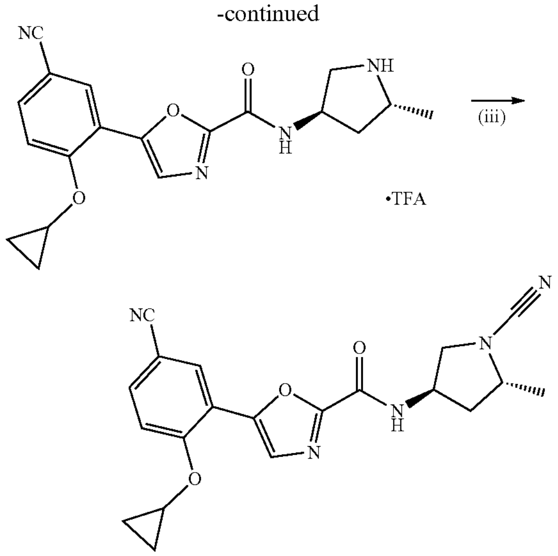

(i) TBD, THF, 0° C. to rt; (ii) TFA, DCM, 0° C. to rt; (iii) $K_2CO_3$, CNBr, THF, 0° C. to rt.

Step (i)

tert-Butyl (2R,4R)-4-(5-(5-cyano-2-cyclopropoxyphenyl)oxazole-2-carboxamido)-2-methylpyrrolidine-1-carboxylate To a stirred solution of ethyl 5-(5-cyano-2-cyclopropoxyphenyl)oxazole-2-carboxylate (0.60 g, 2.01 mmol) and tert-butyl (2R,4R)-4-amino-2-methylpyrrolidine-1-carboxylate (CAS 348165-63-9, 0.60 g, 3.02 mmol) in THF (10 mL) was added TBD (0.42 g, 3.02 mmol) in portions at 0° C. The mixture was warmed to rt and stirred for 1 h, then poured into water (70 mL) and extracted with EtOAc (2×70 mL). The combined organic phases were dried over anhydrous $Na_2SO_4$ and concentrated under reduced pressure. The residue was purified by flash column chromatography (silica gel, 30% EtOAc in n-hexanes) to yield tert-butyl (2R,4R)-4-(5-(5-cyano-2-cyclopropoxyphenyl)oxazole-2-carboxamido)-2-methylpyrrolidine-1-carboxylate (0.32 g, 0.71 mmol, 35% yield).

LCMS: Method C, 1.86 min; MS: ES− 451.4.

Step (ii)

5-(5-Cyano-2-cyclopropoxyphenyl)-N-((3R,5R)-5-methylpyrrolidin-3-yl)oxazole-2-carboxamide To a stirred solution of tert-butyl (2R,4R)-4-(5-(5-cyano-2-cyclopropoxyphenyl)oxazole-2-carboxamido)-2-methylpyrrolidine-1-carboxylate (0.31 g, 0.68 mmol) in DCM (7 mL) was added TFA (0.93 mL, 3 vol) dropwise at 0° C. The mixture was allowed to warm to rt and stirred for 45 min, then concentrated under reduced pressure to yield 5-(5-cyano-2-cyclopropoxyphenyl)-N-((3R,5R)-5-methylpyrrolidin-3-yl)oxazole-2-carboxamide TFA salt (0.3 g, 0.64 mmol, 94% yield).

LCMS: Method C, 1.38 min; MS: ES+353.3.

Step (iii)

5-(5-Cyano-2-cyclopropoxyphenyl)-N-((3R,5R)-1-cyano-5-methylpyrrolidin-3-yl)oxazole-2-carboxamide To a stirred solution of 5-(5-cyano-2-cyclopropoxyphenyl)-N-((3R,5R)-5-methylpyrrolidin-3-yl)oxazole-2-carboxamide TFA salt (0.3 g, 0.64 mmol) in THF (8 mL) was added $K_2CO_3$ (0.27 g, 1.93 mmol) at rt and the mixture was stirred for 10 min. Cyanogen bromide (0.07 g, 0.64 mmol) was added at 0° C. and the mixture was stirred at rt for 45 min, then poured into water (70 mL) and extracted with EtOAc (2×70 mL). The combined organic phases were dried over $Na_2SO_4$ and concentrated under reduced pressure. The residue was purified by flash column chromatography (silica gel, 40% EtOAc in n-hexanes) to yield 5-(5-cyano-2-cyclopropoxyphenyl)-N-((3R,5R)-1-cyano-5-methylpyrrolidin-3-yl)oxazole-2-carboxamide (0.1 g, 0.27 mmol, 42% yield).

LCMS: Method H, 2.96 min; MS: ES+378.0; $^1H$ NMR (400 MHz, DMSO-$d_6$) δ ppm: 9.36 (d, J=6.4 Hz, 1H), 8.27 (s, 1H), 7.98 (d, J=8.4 Hz, 1H), 7.68-7.70 (m, 2H), 4.51-4.53 (m, 1H), 4.21-4.23 (m, 1H), 3.89-3.95 (m, 1H), 3.77-3.81 (m, 1H), 3.43-3.46 (m, 1H), 2.16-2.18 (m, 1H), 1.76-1.83 (m, 1H), 1.26 (d, J=6.4 Hz, 3H), 0.92 (s, 4H). Chiral SFC: Method Y5, 5.18 min.

Example 2

5-(5-Cyano-2-cyclopropoxyphenyl)-N-((3R,5S)-1-cyano-5-(methoxymethyl)pyrrolidin-3-yl)oxazole-2-carboxamide

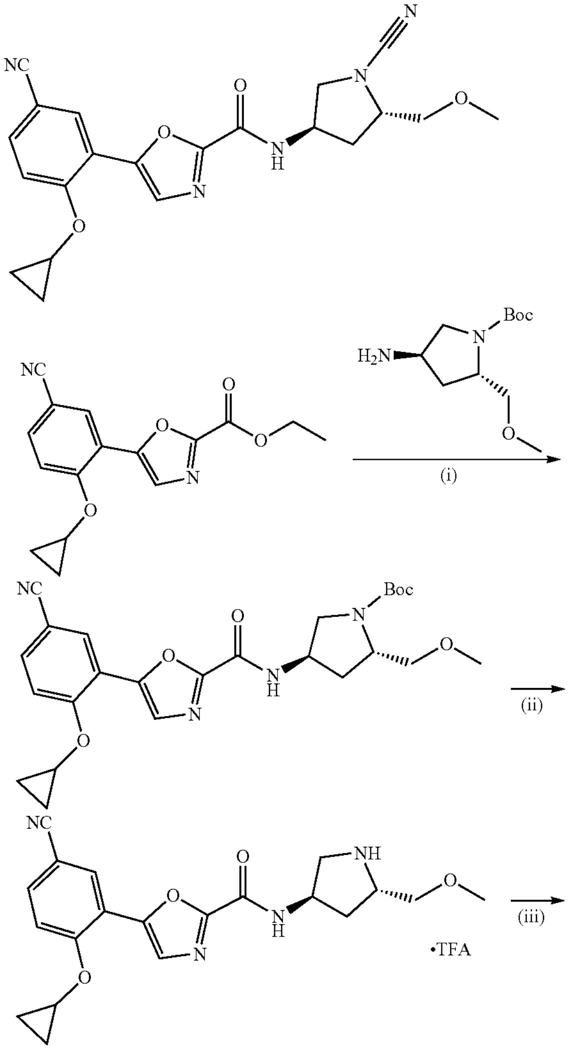

-continued

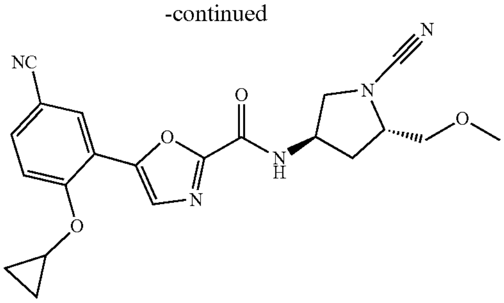

(i) TBD, THF, 0° C. to rt; (ii) TFA, DCM, 0° C. to rt; (iii) $K_2CO_3$, CNBr, THF, 0° C. to rt.

Step (i)

tert-Butyl (2S,4R)-4-(5-(5-cyano-2-cyclopropoxy-phenyl)oxazole-2-carboxamido)-2-(methoxymethyl) pyrrolidine-1-carboxylate To a stirred solution of ethyl 5-(5-cyano-2-cyclopropoxy-phenyl)oxazole-2-carboxylate (0.50 g, 1.67 mmol) and tert-butyl-(2S,4R)-4-amino-2-(methoxymethyl)pyrrolidine-1-carboxylate (CAS 1207853-53-9, 0.46 g, 2.01 mmol) in THF (8 mL) was added TBD (0.35 g, 2.51 mmol) in portions at 0° C. The mixture was warmed to rt and stirred for 3 h, then poured into water (100 mL) and extracted with EtOAc (2×80 mL). The combined organic phases were dried over anhydrous $Na_2SO_4$ and concentrated under reduced pressure. The residue was purified by flash column chromatography (silica gel, 55% EtOAc in n-hexanes) to yield tert-butyl (2S,4R)-4-(5-(5-cyano-2-cyclopropoxyphenyl) oxazole-2-carboxamido)-2-(methoxymethyl)pyrrolidine-1-carboxylate (0.32 g, 0.66 mmol, 39% yield).

LCMS: Method C1, 1.35 min; MS: ES+483.4.

Step (ii)

5-(5-Cyano-2-cyclopropoxyphenyl)-N-((3R,5S)-5-(methoxymethyl)pyrrolidin-3-yl)oxazole-2-carboxamide To a stirred solution of tert-butyl (2S,4R)-4-(5-(5-cyano-2-cyclopropoxyphenyl)oxazole-2-carboxamido)-2-(methoxymethyl)pyrrolidine-1-carboxylate (0.32 g, 0.66 mmol) in DCM (8 mL) was added TFA (0.96 mL, 3 vol) dropwise at 0° C. The mixture was allowed to warm to rt and stirred for 1 h, then concentrated under reduced pressure to yield 5-(5-cyano-2-cyclopropoxyphenyl)-N-((3R,5S)-5-(methoxymethyl)pyrrolidin-3-yl)oxazole-2-carboxamide TFA salt (0.32 g, 0.64 mmol, 97% yield).

LCMS: Method C1, 1.06 min; MS: ES+383.4.

Step (iii)

5-(5-Cyano-2-cyclopropoxyphenyl)-N-((3R,5S)-1-cyano-5-(methoxymethyl)pyrrolidin-3-yl)oxazole-2-carboxamide To a stirred solution of 5-(5-cyano-2-cyclopropoxyphenyl)-N-((3R,5S)-5-(methoxymethyl)pyrrolidin-3-yl)oxazole-2-carboxamide TFA salt (0.32 g, 0.64 mmol) in THF (8 mL) was added $K_2CO_3$ (0.27 g, 1.93 mmol) at rt and stirred for 10 min. Cyanogen bromide (0.07 g, 0.64 mmol) was added at 0° C. The mixture was stirred at rt for 1 h, then poured into water (80 mL) and extracted with EtOAc (2×80 mL). The combined organic phases were dried over $Na_2SO_4$ and concentrated under reduced pressure. The residue was purified by flash column chromatography (silica gel, 70% EtOAc in n-hexanes) to yield 5-(5-cyano-2-cyclopropoxyphenyl)-N-((3R,5S)-1-cyano-5-(methoxymethyl)pyrrolidin-3-yl)oxazole-2-carboxamide (0.10 g, 0.24 mmol, 38% yield).

LCMS: Method H, 2.94 min; MS: ES+408.2; $^1H$ NMR (400 MHz, DMSO-$d_6$) δ ppm: 9.32 (d, J=6.4 Hz, 1H), 8.26 (d, J=1.6 Hz, 1H), 7.98 (d, J=8.8 Hz, 1H), 7.69-7.70 (m, 2H), 4.47-4.59 (m, 1H), 4.19-4.27 (m, 1H), 4.00-4.10 (m, 1H), 3.70-3.74 (m, 1H), 3.39-3.51 (m, 3H), 3.36 (s, 3H), 2.11-2.18 (m, 1H), 1.98-2.03 (m, 1H), 0.92 (s, 4H). Chiral SFC: Method Y3, 3.56 min.

Step (iii) Alternative Synthesis 5-(5-Cyano-2-cyclopropoxyphenyl)-N-((3R,5S)-1-cyano-5-(methoxymethyl)pyrrolidin-3-yl)oxazole-2-carboxamide Under $N_2$ atmosphere, to a stirred solution of 5-(5-cyano-2-cyclopropoxyphenyl)-N-((3R,5S)-5-(methoxymethyl)pyrrolidin-3-yl)oxazole-2-carboxamide TFA salt (600.0 g, 1209.67 mmol) in THF (6 L), was added $K_2CO_3$ (500.80 g, 3629.01 mmol) at rt under $N_2$ atmosphere and stirred for 15 to 20 min. A solution of cyanogen bromide (153.87 g, 1451.60 mmol) in THF (1.2 L) was added dropwise at 0° C. The mixture was allowed to warm to rt and stirred for 1 h at rt. The progress of the reaction was monitored by TLC (mobile phase: 50% EtOAc in n-hexanes, product $R_f$ 0.05; 10% MeOH/DCM product $R_f$ 0.4. The mixture was quenched with water (3 L) and extracted with EtOAc (3×6 L). The combined organic phases were washed with brine solution (1.5 L), dried over anhydrous $Na_2SO_4$ and concentrated under reduced pressure to yield crude 5-(5-cyano-2-cyclopropoxyphenyl)-N-((3R,5S)-1-cyano-5-(methoxymethyl)pyrrolidin-3-yl)oxazole-2-carboxamide (505 g). The crude material (505 g) was suspended in IPA (5 L, 10 vol) and heated at 80° C. to obtain a clear solution. The mixture was slowly allowed to cool to rt and then at 0° C. to form crystalline solid which was collected by filtration under reduced pressure, washed with cold IPA (505 mL) and dried under vacuum at 50° C. to yield 5-(5-cyano-2-cyclopropoxyphenyl)-N-((3R,5S)-1-cyano-5-(methoxymethyl)-pyrrolidin-3-yl)oxazole-2-carboxamide as a white crystalline solid (400.0 g, 982.80 mmol).

The material from the IPA recrystallisation (400 g) was suspended in IPA (10 L, 25 vol), charcoal (100 g) was added, and the mixture was heated at 80° C. for 1 h. The hot mixture was filtered through Celite Hyflow™ and washed with hot IPA (800 mL, 2 vol). The filtrate was slowly allowed to cool to rt and then at 0° C. to form a crystalline solid which was collected by suction filtration, washed with cold IPA (400 L, 1 vol) and dried under vacuum at 50° C. to yield 5-(5-cyano-2-cyclopropoxyphenyl)-N-((3R,5S)-1-cyano-5-(methoxymethyl)pyrrolidin-3-yl)oxazole-2-carboxamide as white crystalline solid (320.0 g, 786.24 mmol, 63% yield).

LCMS: Method H1, 2.81 min, MS: ES+408.2; HPLC: Method P3, 24.22 min; Chiral HPLC: Method Y, 28.97 min; $^1H$ NMR (400 MHz, DMSO-$d_6$) δ ppm: 9.29 (d, J=6.8 Hz, 1H), 8.22 (d, J=2.0 Hz, 1H), 7.95 (dd, J=8.8, 2.4 Hz, 1H), 7.67 (d, J=8.8 Hz, 1H), 7.65 (s, 1H), 4.48-4.58 (m, 1H), 4.18-4.22 (m, 1H), 4.01-4.07 (m, 1H), 3.70-3.74 (m, 1H), 3.40-3.51 (m, 3H), 3.35 (s, 3H), 2.12-2.18 (m, 1H), 1.97-2.03 (m, 1H), 0.88-0.96 (n, 4H); Chiral HPLC: Method Y15, 15.11 min; 99.8% ee; HPLC: Method Y26, 27.87 min; DSC peak temperature (melt)=132.7° C.; high resolution MS: ES-406.1521 (calculated exact mass 407.1594). XRPD data in the table below were prepared on a Bruker AXS D8 Advance: Cu,kα: Kα1(Å): 1.540598; Kα2(Å): 1.544426; Kα2/Kα1=0.50.

| | Angle | d value | Intensity |
|---|---|---|---|
| 1 | 6.1019 | 14.4829 | 16.4 |
| 2 | 9.1518 | 9.6553 | 4.7 |
| 3 | 9.9967 | 8.8411 | 2.6 |
| 4 | 10.3379 | 8.5500 | 3.5 |
| 5 | 10.9032 | 8.1080 | 10.8 |
| 6 | 11.3251 | 7.8069 | 13.1 |
| 7 | 12.2208 | 7.2366 | 100.0 |
| 8 | 13.4827 | 6.5620 | 17.1 |
| 9 | 14.2466 | 6.2118 | 23.8 |
| 10 | 14.7766 | 5.9902 | 22.5 |
| 11 | 15.3381 | 5.7722 | 45.2 |
| 12 | 15.7537 | 5.6208 | 41.9 |
| 13 | 15.9125 | 5.5651 | 28.3 |
| 14 | 16.6015 | 5.3356 | 10.7 |
| 15 | 17.5713 | 5.0433 | 29.2 |
| 16 | 18.2473 | 4.8579 | 22.0 |
| 17 | 18.8069 | 4.7146 | 30.6 |
| 18 | 19.5552 | 4.5359 | 9.7 |
| 19 | 20.0896 | 4.4164 | 53.5 |
| 20 | 20.7701 | 4.2732 | 13.1 |
| 21 | 21.3811 | 4.1525 | 13.7 |
| 22 | 21.8959 | 4.0560 | 22.1 |
| 23 | 22.7766 | 3.9011 | 45.7 |
| 24 | 23.5065 | 3.7816 | 26.8 |
| 25 | 23.9799 | 3.7080 | 38.9 |
| 26 | 24.1583 | 3.6810 | 32.8 |
| 27 | 24.8866 | 3.5749 | 32.0 |
| 28 | 25.0830 | 3.5475 | 26.4 |
| 29 | 25.5443 | 3.4843 | 17.3 |
| 30 | 26.1307 | 3.4075 | 15.6 |
| 31 | 26.4530 | 3.3667 | 14.6 |
| 32 | 27.1747 | 3.2789 | 10.7 |
| 33 | 27.4419 | 3.2476 | 9.4 |
| 34 | 27.8223 | 3.2040 | 9.2 |
| 35 | 28.3928 | 3.1409 | 7.7 |
| 36 | 28.7031 | 3.1077 | 6.8 |
| 37 | 29.4677 | 3.0288 | 12.0 |
| 38 | 29.8598 | 2.9899 | 11.1 |
| 39 | 30.9607 | 2.8860 | 12.4 |
| 40 | 32.3735 | 2.7632 | 6.9 |
| 41 | 32.8863 | 2.7213 | 7.2 |
| 42 | 33.5633 | 2.6679 | 5.9 |
| 43 | 34.3472 | 2.6088 | 6.2 |
| 44 | 35.8828 | 2.5006 | 6.5 |
| 45 | 37.2616 | 2.4112 | 6.6 |
| 46 | 38.7662 | 2.3210 | 5.2 |
| 47 | 39.5119 | 2.2789 | 5.4 |

Alternative Recrystallisation 5-(5-Cyano-2-cyclopropoxyphenyl)-N-((3R,5S)-1-cyano-5-(methoxymethyl)pyrrolidin-3-yl)oxazole-2-carboxamide Crude 5-(5-cyano-2-cyclopropoxyphenyl)-N-((3R,5S)-1-cyano-5-(methoxymethyl)pyrrolidin-3-yl)oxazole-2-carboxamide (134.4 g, 98.9% purity by LC) was suspended in ethanol (1340 mL, 10 vol) and heated to 55 to 65° C. to form a brown solution. The mixture was allowed to cool to 40 to 45° C. and seed material was added (135 mg) from an analogous smaller scale batch, and the mixture was stirred at 40 to 45° C. for 30 min. The mixture was cooled to rt and stirred overnight. The beige suspension was filtered and the solid was collected, washed with ethanol (2×260 mL), the filter cake was pulled dry then dried at 60° C. overnight to yield 5-(5-cyano-2-cyclopropoxyphenyl)-N-((3R,5S)-1-cyano-5-(methoxy-methyl)pyrrolidin-3-yl)oxazole-2-carboxamide as an off-white solid (116.2 g, 86% yield from crude).

MS: ES+408.2; $^1$H NMR (400 MHz, $CDCl_3$) δ ppm: 8.24 (d, J=2.0 Hz, 1H), 7.66 (dd, J=8.8, 2.0 Hz, 1H), 7.56 (s, 1H), 7.47 (d, J=8.4 Hz, 1H), 4.68-4.75 (m, 1H), 3.97-4.00 (m, 2H), 3.83-3.85 (m, 1H), 3.60-3.66 (m, 1H), 3.45-3.53 (m, 2H), 3.42 (s, 3H), 2.24-2.32 (m, 1H), 2.09-2.15 (m, 1H), 0.89-1.02 (m, 4H); residual solvents by NMR=EtOH (2260 ppm); HPLC purity 99.6%; DSC peak temperature (melt) =86.96° C.

Example 2 was formulated as an aqueous suspension containing 0.1% (w/v) Tween-80 and 0.5% (w/v) hydroxy-propyl-methylcellulose.

Example 3

5-(5-Cyano-2-cyclopropoxyphenyl)-N-((3R,5S)-1-cyano-5-(fluoromethyl)pyrrolidin-3-yl)oxazole-2-carboxamide

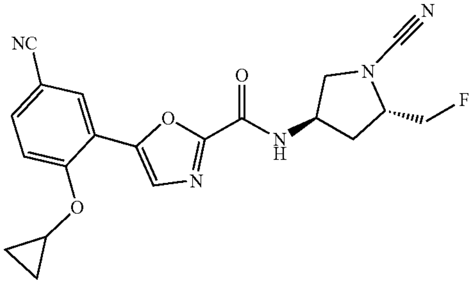

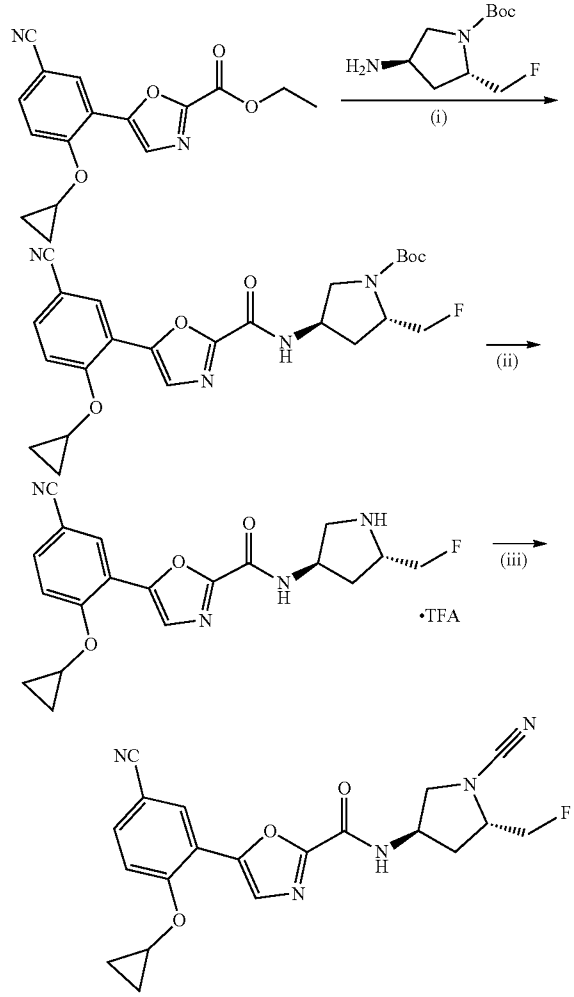

(i) TBD, THF, 0° C. to rt; (ii) TFA, DCM, 0° C. to rt; (iii) $K_2CO_3$, CNBr, THF, 0° C. to rt.

Step (i)

tert-Butyl (2S,4R)-4-(5-(5-cyano-2-cyclopropoxy-phenyl)oxazole-2-carboxamido)-2-(fluoromethyl) pyrrolidine-1-carboxylate To a stirred solution of ethyl 5-(5-cyano-2-cyclopropoxy-phenyl)oxazole-2-carboxylate (0.15 g, 0.50 mmol) and tert-butyl (2S,4R)-4-amino-2-(fluoromethyl)pyrrolidine-1-carboxylate (CAS 1207853-03-9, from Angene, 0.11 g, 0.50 mmol) in THF (4 mL) was added TBD (0.07 g, 0.50 mmol) in portions at 0° C. The mixture was warmed to rt and stirred for 8 h, then poured into water (40 mL) and extracted with EtOAc (2×50 mL). The combined organic phases were dried over anhydrous $Na_2SO_4$ and concentrated under reduced pressure. The residue was purified by flash column chromatography (silica gel, 51% EtOAc in n-hexanes) to yield tert-butyl (2S,4R)-4-(5-(5-cyano-2-cyclopropoxyphenyl) oxazole-2-carboxamido)-2-(fluoromethyl)pyrrolidine-1-carboxylate (0.09 g, 0.19 mmol, 37% yield). LCMS: Method C, 1.76 min; MS: ES− 469.1.

Step (ii)

5-(5-Cyano-2-cyclopropoxyphenyl)-N-((3R,5S)-5-(fluoromethyl)pyrrolidin-3-yl)oxazole-2-carboxamide To a stirred solution of tert-butyl (2S,4R)-4-(5-(5-cyano-2-cyclopropoxyphenyl)oxazole-2-carboxamido)-2-(fluoromethyl)pyrrolidine-1-carboxylate (0.09 g, 0.19 mmol) in DCM (5 mL) was added TFA (0.9 mL, 10 vol) dropwise at 0° C. The mixture was allowed to warm to rt and stirred for 1 h, then concentrated under reduced pressure to yield 5-(5-cyano-2-cyclopropoxyphenyl)-N-((3R,5S)-5-(fluoromethyl)pyrrolidin-3-yl)oxazole-2-carboxamide TFA salt (0.16 g, quantitative yield).

LCMS: Method C, 1.35 min; MS: ES− 368.9.

Step (iii)

5-(5-Cyano-2-cyclopropoxyphenyl)-N-((3R,5S)-1-cyano-5-(fluoromethyl)pyrrolidin-3-yl)oxazole-2-carboxamide To a stirred solution of 5-(5-cyano-2-cyclopropoxyphenyl)-N-((3R,5S)-5-(fluoromethyl)pyrrolidin-3-yl)oxazole-2-carboxamide TFA salt (0.15 g, 0.32 mmol) in THF (5 mL) was added $K_2CO_3$ (0.13 g, 0.96 mmol) at rt and the mixture was stirred for 10 min. Cyanogen bromide (0.03 g, 0.32 mmol) was added at 0° C. The mixture was stirred at rt for 1 h, then poured into water (40 mL) and extracted with EtOAc (2×40 mL). The combined organic phases were dried over $Na_2SO_4$ and concentrated under reduced pressure. The residue was purified by flash column chromatography (silica gel, 69% EtOAc in n-hexanes) to yield 5-(5-cyano-2-cyclopropoxyphenyl)-N-((3R,5S)-1-cyano-5-(fluoromethyl)-pyrrolidin-3-yl)oxazole-2-carboxamide (0.01 g, 0.03 mmol, 16% yield over two steps).

LCMS: Method H, 2.96 min; MS: ES+396.1; $^1H$ NMR (400 MHz, DMSO-$d_6$) δ ppm: 9.39 (d, J=6.8 Hz, 1H), 8.25 (s, 1H), 7.98 (d, J=7.2 Hz, 1H), 7.68-7.70 (m, 2H), 4.41-4.69 (m, 3H), 4.10-4.26 (m, 2H), 3.61-3.80 (m, 1H), 3.43-3.53 (m, 1H), 2.12-2.25 (m, 1H), 1.95-2.07 (m, 1H), 0.92 (s, 4H). Chiral SFC: Method Y4, 4.96 min.

Example 4

5-(5-Cyano-2-methoxyphenyl)-N-((3R,5R)-1-cyano-5-methylpyrrolidin-3-yl)oxazole-2-carboxamide

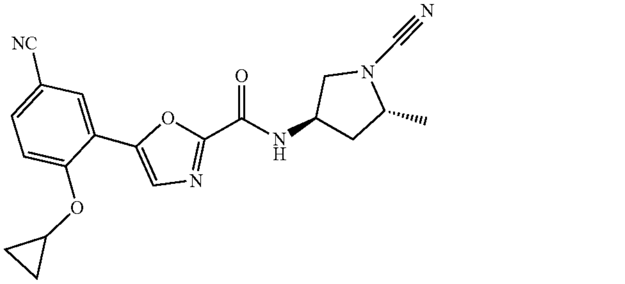

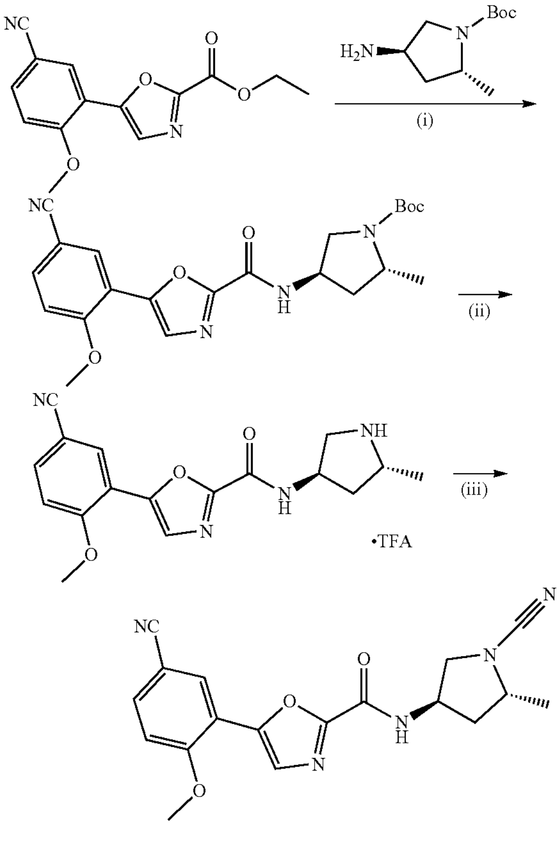

(i) TBD, THF, 0° C. to rt; (ii) TFA, DCM, 0° C. to rt; (iii) $K_2CO_3$, CNBr, THF, 0° C. to rt.

Step (i)

tert-Butyl (2R,4R)-4-(5-(5-cyano-2-methoxyphenyl) oxazole-2-carboxamido)-2-methylpyrrolidine-1-carboxylate To a stirred solution of ethyl 5-(5-cyano-2-methoxyphenyl)oxazole-2-carboxylate (0.5 g, 1.84 mmol) and tert-butyl (2R,4R)-4-amino-2-methylpyrrolidine-1-carboxylate (CAS 348165-63-9, 0.37 g, 1.84 mmol) in THF (10 mL) was added TBD (0.38 g, 2.76 mmol) in portions at 0° C. The mixture was warmed to rt and stirred for 2 h, then poured into water (100 mL) and extracted with EtOAc (2×70 mL). The combined organic phases were dried over anhydrous $Na_2SO_4$ and concentrated under reduced pressure. The residue was purified by flash column chromatography (silica gel, 30% EtOAc in n-hexanes) to yield tert-butyl (2R,4R)-4-(5-(5-cyano-2-methoxyphenyl)oxazole-2-carboxamido)-2-methyl pyrrolidine-1-carboxylate (0.30 g, 0.70 mmol, 38% yield).

LCMS: Method C, 1.61 min; MS: ES− 425.1.

Step (ii)

5-(5-Cyano-2-methoxyphenyl)-N-((3R,5R)-5-methylpyrrolidin-3-yl)oxazole-2-carboxamide To a stirred solution of tert-butyl (2R,4R)-4-(5-(5-cyano-2-methoxyphenyl)oxazole-2-carboxamido)-2-methyl pyrrolidine-1-carboxylate (0.30 g, 0.70 mmol) in DCM (6 mL) was added TFA (0.9 mL, 3 vol) dropwise at 0° C. The mixture was allowed to warm to rt and stirred for 1 h, then concentrated under reduced pressure to yield 5-(5-cyano-2-methoxyphenyl)-N-((3R,5R)-5-methylpyrrolidin-3-yl)oxazole-2-carboxamide TFA salt (0.30 g, 0.68 mmol, 97% yield).

LCMS: Method C, 1.22 min; MS: ES+327.1.

Step (iii)

5-(5-Cyano-2-methoxyphenyl)-N-((3R,5R)-1-cyano-5-methylpyrrolidin-3-yl)oxazole-2-carboxamide To a stirred solution of 5-(5-cyano-2-methoxyphenyl)-N-((3R,5R)-5-methylpyrrolidin-3-yl)oxazole-2-carboxamide TFA salt (0.30 g, 0.68 mmol) in THF (7 mL) was added $K_2CO_3$ (0.28 g, 2.04 mmol) at rt and stirred for 10 min. Cyanogen bromide (0.07 g, 0.68 mmol) was added at 0° C. The mixture was stirred at rt for 1 h, then poured into water (50 mL) and extracted with EtOAc (2×50 mL). The combined organic phases were dried over $Na_2SO_4$ and concentrated under reduced pressure. The residue was purified by flash column chromatography (silica gel, 1% MeOH in DCM) to yield 5-(5-cyano-2-methoxyphenyl)-N-((3R,5R)-1-cyano-5-methylpyrrolidin-3-yl)oxazole-2-carboxamide (0.10 g, 0.28 mmol, 42% yield).

LCMS: Method H, 2.73 min; MS: ES+352.2; $^1H$ NMR (400 MHz, DMSO-$d_6$) δ ppm: 9.35 (d, J=6.8 Hz, 1H), 8.25 (s, 1H), 7.95 (d, J=7.2 Hz, 1H), 7.84 (s, 1H), 7.41 (d, J=8.4 Hz, 1H), 4.47-4.57 (m, 1H), 4.08 (s, 3H), 3.89-3.94 (m, 1H), 3.76-3.80 (m, 1H), 3.42-3.49 (m, 1H), 2.16-2.20 (m, 1H), 1.76-1.83 (m, 1H), 1.26 (d, J=6.4 Hz, 3H). Chiral SFC: Method Y6, 3.76 min.

Example 5

5-(5-Cyano-2-methoxyphenyl)-N-((3R,5S)-1-cyano-5-(methoxymethyl)pyrrolidin-3-yl)oxazole-2-carboxamide

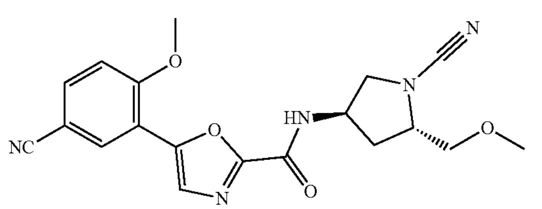

-continued

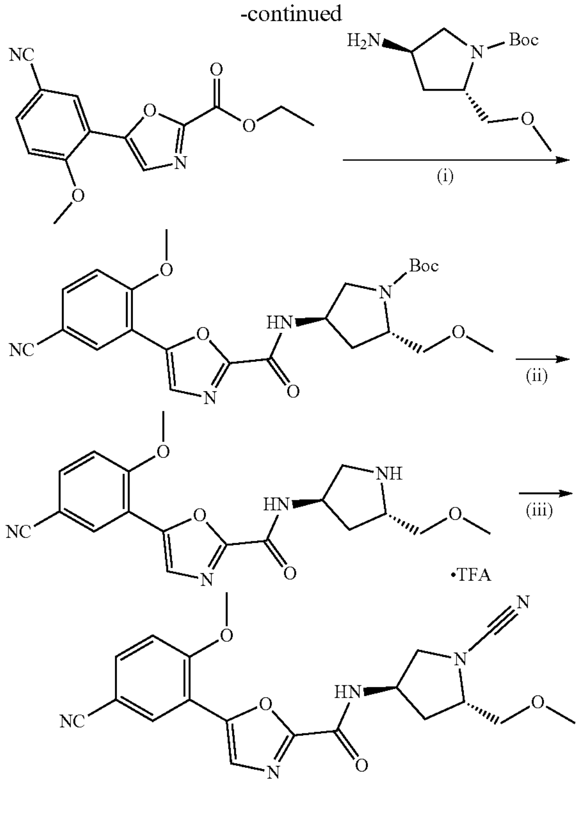

(i) TBD, THF, 0° C. to rt; (ii) TFA, DCM, 0° C. to rt; (iii) $K_2CO_3$, CNBr, THF, 0° C. to rt.

Step (i)

tert-Butyl (2S,4R)-4-(5-(5-cyano-2-methoxyphenyl) oxazole-2-carboxamido)-2-(methoxymethyl) pyrrolidine-1-carboxylate To a stirred solution of ethyl 5-(5-cyano-2-methoxyphenyl)oxazole-2-carboxylate (0.80 g, 2.94 mmol) and tert-butyl (2S,4R)-4-amino-2-(methoxymethyl)pyrrolidine-1-carboxylate (CAS 1207853-53-9, 0.67 g, 2.94 mmol) in THF (20 mL) was added TBD (0.61 g, 4.41 mmol) in portions at 0° C. The mixture was stirred at 0° C. for 6 h, then poured into water (50 mL) and extracted with EtOAc (2×70 mL). The combined organic phases were dried over anhydrous $Na_2SO_4$ and concentrated under reduced pressure. The residue was purified by flash column chromatography (silica gel, 50% EtOAc in n-hexanes) to yield tert-butyl (2S,4R)-4-(5-(5-cyano-2-methoxyphenyl)oxazole-2-carboxamido)-2-(methoxymethyl)pyrrolidine-1-carboxylate (0.25 g, 0.55 mmol, 18% yield).

LCMS: Method C1, 1.29 min; MS: ES+457.2.

Step (ii)

5-(5-Cyano-2-methoxyphenyl)-N-((3R,5S)-5-(methoxymethyl)pyrrolidin-3-yl)oxazole-2-carboxamide To a stirred solution of tert-butyl (2S,4R)-4-(5-(5-cyano-2-methoxyphenyl)oxazole-2-carboxamido)-2-(methoxymethyl)pyrrolidine-1-carboxylate (0.25 g, 0.55 mmol) in DCM (5 mL) was added TFA (2.5 mL, 10 vol) dropwise at 0° C. The mixture was allowed to warm to rt and stirred for 2 h, then concentrated under reduced pressure to yield 5-(5-cyano-2-methoxyphenyl)-N-((3R,5S)-5-(methoxymethyl)pyrrolidin-3-yl)oxazole-2-carboxamide TFA salt (0.32 g, quantitative yield).

LCMS: Method C1, 1.00 min; MS: ES+357.3.

Step (iii)

5-(5-Cyano-2-methoxyphenyl)-N-((3R,5S)-1-cyano-5-(methoxymethyl)pyrrolidin-3-yl)oxazole-2-carboxamide To a stirred solution of 5-(5-cyano-2-methoxyphenyl)-N-((3R,5S)-5-(methoxymethyl)pyrrolidin-3-yl)oxazole-2-carboxamide TFA salt (0.31 g, 0.66 mmol) in THF (15 mL) was added $K_2CO_3$ (0.27 g, 1.98 mmol) at rt and after stirring for 10 min, to the mixture at 0° C. was added cyanogen bromide (0.07 g, 0.66 mmol). The mixture was stirred at 0° C. for 0.5 h, then poured into water (50 mL) and extracted with EtOAc (2×50 mL). The combined organic phases were dried over $Na_2SO_4$ and concentrated under reduced pressure. The residue was purified by flash column chromatography (silica gel, 60% EtOAc in n-hexanes) to yield 5-(5-cyano-2-methoxyphenyl)-N-((3R,5S)-1-cyano-5-(methoxymethyl)pyrrolidin-3-yl)oxazole-2-carboxamide (0.11 g, 0.29 mmol, 52% yield over two steps).

LCMS: Method H, 2.66 min; MS: ES+382.2; $^1$H NMR (400 MHz, DMSO-$d_6$) δ ppm: 9.34 (d, J=6.8 Hz, 1H), 8.25 (s, 1H), 7.96 (d, J=8.0 Hz, 1H), 7.85 (s, 1H), 7.43 (d, J=8.8 Hz, 1H), 4.47-4.58 (m, 1H), 4.09 (s, 3H), 4.00-4.10 (m, 1H), 3.70-3.74 (m, 1H), 3.41-3.53 (m, 3H), 3.36 (s, 3H), 2.08-2.20 (m, 1H), 1.95-2.06 (m, 1H). Chiral SFC: Method Y7, 5.42 min.

Example 6

4-(5-Cyano-2-methoxyphenyl)-N-((3R,5S)-1-cyano-5-(methoxymethyl)pyrrolidin-3-yl)oxazole-2-carboxamide

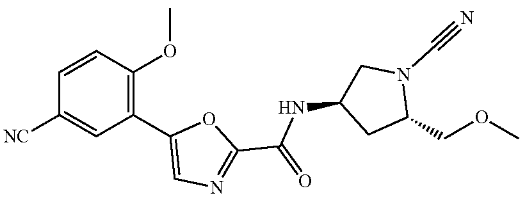

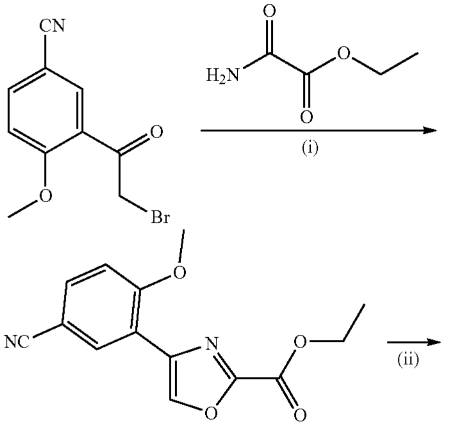

-continued

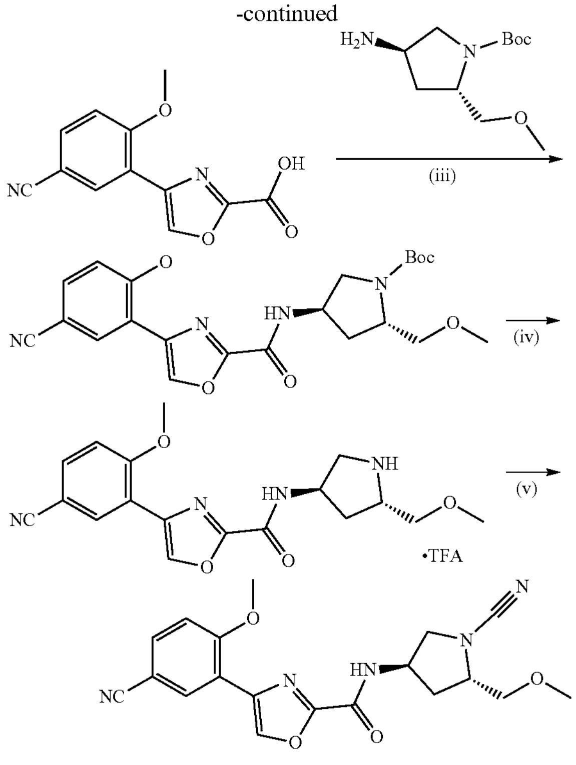

(i) AgOTf, EtOAc, 80° C.; (ii) LiOH·$H_2O$, $H_2O$, THF, 0° C. to rt; (iii) $POCl_3$, pyridine, 0° C. to rt; (iv) TFA, DCM, 0° C. to rt; (v) $K_2CO_3$, CNBr, THF, 0° C. to rt.

Step (i)

Ethyl 4-(5-cyano-2-methoxyphenyl)oxazole-2-carboxylate

To a stirred solution of ethyl 5-(5-cyano-2-methoxyphenyl)oxazole-2-carboxylate (3.5 g, 13.83 mmol) and ethyl oxamate (CAS 617-36-7, from Sigma-Aldrich, 4.86 g, 41.51 mmol) in EtOAc (35 mL) was added silver triflate (CAS 2923-28-6, from Combi-blocks, 10.66 g, 41.51 mmol) at rt. The mixture was heated at 80° C. for 24 h, then poured into water (120 mL), filtered through Celite Hyflow™ and the filtrate was extracted with EtOAc (3×70 mL). The combined organic phases were dried over anhydrous $Na_2SO_4$ and concentrated under reduced pressure. The residue was purified by flash column chromatography (silica gel, 16% EtOAc in n-hexanes) to yield ethyl 4-(5-cyano-2-methoxyphenyl) oxazole-2-carboxylate (0.53 g, 1.95 mmol, 14% yield).

LCMS: Method C, 1.65 min; MS: ES+273.1.

Step (ii)

4-(5-Cyano-2-methoxyphenyl)oxazole-2-carboxylic acid

To a stirred solution of ethyl 4-(5-cyano-2-methoxyphenyl)oxazole-2-carboxylate (0.50 g, 1.84 mmol) in THF: water (1:1, 10 mL) was added lithium hydroxide monohydrate (0.23 g, 5.51 mmol) in portions at 0° C. The mixture was stirred at 0° C. for 2 h, then poured into water (70 mL), acidified with 1N HCl and extracted with DCM (3×70 mL). The combined organic phases were dried over anhydrous $Na_2SO_4$ and concentrated under reduced pressure to yield 4-(5-cyano-2-methoxyphenyl)oxazole-2-carboxylic acid (0.15 g, 0.61 mmol, 33% yield). LCMS: Method C2, 0.81 min; MS: ES+245.1.

Step (iii)

tert-Butyl (2S,4R)-4-(4-(5-cyano-2-methoxyphenyl) oxazole-2-carboxamido)-2-(methoxymethyl)pyrrolidine-1-carboxylate To a stirred solution of 4-(5-cyano-2-methoxyphenyl) oxazole-2-carboxylic acid (0.16 g, 0.65 mmol) and tert-butyl (2S,4R)-4-amino-2-(methoxymethyl)pyrrolidine-1-carboxylate (CAS 1207853-53-9, 0.15 g, 0.65 mmol) in pyridine (3 mL) was added $POCl_3$ (0.3 g, 0.18 mL, 1.97 mmol) dropwise at 0° C. The mixture was stirred at 0° C. for 10 min, then poured into water (50 mL) and extracted with EtOAc (2×30 mL). The combined organic phases were dried over anhydrous $Na_2SO_4$ and concentrated under reduced pressure. The residue was purified by flash column chromatography (silica gel, 22% EtOAc in n-hexanes) to yield tert-butyl (2S,4R)-4-(4-(5-cyano-2-methoxyphenyl)oxazole-2-carboxamido)-2-(methoxymethyl)pyrrolidine-1-carboxylate (0.18 g, 0.39 mmol, 60% yield).

LCMS: Method C, 1.70 min; MS: ES− 455.1.

Step (iv)

4-(5-Cyano-2-methoxyphenyl)-N-((3R,5S)-5-(methoxymethyl)pyrrolidin-3-yl)oxazole-2-carboxamide To a stirred solution of tert-butyl (2S,4R)-4-(4-(5-cyano-2-methoxyphenyl)oxazole-2-carboxamido)-2-(methoxymethyl)pyrrolidine-1-carboxylate (0.17 g, 0.37 mmol) in DCM (5 mL) was added TFA (0.85 mL, 5 vol) dropwise at 0° C. The mixture was allowed to warm to rt and stirred for 1 h, then concentrated under reduced pressure to yield 4-(5-cyano-2-methoxyphenyl)-N-((3R,5S)-5-(methoxymethyl) pyrrolidin-3-yl)oxazole-2-carboxamide TFA salt (0.25 g, quantitative yield).

LCMS: Method C, 1.32 min; MS: ES+357.1.

Step (v)

4-(5-Cyano-2-methoxyphenyl)-N-((3R,5S)-1-cyano-5-(methoxymethyl)pyrrolidin-3-yl)oxazole-2-carboxamide To a stirred solution of 4-(5-cyano-2-methoxyphenyl)-N-((3R,5S)-5-(methoxymethyl)pyrrolidin-3-yl) oxazole-2-carboxamide TFA salt (0.24 g, 0.51 mmol) in THF (5 mL) was added $K_2CO_3$ (0.21 g, 1.53 mmol) at rt and stirred for 10 min. Cyanogen bromide (0.04 g, 0.41 mmol) was added at 0° C. The mixture was stirred at rt for 1 h, then poured into water (50 mL) and extracted with EtOAc (3×50 mL). The combined organic phases were dried over $Na_2SO_4$ and concentrated under reduced pressure. The residue was purified by flash column chromatography (silica gel, 71% EtOAc in n-hexanes) to yield 4-(5-cyano-2-methoxyphenyl)-N-((3R,5S)-1-cyano-5-(methoxymethyl)pyrrolidin-3-yl)oxazole-2-carbox amide (0.05 g, 0.14 mmol, 36% yield over two steps).

LCMS: Method H, 2.80 min; MS: ES− 380.1; $^1H$ NMR (400 MHz, DMSO-$d_6$) δ ppm: 9.25 (d, J=6.8 Hz, 1H), 8.72 (s, 1H), 8.44 (d, J=1.6 Hz, 1H), 7.89 (dd, J=8.8, 2.0 Hz, 1H), 7.37 (d, J=8.8 Hz, 1H), 4.47-4.58 (m, 1H), 4.07 (s, 3H), 4.00-4.18 (m, 1H), 3.69-3.73 (m, 1H), 3.43-3.50 (m, 3H), 3.34 (s, 3H), 2.09-2.19 (m, 1H), 1.96-2.02 (m, 1H). Chiral SFC: Method Y3, 3.49 min.

Example 7

5-(5-Cyano-2-(trifluoromethoxy)phenyl)-N-((3R,5S)-1-cyano-5-(methoxymethyl)pyrrolidin-3-yl)oxazole-2-carboxamide

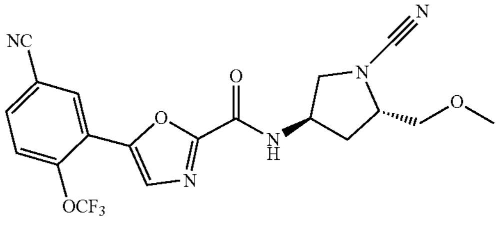

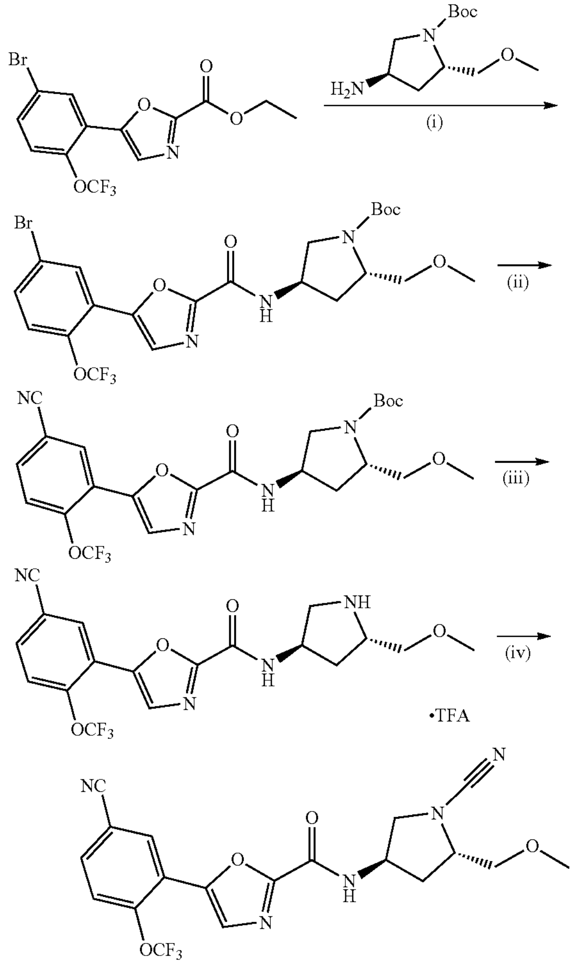

(i) TBD, THF, 0° C. to rt; (ii) $Zn(CN)_2$, Zn, $Pd_2(dba)_3$, phosphine ligand, DMA, 140° C.; (iii) TFA, DCM, 0° C. to rt; (iv) $K_2CO_3$, CNBr, THF, 0° C. to rt.

Step (i)

tert-Butyl (2S,4R)-4-(5-(5-bromo-2-(trifluoromethoxy)phenyl)oxazole-2-carboxamido)-2-(methoxymethyl)pyrrolidine-1-carboxylate To a stirred solution of ethyl 5-(5-bromo-2-(trifluoromethoxy)phenyl)oxazole-2-carboxylate (0.70 g, 1.84 mmol) and tert-butyl (2S,4R)-4-amino-2-(methoxymethyl) pyrrolidine-1-carboxylate (CAS 1207853-53-9, 0.42 g, 1.84 mmol) in THF (8 mL) was added TBD (0.38 g, 2.77 mmol) in portions at 0° C. The mixture was stirred at 0° C. for 2 h, then poured into water (100 mL) and extracted with EtOAc (3×70 mL). The combined organic phases were dried over anhydrous $Na_2SO_4$ and concentrated under reduced pressure. The residue was purified by flash column chromatography (silica gel, 25% EtOAc in n-hexanes) to yield tert-butyl (2S,4R)-4-(5-(5-bromo-2-(trifluoromethoxy)phenyl) oxazole-2-carboxamido)-2-(methoxymethyl)pyrrolidine-1-carboxylate (0.37 g, 0.66 mmol, 35% yield).

LCMS: Method C, 2.00 min; MS: ES+564.4, 566.4.

Step (ii)

tert-Butyl (2S,4R)-4-(5-(5-cyano-2-(trifluoromethoxy)phenyl)oxazole-2-carboxamido)-2-(methoxymethyl)pyrrolidine-1-carboxylate To a stirred solution of tert-butyl (2S,4R)-4-(5-(5-bromo-2-(trifluoromethoxy)phenyl)oxazole-2-carboxamido)-2-(methoxymethyl)pyrrolidine-1-carboxylate (0.35 g, 0.62 mmol) in DMA (3 mL) was added zinc cyanide (0.18 g, 1.55 mmol), zinc dust (0.02 g, 0.31 mmol) and 1,1'-ferrocenediyl-bis(diphenylphosphine) (0.07 g, 0.12 mmol) at rt. The mixture was degassed with $N_2$ for 15 min, followed by addition of tris(dibenzylidene acetone)dipalladium(0) (0.11 g, 0.12 mmol). The mixture was heated under microwave at 140° C. for 1 h, then allowed to cool to rt, poured into ice-cold water (70 mL) and extracted with EtOAc (3×70 mL). The combined organic phases were dried over $Na_2SO_4$ and concentrated under reduced pressure. The residue was purified by flash column chromatography (silica gel, 22% EtOAc in n-hexanes) to yield tert-butyl (2S,4R)-4-(5-(5-cyano-2-(trifluoromethoxy)-phenyl)oxazole-2-carboxamido)-2-(methoxymethyl)pyrrolidine-1-carboxylate (0.25 g, 0.5 mmol, 80% yield).

LCMS: Method C, 1.83 min; MS: ES+: 511.4.

Step (iii)

5-(5-Cyano-2-(trifluoromethoxy)phenyl)-N-((3R,5S)-5-(methoxymethyl)pyrrolidin-3-yl)oxazole-2-carboxamide To a stirred solution of tert-butyl (2S,4R)-4-(5-(5-cyano-2-(trifluoromethoxy)phenyl)oxazole-2-carboxamido)-2-(methoxymethyl)pyrrolidine-1-carboxylate (0.25 g, 0.49 mmol) in DCM (3 mL) was added TFA (1.25 mL, 5 vol) dropwise at 0° C. The mixture was allowed to warm to rt and stirred for 2 h, then concentrated under reduced pressure to yield 5-(5-cyano-2-(trifluoromethoxy)phenyl)-N-((3R,5S)-5-(methoxymethyl)pyrrolidin-3-yl)oxazole-2-carboxamide TFA salt (0.39 g, quantitative yield).

LCMS: Method C, 1.38 min; MS: ES+411.1.

Step (iv)

5-(5-Cyano-2-(trifluoromethoxy)phenyl)-N-((3R,5S)-1-cyano-5-(methoxymethyl)pyrrolidin-3-yl)oxazole-2-carboxamide To a stirred solution of 5-(5-cyano-2-(trifluoromethoxy) phenyl)-N-((3R,5S)-5-(methoxymethyl) pyrrolidin-3-yl) oxazole-2-carboxamide TFA salt (0.39 g, 0.74 mmol) in THF (5 mL) was added $K_2CO_3$ (0.31 g, 2.23 mmol) at rt and stirred for 10 min. Cyanogen bromide (0.06 g, 0.59 mmol) was added at 0° C. The mixture was stirred at rt for 1 h, then poured into water (70 mL) and extracted with EtOAc (3×70 mL). The combined organic phases were dried over $Na_2SO_4$ and concentrated under reduced pressure. The residue was purified by flash column chromatography (silica gel, 40% EtOAc in n-hexanes) to yield 5-(5-cyano-2-(trifluoromethoxy)phenyl)-N-((3R,5S)-1-cyano-5-(methoxymethyl) pyrrolidin-3-yl)oxazole-2-carboxamide (0.14 g, 0.33 mmol, 66% yield over two steps).

LCMS: Method H, 3.03 min; MS: ES− 434.1; $^1H$ NMR (400 MHz, DMSO-$d_6$) δ ppm: 9.40 (d, J=6.8 Hz, 1H), 8.51 (d, J=1.6 Hz, 1H), 8.12 (dd, J=8.8, 2.0 Hz, 1H), 7.86 (s, 1H), 7.82 (d, J=8.4 Hz, 1H), 4.51-4.55 (m, 1H), 3.99-4.08 (m, 1H), 3.69-3.74 (m, 1H), 3.42-3.51 (m, 3H), 3.34 (s, 3H), 2.11-2.17 (m, 1H), 1.97-2.03 (m, 1H). Chiral SFC: Method Y4, 3.57 min.

Example 8

5-(5-Cyano-2-(trifluoromethoxy)phenyl)-N-((3R,5R)-1-cyano-5-methylpyrrolidin-3-yl)oxazole-2-carboxamide

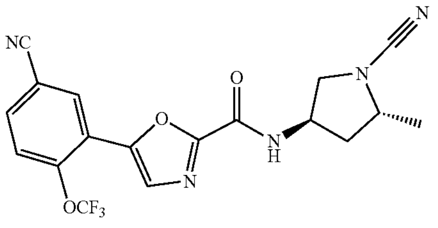

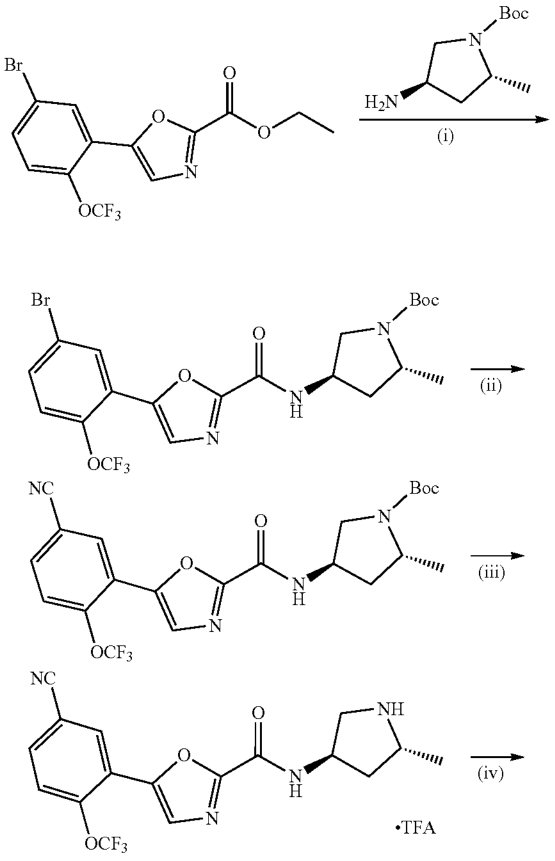

-continued

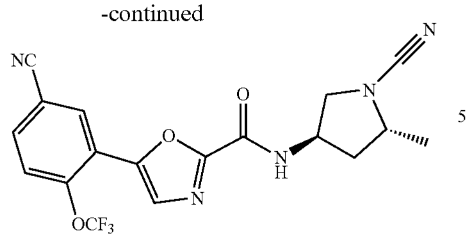

(i) TBD, THF, 0° C. to rt; (ii) $Zn(CN)_2$, Zn, $Pd_2(dba)_3$, phosphine ligand, DMA, 140° C.; (iii) TFA, DCM, 0° C. to rt; (iv) $K_2CO_3$, CNBr, THF, 0° C. to rt.

Step (i)

tert-Butyl (2R,4R)-4-(5-(5-bromo-2-(trifluoromethoxy)phenyl)oxazole-2-carboxamido)-2-methylpyrrolidine-1-carboxylate To a stirred solution of ethyl 5-(5-bromo-2-(trifluoromethoxy)phenyl)oxazole-2-carboxylate (0.40 g, 1.05 mmol) and tert-butyl (2R,4R)-4-amino-2-methylpyrrolidine-1-carboxylate (CAS 348165-63-9, 0.23 g, 1.16 mmol) in THF (8 mL) was added TBD (0.22 g, 1.57 mmol) in portions at 0° C. The mixture was allowed to warm to rt and stirred for 3 h, then poured into water (50 mL) and extracted with EtOAc (3×60 mL). The combined organic phases were dried over anhydrous $Na_2SO_4$ and concentrated under reduced pressure. The residue was purified by flash column chromatography (silica gel, 32% EtOAc in n-hexanes) to yield tert-butyl (2R,4R)-4-(5-(5-bromo-2-(trifluoromethoxy)phenyl)oxazole-2-carboxamido)-2-methylpyrrolidine-1-carboxylate (0.14 g, 0.26 mmol, 24% yield).

LCMS: Method C, 2.01 min; MS: ES+534.2, 536.2.

Step (ii)

tert-Butyl (2R,4R)-4-(5-(5-cyano-2-(trifluoromethoxy)phenyl)oxazole-2-carboxamido)-2-methylpyrrolidine-1-carboxylate To a stirred solution of tert-butyl (2R,4R)-4-(5-(5-bromo-2-(trifluoromethoxy)phenyl)oxazole-2-carboxamido)-2-methylpyrrolidine-1-carboxylate (0.13 g, 0.24 mmol) in DMA (1.3 mL) was added zinc cyanide (0.07 g, 0.61 mmol), zinc dust (0.01 g, 0.12 mmol) and 1,1'-ferrocenediyl-bis(diphenylphosphine) (0.03 g, 0.05 mmol) at rt. The mixture was degassed with $N_2$ for 10 min, followed by addition of tris(dibenzylidene acetone)dipalladium(0) (0.04 g, 0.05 mmol). The mixture was heated under microwave at 140° C. for 1 h, then allowed to cool to rt, poured into water (20 mL) and extracted with EtOAc (3×30 mL). The combined organic phases were dried over $Na_2SO_4$ and concentrated under reduced pressure. The residue was purified by flash column chromatography (silica gel, 38% EtOAc in n-hexanes) to yield tert-butyl (2R,4R)-4-(5-(5-cyano-2-(trifluoromethoxy)phenyl)-oxazole-2-carboxamido)-2-methylpyrrolidine-1-carboxylate (0.05 g, 0.10 mmol, 42% yield).

LCMS: Method C, 1.88 min; MS: ES+: 425.6 (M-56).

Step (iii)

5-(5-Cyano-2-(trifluoromethoxy)phenyl)-N-((3R,5R)-5-methylpyrrolidin-3-yl)oxazole-2-carboxamide To a stirred solution of tert-butyl (2R,4R)-4-(5-(5-cyano-2-(trifluoromethoxy)phenyl)oxazole-2-carboxamido)-2-methylpyrrolidine-1-carboxylate (0.05 g, 0.1 mmol) in DCM (2 mL) was added TFA (0.15 mL, 3 vol) dropwise at 0° C. The mixture was allowed to warm to rt and stirred for 1 h, then concentrated under reduced pressure to yield 5-(5-cyano-2-(trifluoromethoxy)phenyl)-N-((3R,5R)-5-methylpyrrolidin-3-yl)oxazole-2-carboxamide TFA salt (0.08 g, quantitative yield).

LCMS: Method C, 1.38 min; MS: ES+381.2.

Step (iv)

5-(5-Cyano-2-(trifluoromethoxy)phenyl)-N-((3R,5R)-1-cyano-5-methylpyrrolidin-3-yl)oxazole-2-carboxamide To a stirred solution of 5-(5-cyano-2-(trifluoromethoxy)phenyl)-N-((3R,5R)-5-methylpyrrolidin-3-yl)oxazole-2-carboxamide TFA salt (0.08 g, 0.16 mmol) in THF (4 mL) was added $K_2CO_3$ (0.07 g, 0.48 mmol) at rt and stirred for 10 min. Cyanogen bromide (0.02 g, 0.16 mmol) was added at 0° C. The mixture was stirred at rt for 1 h, then poured into water (20 mL) and extracted with EtOAc (3×25 mL). The combined organic phases were dried over $Na_2SO_4$ and concentrated under reduced pressure. The residue was purified by flash column chromatography (silica gel, 47% EtOAc in n-hexanes) to yield 5-(5-cyano-2-(trifluoromethoxy)phenyl)-N-((3R,5R)-1-cyano-5-methylpyrrolidin-3-yl)oxazole-2-carboxamide (0.02 g, 0.05 mmol, 47% yield over two steps).

LCMS: Method H, 3.02 min; MS: ES− 404.0; $^1$H NMR (400 MHz, DMSO-$d_6$) δ ppm: 9.43 (d, J=6.8 Hz, 1H), 8.51 (s, 1H), 8.11 (d, J=8.4 Hz, 1H), 7.84 (s, 1H), 7.82 (d, J=8.4 Hz, 1H), 4.48-4.57 (m, 1H), 3.89-3.94 (m, 1H), 3.76-3.80 (m, 1H), 3.42-3.46 (m, 1H), 2.15-2.18 (m, 1H), 1.76-1.83 (m, 1H), 1.25 (d, J=6.4 Hz, 3H). Chiral SFC: Method Y8, 5.02 min.

Example 9

5-(5-Cyano-4-fluoro-2-methoxyphenyl)-N-((3R,5R)-1-cyano-5-methylpyrrolidin-3-yl)oxazole-2-carboxamide

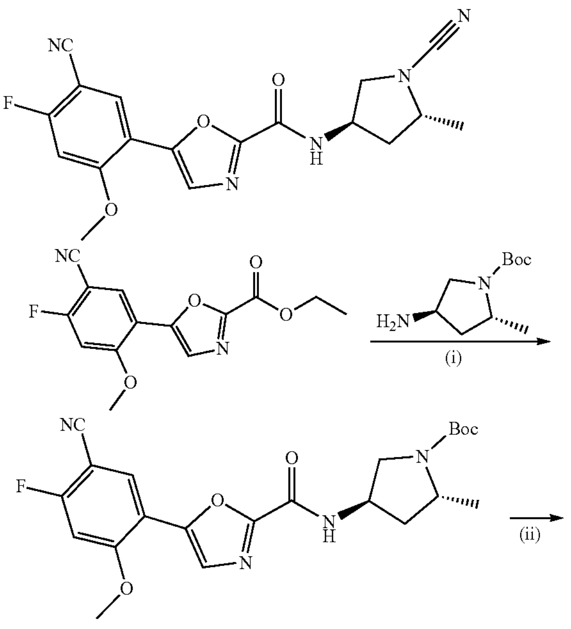

-continued

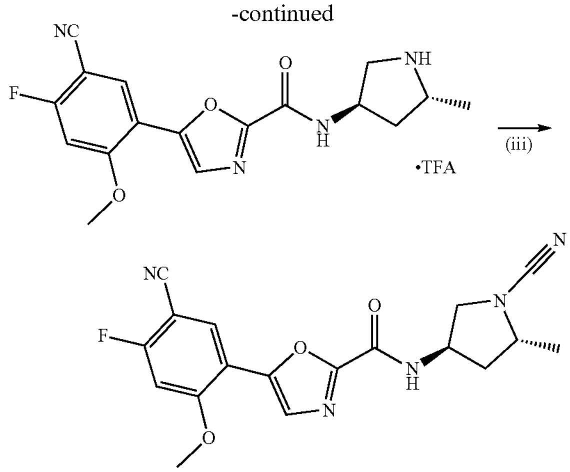

(i) TBD, THF, 0° C. to rt; (ii) TFA, DCM, 0° C. to rt; (iii) $K_2CO_3$, CNBr, THF, 0° C. to rt.

Step (i)

tert-Butyl (2R, 4R)-4-(5-(5-cyano-2-cyclopropoxy-phenyl)oxazole-2-carboxamido)-2-methylpyrrolidine-1-carboxylate To a stirred solution of ethyl 5-(5-cyano-2-cyclopropoxy-phenyl)oxazole-2-carboxylate (0.50 g, 1.72 mmol) and tert-butyl (2R,4R)-4-amino-2-methylpyrrolidine-1-carboxylate (CAS 348165-63-9, 0.27 g, 1.38 mmol) in THF (10 mL) was added TBD (0.29 g, 2.07 mmol) in portions at 0° C. The mixture was warmed to rt and stirred for 2 h, then poured into water (50 mL) and extracted with EtOAc (2×50 mL). The combined organic phases were dried over anhydrous $Na_2SO_4$ and concentrated under reduced pressure. The residue was purified by flash column chromatography (silica gel, 40% EtOAc in n-hexanes) to yield tert-butyl (2R,4R)-4-(5-(5-cyano-2-cyclopropoxyphenyl)oxazole-2-carboxamido)-2-methylpyrrolidine-1-carboxylate (0.3 g, 0.67 mmol, 38% yield).

LCMS: Method C, 1.78 min; MS: ES+389.3 (M-56).

Step (ii)

5-(5-Cyano-2-cyclopropoxyphenyl)-N-((3R,5R)-5-methylpyrrolidin-3-yl)oxazole-2-carboxamide To a stirred solution of tert-butyl (2R,4R)-4-(5-(5-cyano-2-cyclopropoxyphenyl)oxazole-2-carboxamido)-2-methylpyrrolidine-1-carboxylate (0.3 g, 0.67 mmol) in DCM (7 mL) was added TFA (0.9 mL, 3 vol) dropwise at 0° C. The mixture was allowed to warm to rt and stirred for 1 h, then concentrated under reduced pressure to yield 5-(5-cyano-2-cyclopropoxyphenyl)-N-((3R,5R)-5-methylpyrrolidin-3-yl) oxazole-2-carboxamide TFA salt (0.29 g, quantitative yield).

LCMS: Method C, 1.39 min; MS: ES+345.3.

Step (iii)

5-(5-Cyano-4-fluoro-2-methoxyphenyl)-N-((3R,5R)-1-cyano-5-methylpyrrolidin-3-yl)oxazole-2-carboxamide To a stirred solution of 5-(5-cyano-2-cyclopropoxyphenyl)-N-((3R,5R)-5-methylpyrrolidin-3-yl)oxazole-2-carboxamide TFA salt (0.29 g, 0.63 mmol) in THF (7 mL) was added $K_2CO_3$ (0.26 g, 1.89 mmol) at rt and stirred for 10 min. Cyanogen bromide (0.07 g, 0.63 mmol) was added at 0° C. The mixture was stirred at rt for 1 h, then poured into water (70 mL) to form a precipitate, and the solid was collected by filtration under reduced pressure to yield 5-(5-cyano-4-fluoro-2-methoxyphenyl)-N-((3R,5R)-1-cyano-5-methylpyrrolidin-3-yl)oxazole-2-carboxamide (0.13 g, 0.35 mmol, 52% yield over two steps).

LCMS: Method H, 2.75 min; MS: ES+370.1; $^1H$ NMR (400 MHz, DMSO-$d_6$) δ ppm: 9.31 (d, J=6.4 Hz, 1H), 8.28-8.31 (m, 1H), 7.79-7.82 (m, 1H), 7.49-7.52 (m, 1H), 4.47-4.59 (m, 1H), 4.08 (s, 3H), 3.85-3.99 (m, 1H), 3.76-3.80 (m, 1H), 3.42-3.45 (m, 1H), 2.12-2.23 (m, 1H), 1.73-1.87 (m, 1H), 1.24-1.29 (m, 3H). Chiral SFC: Method Y5, 4.98 min.

Example 10

4-(5-Cyano-2-cyclopropoxyphenyl)-N-((3R,5S)-1-cyano-5-(methoxymethyl)pyrrolidin-3-yl)oxazole-2-carboxamide

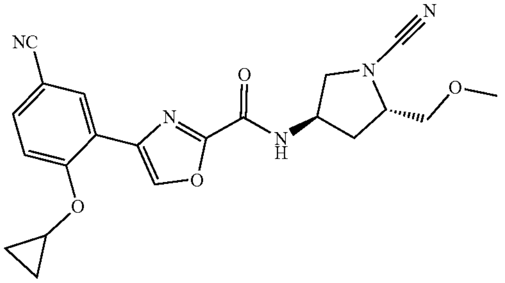

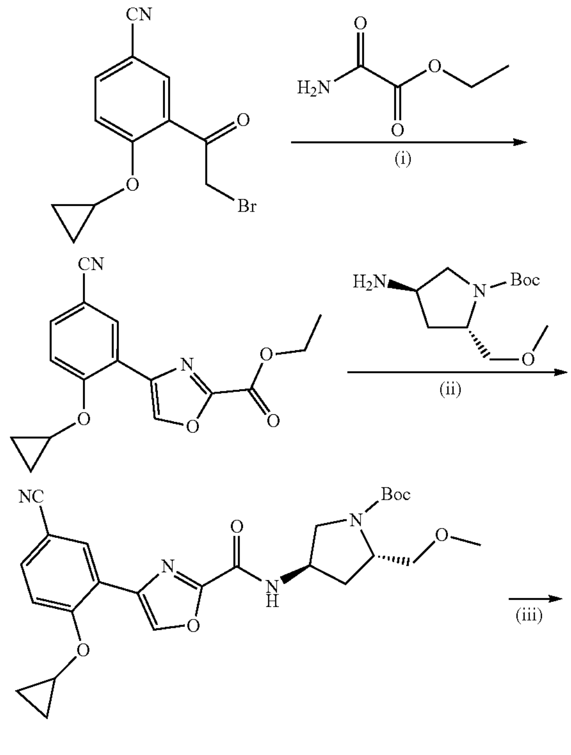

-continued

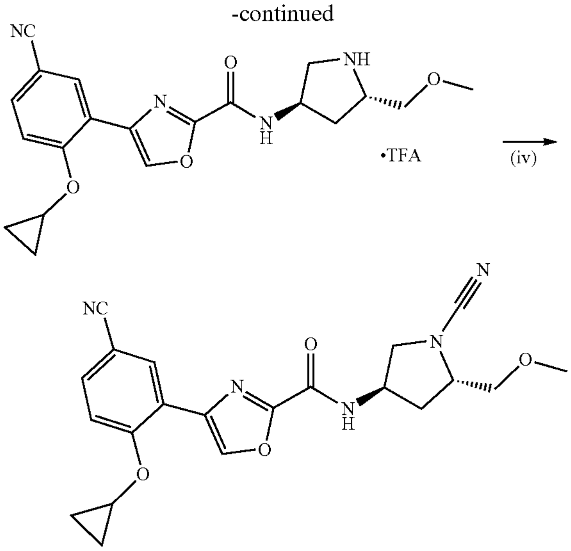

Step (i)

Ethyl 4-(5-cyano-2-cyclopropoxyphenyl)oxazole-2-carboxylate

To a stirred solution of 3-(2-bromoacetyl)-4-cyclopropoxybenzonitrile (0.70 g, 2.50 mmol) and ethyl oxamate (CAS 617-36-7, from Sigma-Aldrich, 0.66 g, 3.75 mmol) in EtOAc (10 mL) was added silver triflate (CAS 2923-28-6, from Combi-blocks, 0.96 g, 3.75 mmol) at rt. The mixture was heated at 80° C. for 16 h. One more identical batch was combined and then poured into water (100 mL), filtered through Celite Hyflow™ and the filtrate was extracted with EtOAc (2×100 mL). The combined organic phases were dried over anhydrous $Na_2SO_4$ and concentrated under reduced pressure. The residue was purified by flash column chromatography (silica gel, 10% EtOAc in n-hexanes) to yield ethyl 4-(5-cyano-2-cyclopropoxyphenyl)oxazole-2-carboxylate (0.35 g, 1.17 mmol, 23% yield).

LCMS: Method H1, 3.40 min; MS: ES+299.0.

Step (ii)

tert-Butyl (2S,4R)-4-(4-(5-cyano-2-cyclopropoxyphenyl)oxazole-2-carboxamido)-2-(methoxymethyl)pyrrolidine-1-carboxylate To a stirred solution of ethyl 4-(5-cyano-2-cyclopropoxyphenyl)oxazole-2-carboxylate (0.32 g, 1.07 mmol) and tert-butyl (2S,4R)-4-amino-2-(methoxymethyl)pyrrolidine-1-carboxylate (CAS 1207853-53-9, 0.25 g, 1.07 mmol) in DMF (7 mL) was added TBD (0.18 g, 1.28 mmol) in portions at 0° C. The mixture was allowed to warm to rt and stirred for 2 h, then poured into water (50 mL) and extracted with EtOAc (2×50 mL). The combined organic phases were dried over anhydrous $Na_2SO_4$, filtered and concentrated under reduced pressure. The residue was purified by flash column chromatography (silica gel, 30% EtOAc in n-hexanes) to yield tert-butyl (2S,4R)-4-(4-(5-cyano-2-cyclopropoxyphenyl)oxazole-2-carboxamido)-2-(methoxymethyl)pyrrolidine-1-carboxylate (0.10 g, 0.22 mmol, 20% yield).

LCMS: Method H1, 3.51 min; MS: ES− 481.3.

Step (iii)

4-(5-Cyano-2-cyclopropoxyphenyl)-N-((3R,5S)-5-(methoxymethyl)pyrrolidin-3-yl)oxazole-2-carboxamide TFA salt To a stirred solution of tert-butyl (2S,4R)-4-(4-(5-cyano-2-cyclopropoxyphenyl)oxazole-2-carboxamido)-2-(methoxymethyl)pyrrolidine-1-carboxylate (0.1 g, 0.22 mmol) in DCM (5 mL) was added TFA (1 mL, 10 vol) dropwise at 0° C. The mixture was allowed to warm to rt and stirred for 1 h, then concentrated under reduced pressure to yield 4-(5-cyano-2-cyclopropoxyphenyl)-N-((3R,5S)-5-(methoxymethyl)pyrrolidin-3-yl)oxazole-2-carboxamide TFA salt (0.14 g, quantitative yield).

LCMS: Method J, 3.61 min; MS: ES+383.0.

Step (iv)

4-(5-Cyano-2-cyclopropoxyphenyl)-N-((3R,5S)-1-cyano-5-(methoxymethyl)pyrrolidin-3-yl)oxazole-2-carboxamide To a stirred solution of 4-(5-cyano-2-cyclopropoxyphenyl)-N-((3R,5S)-5-(methoxymethyl)pyrrolidin-3-yl)oxazole-2-carboxamide TFA salt (0.14 g, 0.28 mmol) in THF (5 mL) was added $K_2CO_3$ (0.12 g, 0.84 mmol) at rt and stirred for 5 min. Cyanogen bromide (0.03 g, 0.28 mmol) was added at 0° C. The mixture was stirred at rt for 1 h, then poured into water (30 mL) and extracted with EtOAc (2×30 mL). The combined organic phases were dried over $Na_2SO_4$ and concentrated under reduced pressure. The residue was purified by flash column chromatography (silica gel, 45% EtOAc in n-hexanes) to yield 4-(5-cyano-2-cyclopropoxyphenyl)-N-((3R,5S)-1-cyano-5-(methoxymethyl)pyrrolidin-3-yl)oxazole-2-carboxamide (0.04 g, 0.09 mmol, 47% yield, over two steps).

LCMS: Method H1, 2.97 min; MS: ES− 406.2; $^1H$ NMR (400 MHz, DMSO-$d_6$) δ ppm: 9.24 (d, J=6.8 Hz, 1H), 8.52 (s, 1H), 8.43 (d, J=2.0 Hz, 1H), 7.92 (dd, J=8.8, 2.0 Hz, 1H), 7.64 (d, J=8.4 Hz, 1H), 4.48-4.56 (m, 1H), 4.15-4.23 (m, 1H), 4.0-4.08 (m, 1H), 3.68-3.72 (m, 1H), 3.42-3.50 (m, 3H), 3.32 (s, 3H), 2.10-2.15 (m, 1H), 1.96-2.01 (m, 1H), 0.86-0.97 (m, 4H).

Chiral HPLC: Method Y15, 10.0 min.

Example 11

5-(5-Cyano-2-cyclopropoxyphenyl)-N-((3R,5R)-1-cyano-5-(methoxymethyl)pyrrolidin-3-yl)oxazole-2-carboxamide

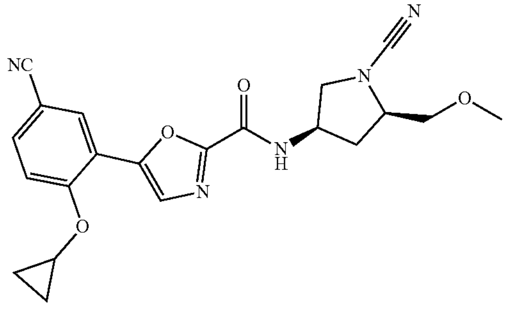

-continued

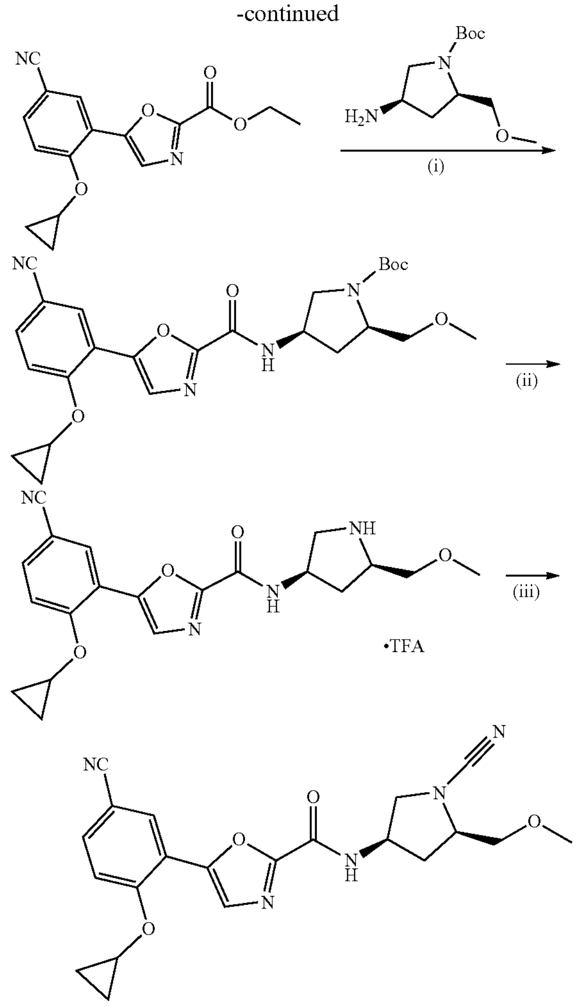

Step (i)

tert-Butyl (2R,4R)-4-(5-(5-cyano-2-cyclopropoxy-phenyl)oxazole-2-carboxamido)-2-(methoxymethyl) pyrrolidine-1-carboxylate To a stirred solution of ethyl 5-(5-cyano-2-cyclopropoxy-phenyl)oxazole-2-carboxylate (0.25 g, 0.83 mmol) and tert-butyl (2R,4R)-4-amino-2-(methoxymethyl)pyrrolidine-1-carboxylate (CAS 1123305-98-5, 0.19 g, 0.83 mmol) in toluene (5 mL) was added TBD (0.12 g, 0.83 mmol) in portions at 0° C. The mixture was allowed to warm to rt and stirred for 1 h, then poured into water (50 mL) and extracted with EtOAc (2×50 mL). The combined organic phases were dried over anhydrous $Na_2SO_4$, filtered and concentrated under reduced pressure. The residue was purified by flash column chromatography (silica gel, 35% EtOAc in n-hexanes) to yield tert-butyl (2R,4R)-4-(5-(5-cyano-2-cyclopropoxyphenyl) oxazole-2-carboxamido)-2-(methoxymethyl)pyrrolidine-1-carboxylate (0.08 g, 0.16 mmol, 19% yield).

LCMS: Method C1, 1.41 min; MS: ES+483.4.

Step (ii)

5-(5-Cyano-2-cyclopropoxyphenyl)-N-((3R,5R)-5-(methoxymethyl)pyrrolidin-3-yl)oxazole-2-carboxamide TFA salt To a stirred solution of tert-butyl (2R,4R)-4-(5-(5-cyano-2-cyclopropoxyphenyl)oxazole-2-carboxamido)-2-(methoxymethyl)pyrrolidine-1-carboxylate (0.07 g, 0.15 mmol) in DCM (1 mL) was added TFA (0.22 mL, 3 vol) dropwise at 0° C. The mixture was allowed to warm to rt and stirred for 1 h, then concentrated under reduced pressure to yield 5-(5-cyano-2-cyclopropoxyphenyl)-N-((3R,5R)-5-(methoxymethyl)pyrrolidin-3-yl)oxazole-2-carboxamide TFA salt (0.10 g, quantitative yield).

LCMS: Method C1, 1.06 min; MS: ES+383.2.

Step (iii)

5-(5-Cyano-2-cyclopropoxyphenyl)-N-((3R,5R)-1-cyano-5-(methoxymethyl)pyrrolidin-3-yl)oxazole-2-carboxamide To a stirred solution of 5-(5-cyano-2-cyclopropoxyphenyl)-N-((3R,5R)-5-(methoxymethyl)pyrrolidin-3-yl)oxazole-2-carboxamide TFA salt (0.10 g, 0.20 mmol) in THF (5 mL) was added $K_2CO_3$ (0.08 g, 0.60 mmol) at rt and stirred for 5 min. Cyanogen bromide (0.02 g, 0.20 mmol) was added at 0° C. The mixture was stirred at rt for 1 h, then poured into water (50 mL) and extracted with EtOAc (2×50 mL). The combined organic phases were dried over $Na_2SO_4$ and concentrated under reduced pressure. The residue was purified by flash column chromatography (silica gel, 45% EtOAc in n-hexanes) to yield 5-(5-cyano-2-cyclopropoxyphenyl)-N-((3R,5R)-1-cyano-5-(methoxymethyl)pyrrolidin-3-yl)oxazole-2-carboxamide (0.02 g, 0.04 mmol, 29% yield, over two steps).

LCMS: Method H1, 2.94 min; MS: ES+408.2; $^1H$ NMR (400 MHz, DMSO-$d_6$) δ ppm: 9.18 (d, J=6.8 Hz, 1H), 8.24 (s, 1H), 7.96 (d, J=8.4 Hz, 1H), 7.67-7.69 (m, 2H), 4.50-4.61 (m, 1H), 4.15-4.25 (m, 1H), 3.88-3.97 (m, 1H), 3.63-3.72 (m, 1H), 3.46-3.60 (m, 2H), 3.37-3.41 (m, 4H), 2.27-2.38 (m, 1H), 1.80-1.90 (m, 1H), 0.83-0.98 (m, 4H). Chiral SFC: Method Y12, 3.53 min.

Example 12

4-(5-Cyano-2-cyclopropoxyphenyl)-N-((3R,5R)-1-cyano-5-(methoxymethyl)pyrrolidin-3-yl)oxazole-2-carboxamide

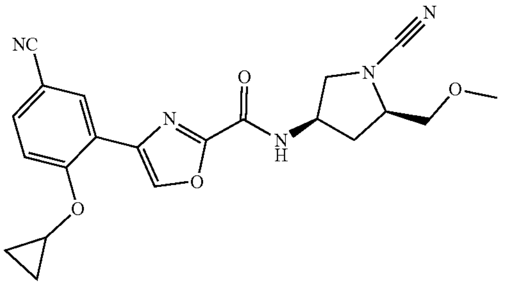

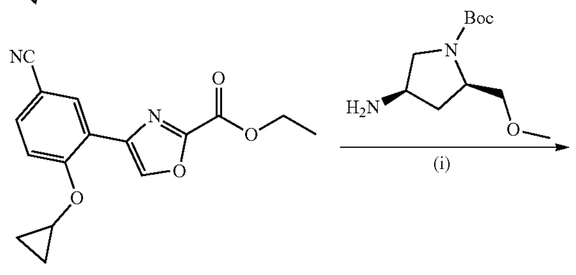

-continued

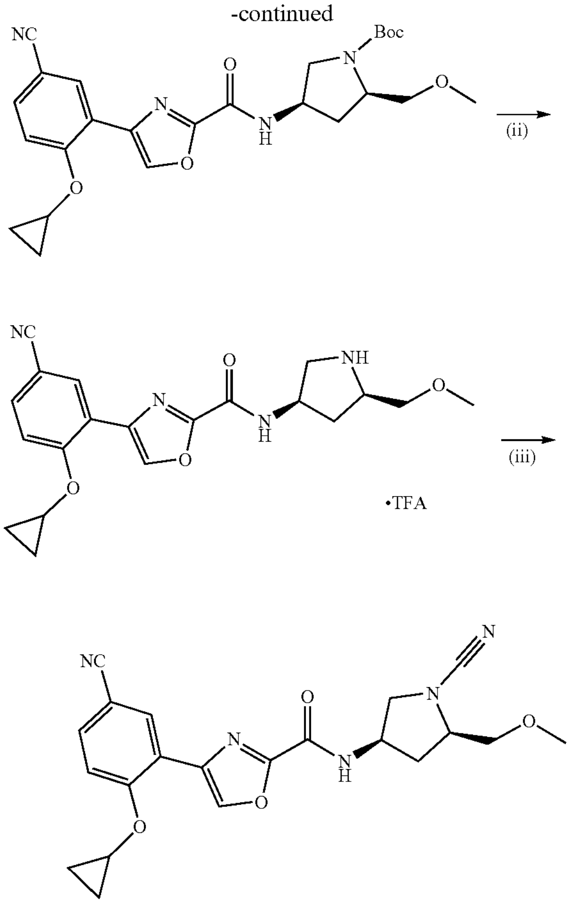

Step (i)

tert-Butyl (2R,4R)-4-(4-(5-cyano-2-cyclopropoxyphenyl)oxazole-2-carboxamido)-2-(methoxymethyl)pyrrolidine-1-carboxylate To a stirred solution of ethyl 4-(5-cyano-2-cyclopropoxyphenyl)oxazole-2-carboxylate (0.40 g, 1.34 mmol) [Example 10; Step (i)] and tert-butyl (2R,4R)-4-amino-2-(methoxymethyl)pyrrolidine-1-carboxylate (CAS 1123305-98-5, 0.31 g, 1.34 mmol) in toluene (5 mL) was added TBD (0.19 g, 1.34 mmol) in portions at 0° C. The mixture was allowed to warm to rt and stirred for 4 h, then poured into water (50 mL) and extracted with EtOAc (2×50 mL). The combined organic phases were dried over anhydrous $Na_2SO_4$, filtered and concentrated under reduced pressure. The residue was purified by flash column chromatography (silica gel, 40% EtOAc in n-hexanes) to yield tert-butyl (2R,4R)-4-(4-(5-cyano-2-cyclopropoxy phenyl)oxazole-2-carboxamido)-2-(methoxymethyl)pyrrolidine-1-carboxylate (0.22 g, 0.46 mmol, 34% yield). LCMS: Method C1, 1.42 min, MS: ES+483.3.

Step (ii)

4-(5-Cyano-2-cyclopropoxyphenyl)-N-((3R,5R)-5-(methoxymethyl)pyrrolidin-3-yl)oxazole-2-carboxamide TFA salt To a stirred solution of tert-butyl (2R,4R)-4-(4-(5-cyano-2-cyclopropoxyphenyl)oxazole-2-carboxamido)-2-(methoxymethyl)pyrrolidine-1-carboxylate (0.22 g, 0.46 mmol) in DCM (5 mL) was added TFA (0.66 mL, 3 vol) dropwise at 0° C. The mixture was allowed to warm to rt and stirred for 1 h, then concentrated under reduced pressure to yield 4-(5-cyano-2-cyclopropoxyphenyl)-N-((3R,5R)-5-(methoxymethyl)pyrrolidin-3-yl)oxazole-2-carboxamide TFA salt (0.28 g, quantitative yield).

LCMS: Method C1, 1.09 min. MS: ES+383.2.

Step (iii)

4-(5-Cyano-2-cyclopropoxyphenyl)-N-((3R,5R)-1-cyano-5-(methoxymethyl)pyrrolidin-3-yl)oxazole-2-carboxamide To a stirred solution of 4-(5-cyano-2-cyclopropoxyphenyl)-N-((3R,5R)-5-(methoxymethyl)pyrrolidin-3-yl)oxazole-2-carboxamide TFA salt (0.28 g, 0.56 mmol) in THF (5 mL) was added $K_2CO_3$ (0.23 g, 1.69 mmol) at rt and stirred for 5 min. Cyanogen bromide (0.06 g, 0.56 mmol) was added at 0° C. The mixture was stirred at rt for 1 h, then poured into water (50 mL) and extracted with EtOAc (2×50 mL). The combined organic phases were dried over $Na_2SO_4$ and concentrated under reduced pressure. The residue was purified by flash column chromatography (silica gel, 65% EtOAc in n-hexanes) to yield 4-(5-cyano-2-cyclopropoxyphenyl)-N-((3R,5R)-1-cyano-5-(methoxymethyl)pyrrolidin-3-yl)oxazole-2-carboxamide (0.06 g, 0.14 mmol, 31% yield, over two steps).

LCMS: Method H1, 3.01 min; MS: ES+408.2; $^1H$ NMR (400 MHz, DMSO-$d_6$) δ ppm: 9.10 (d, J=7.6 Hz, 1H), 8.52 (s, 1H), 8.38 (s, 1H), 7.91 (d, J=8.4, 2.0 Hz, 1H), 7.64 (d, J=8.8 Hz, 1H), 4.51-4.56 (m, 1H), 4.16-4.23 (m, 1H), 3.88-3.97 (m, 1H), 3.63-3.67 (m, 1H), 3.46-3.56 (m, 2H), 3.38-3.41 (m, 4H), 2.29-2.36 (m, 1H), 1.83-1.90 (m, 1H), 0.92 (br s, 4H). Chiral SFC: Method Y16, 5.11 min.

Example 13

5-(5-Cyano-2-cyclopropoxyphenyl)-N-((3R,5S)-1-cyano-5-methylpyrrolidin-3-yl)oxazole-2-carboxamide

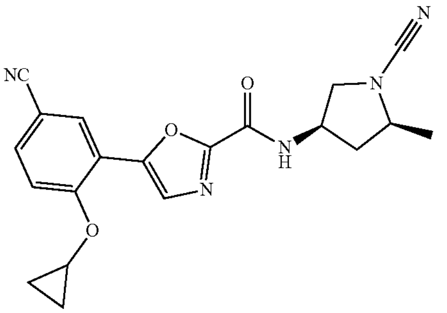 [SMILES: C[C@H]1C[C@@H](NC(=O)c2ncc(-c3cc(C#N)ccc3OC3CC3)o2)CN1C#N]

The title compound may be prepared by an analogous method to Example 1 using tert-butyl (2S,4R)-4-amino-2-methylpyrrolidine-1-carboxylate (CAS 708274-46-8) in Step (i).

Example 14

5-(5-Cyano-2-methoxyphenyl)-N-((3R,5S)-1-cyano-5-methylpyrrolidin-3-yl)oxazole-2-carboxamide

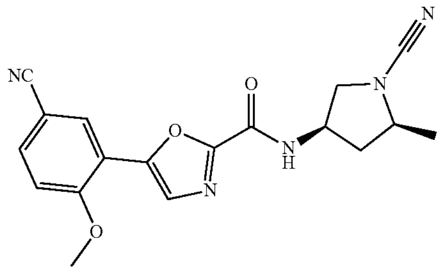 [SMILES: COc1ccc(C#N)cc1-c1cnc(C(=O)N[C@@H]2C[C@H](C)N(C#N)C2)o1]

The title compound may be prepared by an analogous method to Example 4 using tert-butyl (2S,4R)-4-amino-2-methylpyrrolidine-1-carboxylate (CAS 708274-46-8) in Step (i).

Example 15

5-(5-Cyano-2-methoxyphenyl)-N-((3R,5R)-1-cyano-5-(methoxymethyl)pyrrolidin-3-yl)oxazole-2-carboxamide

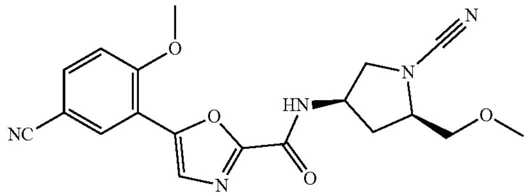 [SMILES: COC[C@H]1C[C@@H](NC(=O)c2ncc(-c3cc(C#N)ccc3OC)o2)CN1C#N]

The title compound may be prepared by an analogous method to Example 5 using tert-butyl (2R,4R)-4-amino-2-(methoxymethyl)pyrrolidine-1-carboxylate (CAS 1123305-98-5) in Step (i).

Example 16

4-(5-Cyano-2-methoxyphenyl)-N-((3R,5R)-1-cyano-5-(methoxymethyl)pyrrolidin-3-yl)oxazole-2-carboxamide

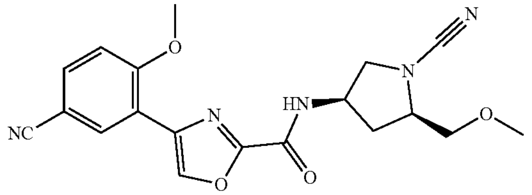 [SMILES: COC[C@H]1C[C@@H](NC(=O)c2nc(-c3cc(C#N)ccc3OC)co2)CN1C#N]

The title compound may be prepared by an analogous method to Example 6 using tert-butyl (2R,4R)-4-amino-2-(methoxymethyl)pyrrolidine-1-carboxylate (CAS 1123305-98-5) in Step (iii).

Example 17

5-(5-Cyano-2-(trifluoromethoxy)phenyl)-N-((3R,5R)-1-cyano-5-(methoxymethyl)pyrrolidin-3-yl)oxazole-2-carboxamide

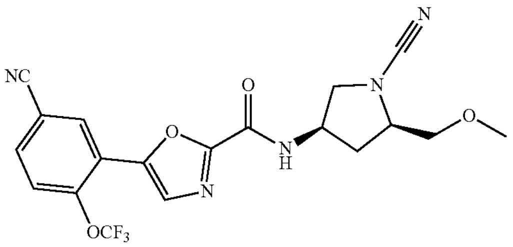 [SMILES: COC[C@H]1C[C@@H](NC(=O)c2ncc(-c3cc(C#N)ccc3OC(F)(F)F)o2)CN1C#N]

The title compound may be prepared by an analogous method to Example 7 using tert-butyl (2R,4R)-4-amino-2-(methoxymethyl)pyrrolidine-1-carboxylate (CAS 1123305-98-5) in Step (i).

Example 18

5-(5-Cyano-2-(trifluoromethoxy)phenyl)-N-((3R,5S)-1-cyano-5-methylpyrrolidin-3-yl)oxazole-2-carboxamide

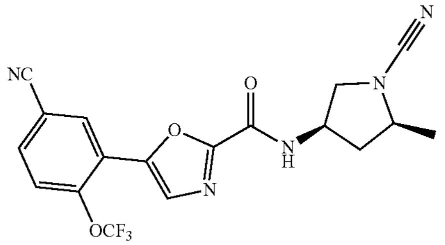 [SMILES: C[C@H]1C[C@@H](NC(=O)c2ncc(-c3cc(C#N)ccc3OC(F)(F)F)o2)CN1C#N]

The title compound may be prepared by an analogous method to Example 8 using tert-butyl (2S,4R)-4-amino-2-methylpyrrolidine-1-carboxylate (CAS 708274-46-8) in Step (i).

Example 19

5-(5-Cyano-4-fluoro-2-methoxyphenyl)-N-((3R,5S)-1-cyano-5-methylpyrrolidin-3-yl)oxazole-2-carboxamide

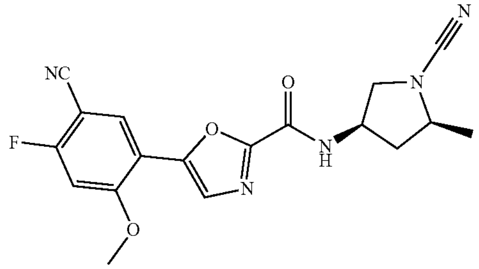 [SMILES: COc1cc(F)c(C#N)cc1-c1cnc(C(=O)N[C@@H]2C[C@H](C)N(C#N)C2)o1]

The title compound may be prepared by an analogous method to Example 9 using tert-butyl (2S,4R)-4-amino-2-methylpyrrolidine-1-carboxylate (CAS 708274-46-8) in Step (i).

Biological Activity of Compounds of the Invention

Abbreviations

| | |
|---|---|
| TAMRA | carboxytetramethylrhodamine |
| PCR | polymerase chain reaction |
| PBS | phosphate buffered saline |
| EDTA | ethylenediaminetetraacetic acid |
| Tris | 2-amino-2-(hydroxymethyl)-1,3-propanediol |
| NP-40 | Nonidet P-40, octylphenoxypolyethoxyethanol |
| BSA | bovine serum albumin |
| PNS | peripheral nervous system |
| BH3 | Bcl-2 homology domain 3 |
| PTEN | phosphatase and tensin homologue |
| SDS-PAGE | Sodium dodecyl sulfate polyacrylamide gel electrophoresis |
| DMSO | Dimethyl sulfoxide |
| YFP | Yellow fluorescent protein |
| VME | Vinyl methyl ester |
| HA | Hemagglutinin |
| Ahx | Aminohexanoic acid |

USP30 Biochemical $IC_{50}$ Assay

Dilution plates were prepared at 21 times the final concentration (2100 μM for a final concentration of 100 μM) in 50% DMSO in a 96-well polypropylene V-bottom plate (Greiner #651201). A typical 8-point dilution series would be 100, 30, 10, 3, 1, 0.3, 0.1, 0.03 μM final. Reactions were performed in duplicate in black 384 well plates (small volume, Greiner 784076) in a final reaction volume of 21 μl. Either 1 μl of 50% DMSO or diluted compound was added to the plate. USP30 (Boston Biochem #E582) was diluted in reaction buffer (40 mM Tris, pH 7.5, 0.005% Tween 20, 0.5 mg/ml BSA, 5 mM beta-mercaptoethanol) to achieve a final assay concentration of 4 nM, and 10 μl of diluted USP30 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2-hour incubation at room temperature. Readings were performed on a Pherastar Plus (BMG Labtech). λ, Excitation 540 nm; λ, Emission 590 nm.

Activity of exemplary compounds in USP30 biochemical $IC_{50}$ assay:

| Example | IC50 (nM) |
|---|---|
| 1 | 3 |
| 2 | 3 |
| 3 | 1 |
| 4 | 2 |
| 5 | 3 |
| 6 | 2 |
| 7 | 3 |
| 8 | 4 |
| 9 | 2 |
| 10 | 4 |
| 11 | 10 |
| 12 | 68 |

Reference Examples

Activity of exemplary compounds in USP30 biochemical $IC_{50}$ assay:

| Reference Example | Structure | Origin | USP30 $IC_{50}$ (nM) |
|---|---|---|---|
| A | 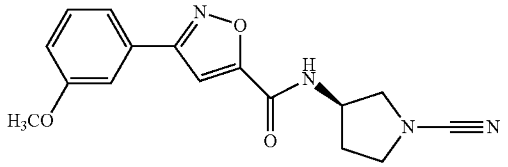 [SMILES: COc1cccc(-c2cc(C(=O)N[C@@H]3CCN(C#N)C3)on2)c1] | WO 2016/156816 Example 221 | 68 |
| B | 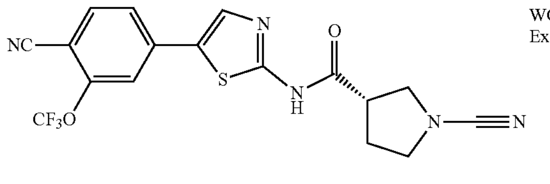 | WO 2016/046530 Example 219 | 172 |
| C | 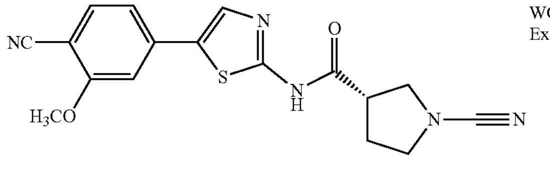 | WO 2016/046530 Example 220 | 160 |
| D | 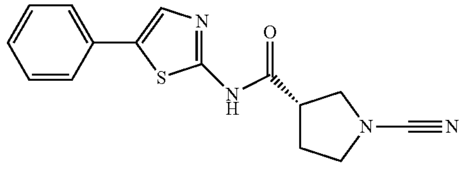 [SMILES: N#CN1CC[C@H](C(=O)Nc2ncc(-c3ccccc3)s2)C1] | WO 2016/046530 Example 1 | 310 |

-continued

| Reference Example | Structure | Origin | USP30 $IC_{50}$ (nM) |
|---|---|---|---|
| E | 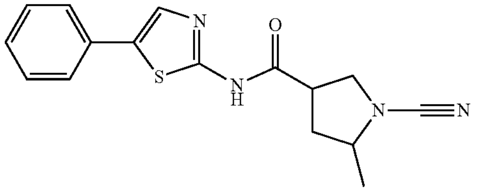 [SMILES: CC1CC(C(=O)Nc2ncc(-c3ccccc3)s2)CN1C#N] | WO 2016/046530 Example 88 | 4400 |

Off-Target Pharmacology

Example 2 was subject to pharmacological profiling in the Eurofins CEREP SafetyScreen44 panel. At a single concentration of 1 μM, less than 50% inhibition of binding or enzyme activity was observed against all targets in the panel. Example 1 has a low probability for off-target interactions due to the low affinity for targets in this assay.

Safety Pharmacology

Example 2 was evaluated for effects on the hERG potassium channel, in stably expressed CHO cells at concentrations between 0.01 and 3 μM. Example 2 produced maximum inhibition value of 35% of the hERG current amplitude at 3 μM indicating little propensity for affecting the QT interval.

Genetic Toxicology

Example 2 was assessed in the bacterial reverse mutation assay (Ames) and in vitro micronucleus assay. All in vitro tests were conducted with and without exogenous metabolic activation using concentrations up to those limited by cytotoxicity or insolubility. Example 2 did not induce mutations when tested up to 5000 g/plate with and without metabolic activation in the reverse mutation assay in *Salmonella typhimurium* strains TA98, TA100, TA1535 and TA97a and the *Escherichia Coli* strain WP2 uvrA pKM101.

Induction of chromosome damage was assessed using the in vitro micronucleus assay in TK6 cells. Example 2 was negative for induction of micronuclei when incubated for 3 hours in the presence of exogenous metabolic activation followed by 27 hours recovery, and also when incubated for 27 hours in the absence of exogenous metabolic activation followed by 27 hours recovery.

USP30 Endogenous Cellular Target Engagement Assay

Hela cells stably overexpressing YFP-Parkin were seeded into 6 well dishes. Once adhered, cells were treated with appropriate concentrations of test compounds or vehicle control for 1 hour at 37° C., 5% $CO_2$. Whole cell lysates were prepared by scraping the cells into cold PBS, centrifuging and lysing in lysis buffer (50 mM Tris-base, pH 7.5, 50 mM NaCl, 1% NP-40/Igepal CA-630, 2 mM $MgCl_2$, 10% Glycerol, 5 mM beta-mercaptoethanol, cOmplete mini tablets EDTA free (Roche), PhosStop tablets (Roche)) for 10 mins. The equivalent of 20 μg of protein from the cleared cell lysate was incubated with a final conc of 2.5 μM HA-Ahx-Ahx-Ub-VME probe at room temperature. The reaction was stopped by addition of 5×SDS sample loading buffer and proteins separated by SDS PAGE and western blotting. USP30 was detected using an anti-USP30 Sheep S746D antibody (MRC PPU Reagents and Services) and a rabbit anti sheep secondary IgG (H+L) horseradish peroxidase conjugated (Thermo #31480) and visualised using ECL reagent (GE #RPN2109) on a GE LAS4000 imager. Target engagement was measured by quantitation of the bands corresponding to USP30 and USP30 bound to the Ub-VME probe and expression of this proportion compared to vehicle treated control.

TOM20-Ubiquitylation Assay

Human cell lines can be challenged with mitochondrial depolarizing agents (ionophores (eg. CCCP, valinomycin), mitochondrial complex inhibitors (oligomycin, antimycin A)) to induce ubiquitylation of TOM20, which is then further promoted in the presence of USP30 inhibitors. TOM20 ubiquitylation is subsequently assessed through western blotting of the cell lysates, with TOM20 ubiquitylation adduct detection possible due to an 8 kDa molecule weight increase for each molecule of ubiquitin added, resulting in laddering of a TOM20 immunoreactive band. TOM20-ubiquitylation levels can be quantified using chemiluminescence densitometry of laddered immunoreactive bands.

In Vitro Cytotoxicity (Cell Tox): Measured in HCT116 human colorectal carcinoma cells using alamarBlue™ as the assay endpoint. Compound cytotoxicity was measured over a period of 96-hour continual compound exposure.

Further Studies log P: partition coefficient; lipophilicity measurement.

log D: distribution co-efficient; lipophilicity measurement.

TPSA: topological polar surface area.

Turbidimetric solubility: Test compound solution prepared in DMSO diluted into aqueous buffer.

Turbidimetry is used as the end-point by measuring absorbance at 620 nm.

FaSSIF: simulated intestinal fluid in fasted state measured at pH 6.5.

Hep Cl mouse: in vitro hepatocyte clearance in mouse cells.

Hep Cl human: in vitro hepatocyte clearance in human cells.

Plasma $f_{u,p}$: The free fraction of a compound in plasma preparation determined by in vitro equilibrium dialysis.

Brain $f_{u,br}$: The free fraction of a compound in brain homogenate preparation determined by in vitro equilibrium dialysis.

$Cl_u$: in vitro clearance. $Cl_u$ as defined here is the scaled clearance, in turn calculated from the intrinsic clearance. The intrinsic clearance is the predicted clearance due to hepatic metabolic reactions, determined from incubation of a compound in a hepatocyte preparation. The lower the value in mL/min/kg, the more stable the compound.

Cl in vivo clearance: Pharmacokinetic measurement of the volume of plasma (or any matrix) from which a substance is completely removed per unit time. The lower the value in mL/min/kg, the more stable the compound.

Oral F: Oral bioavailability.

MDR1-MDCK (Madin-Darby Canine Kidney cell monolayer) (in vitro) flux assay.

WT-MDCK (wild-type) in vitro flux.

$Kp_{uu}$ is the ratio of unbound drug in brain to unbound drug in plasma and may be indicative of potential for treating peripheral and/or CNS indications.

| Studies | | Example 1 | Example 2 |
|---|---|---|---|
| Cell TE WB | Endogenous USP30 $EC_{50}$ (μM) | 0.002 | 0.003 |
| Cell Tox | HCT116 $EC_{50}$ (μM) | 23.8 | 27.1, >30 |
| Physico-chemical | Log D measured at pH 7.4 | 2.5 | 2.2 |
| | TPSA | 116 | 125 |
| | Turbidimetric solubility (μM) | 65 | >100 |
| | FaSSIF (μM) measured at pH 6.5 | — | 34 |
| Hepatocyte Cl mouse | Scaled $Cl_u$ (mL/min/kg) | 117 | 105 |
| Hepatocyte Cl human | Scaled $Cl_u$ (mL/min/kg) | 18.6 | 5.0 |
| Stability | Mouse plasma $t_{1/2}$ (min) | >120 | >120 |
| MDR1-MDCK | Effective Efflux Ratio | — | 15 |
| WT-MDCK | Efflux Ratio (A-B Papp flux ($10^{-6}$ cm/s)) | — | 0.7 (10.7) |

| Studies | | Example 1 | Example 2 |
|---|---|---|---|
| Binding Mouse | Plasma $f_{u,p}$/Brain $f_{u,br}$ | 0.09/0.06 | 0.07/0.20 |
| PK mouse 2 mg/kg iv | Cl plasma (mL/min/kg) | 41 | 20 |
| PK mouse 10 mg/kg | Oral F (%) | 37 | 47 |

-continued

| Studies | | Example 1 | Example 2 |
|---|---|---|---|
| TOM20-Ub 1.5-fold gain | Antimycin A/oligomycin mitophagy trigger EC1.5x (μM) | 0.006 | 0.007 |
| Unbound plasma Cmax/TOM20-Ub cell potency (10 mg/kg po dose - mouse) | | 45 | 140 |
| $Kp_{uu}$ | 2 mg/kg IV dose - mouse | 0.02 | 0.01 |

The examples possess beneficial properties demonstrating potential superiority over other compounds. For instance, for Examples 1 and 2, the observed IV plasma clearance of 41 and 20 mL/min/kg, respectively, as measured in the mouse, is low, demonstrating valuable plasma stability, and the compounds have very good oral bioavailability of 37 and 47%, respectively.

| Compound | | Ex. 1 | Ex. 2 | Ex. 4 | Ex. 6 |
|---|---|---|---|---|---|
| DUB $IC_{50}$ (μM) | USP30 | 0.003 | 0.003 | 0.002 | 0.002 |
| DUB $IC_{50}$ (μM) | USP2, USP6, USP10, USP15, USP16, USP21, USP25, USP28, USP46/UAF1 | 1.2-80 | 1.1-130 | 1.0->300 | 1.4-258 |
| DUB selectivity preference for USP30 v 9 DUBs | | ≥400 | ≥367 | ≥500 | ≥700 |

| Compound | | Ex. 1 | Ex. 2 | Ex. 4 | Ex. 6 |
|---|---|---|---|---|---|
| Cathepsin $IC_{50}$ (μM) | Cathepsin B | 106.6 | >300 | >300 | 52.1 |
| | Cathepsin K | 10.5 | 18.9 | 164.8 | 40.4 |
| | Cathepsin L | 9.9 | 23.6 | 294.3 | 39.8 |
| | Cathepsin S | 54.4 | 91.2 | >300 | 64.8 |
| | Cathepsin V | 30.9 | 60.6 | >300 | 91.6 |
| | B, K, L, S, V | ≥9.9 | ≥18.9 | ≥164.8 | ≥39.8 |
| Selectivity preference for USP30 v cathepsins | | ≥3300 | ≥6300 | ≥82400 | ≥19900 |

| Compound | | Ex. 7 | Ex. 11 | Ex. 12 | Ref. Ex. A |
|---|---|---|---|---|---|
| DUB $IC_{50}$ (μM) | USP30 | 0.003 | 0.010 | 0.068 | 0.068 |
| DUB $IC_{50}$ (μM) | USP2, USP6, USP10, USP15, USP16, USP21, USP25, USP28, USP46/UAF1 | 4.0->300 (exc. USP15) | 78.2->300 | 7.5->300 | 0.15-22.4 |
| DUB selectivity preference for USP30 v 9 DUBs | | ≥1333 | ≥7820 | ≥110 | ≥2.2 |

| Compound | | Ex. 7 | Ex. 11 | Ex. 12 | Ref. Ex. A |
|---|---|---|---|---|---|
| Cathepsin $IC_{50}$ (μM) | Cathepsin B | 60.9 | 83.0 | >300 | 4.5 |
| | Cathepsin K | 14.9 | 100.2 | >300 | 0.79 |
| | Cathepsin L | 13.8 | 15.4 | >300 | 2.9 |
| | Cathepsin S | >30 | 129.7 | >300 | 8.8 |
| | Cathepsin V | 12.1 | >100 | 189.6 | 5.8 |
| | B, K, L, S, V | ≥12.1 | ≥15.4 | ≥189 | 0.79-8.8 |
| Selectivity preference for USP30 v cathepsins | | ≥4033 | ≥1540 | ≥2788 | 11.6-129 |

| Compound | | Exs. 1, 2, 4, 6, 7, 11 | Ex. 12 | Ref. Ex. B | Ref. Ex. C | Ref. Ex. D | Ref. Ex. E |
|---|---|---|---|---|---|---|---|
| DUB | USP30 | 0.002-0.010 | 0.068 | 0.172 | 0.160 | 0.31 | 4.4 |
| $IC_{50}$ (μM) | UCHL1 | >300 | >300 | 0.52 | 0.21 | 0.25 | 6.8 |
| DUB selectivity preference for USP30 v UCHL1 | | >30000 | >4412 | 3.0 | 1.3 | 0.8 | 1.5 |

Comparative Data

Reference Examples A, B, C, D and E are known DUB inhibitors that have been identified as active as inhibitors of USP30 and share some structural similarity with the compounds of the present invention, possessing the cyanamide structural feature. Reference Examples B, C, D and E are disclosed in WO 2016/046530 as having UCHL1 inhibitory activity.

Potency for USP30

Examples 1 to 11 of the present invention are significantly more potent against USP30 than Reference Examples A, B, C, D and E, as measured in the biochemical assay. Example 12 is significantly more potent against USP30 than Reference Examples B, C, D and E. For instance, Examples 1 to 11 are to 6.8 to 34-fold more potent than Reference Example A, 16 to 155-fold more potent than Reference Examples B, C and D, and at least 440-fold more potent than Reference Example E.

Selectivity for USP30 Over Other DUBs

The data provided demonstrates that Examples 1, 2, 4, 6, 7, 11 and 12 are significantly more selective for USP30 over nine DUBs (USP2, USP6, USP10, USP15, USP16, USP21, USP25, USP28 and USP46) compared to Reference Example A. These examples are, at a minimum, between 110 and 7820-fold more potent against USP30 than against each of the nine DUBs (Example 7 not tested against USP15). This is a significant selectivity advantage over Reference Example A, which is as low as 2.2-fold more potent.

Selectivity for USP30 over UCHL1

The data provided demonstrates that Examples 1, 2, 4, 6, 7, 11 and 12 are significantly more selective for USP30 over UCHL1 compared to Reference Examples B, C, D and E. Examples 1, 2, 4, 6, 7, 11 are greater than 30000-fold more potent against USP30 than UCHL1, with Example 12 greater than 4412-fold more potent, whereas Reference Examples B, C, D and E are only 3.0, 1.3, 0.8 and 1.5-fold more potent, respectively; 'C' is more selective for UCHL1.

Selectivity for USP30 Over Cathepsins B, K, L, S and V

The data provided demonstrates that Examples 1, 2, 4, 6, 7, 11 and 12 are significantly more selective for USP30 over the cathepsins (B, K, L, S and V) compared to Reference Example A. These examples are all greater than 1540-fold more potent against USP30 than against each of the cathepsins. This is a significant selectivity advantage over Reference Example A, which against cathepsin K is only 11.6-fold more potent.

The above-identified advantages of the compounds of the invention over the reference examples of the prior art are both significant and unexpected. On their own, and in particular in combination, this superiority makes the compounds of the invention particularly suitable for use in the treatment or prevention of diseases linked to USP30 activity.

Preclinical In Vitro Model (a) Human renal proximal tubule cell cisplatin injury model, modified for testing renal protective agents.

Primary human PTCs are isolated from kidneys rejected for transplant.

Isolated cells were seeded on to 96-well Transwell inserts (surface area=0.143 $cm^2$), at a density of 20,000 cells per insert. The medium was refreshed after 24 hours of initial seeding, and also at day 3 and 5 of culture.

Monolayers demonstrated TEERs in a range of 80-120 $\Omega\cdot cm^2$ before used in experiments.

Human PTC monolayers were pre-exposed to Example 2 (0.01, 0.03, 0.1, 0.3, 1.0 and 3.0 μM) for 1 hour to both the apical and basolateral side of the cell layer before exposing the cells to cisplatin (20 μM). Subsequently, cells were exposed to both Example 2 (0.01, 0.03, 0.1, 0.3, 1.0 and 3.0 μM) and cisplatin (20 μM) to both the apical and basolateral side for 24 and 48 hours. In addition, negative controls (Example 2 only, 0.5% DMSO for Example 2, 0.2% dimethyl formamide (DMF) for cisplatin solvent control, a positive control (cisplatin 20 μM), and cisplatin plus an inhibitor of cisplatin uptake (dolutegravir 100 μM) were included in parallel. Experiments were performed in triplicate in human cell monolayers (n=3) and in three different donors (N=3).

Cell viability assays based on ATP production and LDH release were performed on test compound-treated monolayers performed in 96-well Transwell inserts.

Example 2 protected against cisplatin-induced loss of ATP in a concentration dependent manner. Example 2 also reduced cisplatin-induced LDH elevation. These data demonstrate that Example 2 can protect against cisplatin-induced toxicity to human proximal tubule epithelial cells.

Preclinical In Vivo Models

Compounds of the invention may be tested for efficacy in representative in vivo disease models, using standard study procedures from the published literature, including, for example:

(a) Bleomycin-induced lung fibrosis model, which is a leading preclinical in vivo model of Idiopathic Pulmonary Fibrosis. [Kobayashi et al, 2016, J Immunol, 197(2):504-516].

(b) Diet-induced model of NAFLD and glucose homeostasis. [Nishida et al, 2013, Lab Invest; February; 93(2):230-41].

(c) MPTP Model of Parkinson's Disease, which is a commonly used paradigm for looking at neurodegeneration in the dopaminergic system of the brain which is triggered by chemically-induced mitochondrial dysfunction. [Karuppagouner et al, 2014, Sci Rep. 2014 May 2; 4:4874].

(d) Ndufs4KO Leigh syndrome model. [Kruse et al, 2008, Cell Metab. April; 7(4):312-20].

(e) Aged rodent model: effects on hippocampal, cognitive and motor function. [Kobilo et al, 2014, Learn Mem. January 17; 21(2):119-26; Creed et al, 2019, Neuroscience. June 15; 409:169-179; Van Skike et al, 2020, Aging Cell. 19; e13057].

(f) The unilateral ureteral obstructive kidney disease model (UUO). [Chevalier et al, 2009, Kidney Int 75(11): 1145-1152].

UUO causes renal injury characterised by tubular cell injury, interstitial inflammation and fibrosis. It serves as a model of irreversible post-renal acute kidney injury (AKI). Experimental UUO has illustrated the molecular mechanisms of apoptosis, inflammation and fibrosis, all of which are key processes in renal injury, regardless of the primary insult. Consequently, the UUO model provides investigators information beyond obstruction (Chevalier et al, 2009, Kidney Int 75(11): 1145-1152).

Example 2 was assessed in the UUO model to determine the ability of the compound to attenuate progressive tubulointerstitial fibrosis and chronic kidney disease (CKD).

On day 1 of the study, adult C57BL/6 mice were dosed by oral gavage according to one of the following dosing regimens; Vehicle, 5 or 1.5 mg/kg Example 2 BID. Two hours post dosing on day 1 study mice underwent surgery to ligate the left ureter at two points. Successful UUO surgery was later confirmed by observation of dilation of renal pelvis due to hydronephrosis. The animals were dosed according to their prescribed regimen for 10 days at which point kidneys were harvested, or histopathology assessment and for protein/RNA assessment. Picrosirius Red staining was performed to assess the extent of collagen deposition and IHC was employed to assess relative α-Smooth Muscle Actin (α-SMA) expression.

Results demonstrated that 5 and 1.5 mg/kg Example 2 (p.o.) dosed BID, statistically reduced collagen deposition as evidenced by reduced picrosirius red staining in ligated kidneys. Assessment of α-SMA staining, revealed that oral dosing of 5 and 1.5 mg/kg Example 2 BID resulted in a statistical reduction in α-SMA levels in UUO injured kidneys when compared to vehicle treated controls.

(g) AKI can be induced by bilateral renal pedical clamping resulting in ischemia reperfusion injury (IRI) resulting in severe loss of renal function tubular damage and inflammation [Lu et al. 2012. J Nephrol. 25 (5): 738-45].

Prophylactic Administration:

Example 2 was administered to C57BL/6 mice 5 and 1.5 mg/kg BID (p.o.) and compared to vehicle treatment from Day −1 through to Day +21. On Day 0, mice were anaesthetized, and their left renal pedicle clamped for 45 min, then released to induce IRI. On Day Day +21 kidneys were harvested. Morphology and fibrosis were assessed.

Body weight was similar between groups and remained constant throughout the observation periods. Masson trichome stain revealed significantly less tubular atrophy and collagen content in the outer medulla from Example 2 treated animals (both dose levels) on Day +21. Fibronectin expression in the cortex and outer medulla was significantly reduced in Example 2 treated animals (both dose levels) on Day +21.

Example 2 demonstrated efficacy in this model of IR-induced CKD. Daily treatment has shown significant benefits of attenuated tubular atrophy and reduced fibrosis.

Post-Injury Administration:

On Day 0 (zero) C57BL/6 mice were anaesthetized, and their left renal pedicle clamped for 45 min, then released to induce IRI. Mice were then administered either vehicle or Example 2; 5 mg/kg (p.o.) BID for 21 days, with first treatment starting five hours following IRI surgery (i.e. therapeutics dosing). Mice were monitored and kidneys harvested at Day +21. Kidney sections were quantitatively assessed for relative cellular morphology and fibrosis using blinded histological scoring methods.

Body weight was similar between groups and remained constant throughout the observation periods. Fibronectin staining in the cortex was significantly reduced in Example 2 treated mice on Day +21.

Example 2 demonstrated partial efficacy in this model of IR-induced CKD when dosed therapeutically. Initiating treatment after the establishment of ischemia-reperfusion injury has shown significant benefits towards reduced cortical fibrosis.

Paragraphs of the Invention

The present invention is directed to the following:

1. A compound of formula (I), which is selected from formula (I)(i) and formula (I)(ii):

(I)(i)

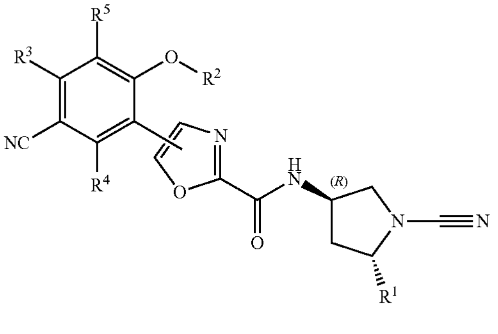

-continued (I)(ii)

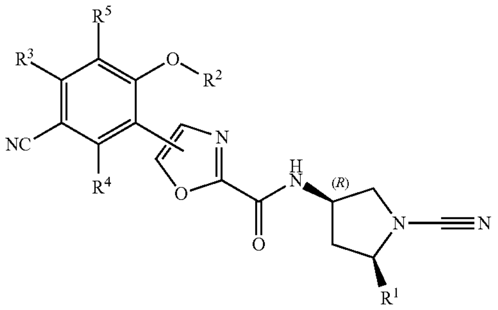

a tautomer thereof, or a pharmaceutically acceptable salt of said compound or tautomer, wherein:

$R^1$ is selected from $(C_1\text{-}C_4)$alkyl, $(C_1\text{-}C_4)$fluoroalkyl and $CH_2OCH_3$;

$R^2$ is selected from $(C_1\text{-}C_4)$alkyl, $CF_3$ and cyclopropyl; and $R^3$, $R^4$ and $R^5$ are each independently selected from hydrogen and halogen.

2. The compound according to paragraph 1, wherein $R^1$ is selected from methyl, $CH_2F$, $CHF_2$, $CF_3$ and $CH_2OCH_3$.

3. The compound according to paragraph 2, wherein $R^1$ is selected from methyl and $CH_2OCH_3$.

4. The compound according to any one of paragraphs 1 to 3, wherein $R^2$ is selected from methyl, $CF_3$ and cyclopropyl.

5. The compound according to paragraph 4, wherein $R^2$ is selected from methyl and cyclopropyl.

6. The compound according to any one of paragraphs 1 to 5, wherein $R^3$ is selected from hydrogen and fluorine.

7. The compound according to paragraph 6, wherein $R^3$ is hydrogen.

8. The compound according to any one of paragraphs 1 to 7, wherein $R^4$ and $R^5$ are each hydrogen.

9. The compound according to any one of paragraphs 1 to 8, having the formula (I)(i):

(I)(i)

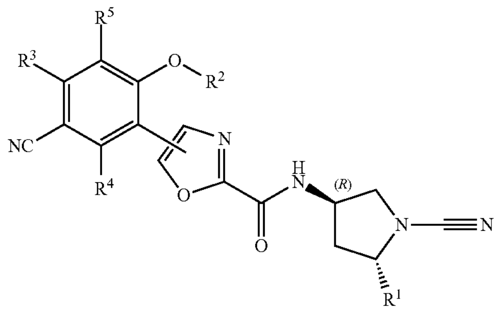

a tautomer thereof, or a pharmaceutically acceptable salt of said compound or tautomer.

10. The compound according to paragraph 9, having the formula (IA)(i):

(IA)(i)

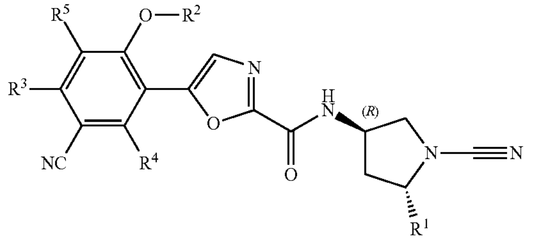

a tautomer thereof, or a pharmaceutically acceptable salt of said compound or tautomer.

11. The compound according to paragraph 10, which is selected from:

5-(5-cyano-2-cyclopropoxyphenyl)-N-((3R,5R)-1-cyano-5-methylpyrrolidin-3-yl)oxazole-2-carboxamide;

5-(5-cyano-2-cyclopropoxyphenyl)-N-((3R,5S)-1-cyano-5-(methoxymethyl)pyrrolidin-3-yl)oxazole-2-carboxamide;

5-(5-cyano-2-cyclopropoxyphenyl)-N-((3R,5S)-1-cyano-5-(fluoromethyl)pyrrolidin-3-yl)oxazole-2-carboxamide;

5-(5-cyano-2-methoxyphenyl)-N-((3R,5R)-1-cyano-5-methylpyrrolidin-3-yl)oxazole-2-carboxamide;

5-(5-cyano-2-methoxyphenyl)-N-((3R,5S)-1-cyano-5-(methoxymethyl)pyrrolidin-3-yl)oxazole-2-carboxamide;

5-(5-cyano-2-(trifluoromethoxy)phenyl)-N-((3R,5S)-1-cyano-5-(methoxymethyl)pyrrolidin-3-yl)oxazole-2-carboxamide;

5-(5-cyano-2-(trifluoromethoxy)phenyl)-N-((3R,5R)-1-cyano-5-methylpyrrolidin-3-yl)oxazole-2-carboxamide; and 5-(5-cyano-4-fluoro-2-methoxyphenyl)-N-((3R,5R)-1-cyano-5-methylpyrrolidin-3-yl)oxazole-2-carboxamide;

or a pharmaceutically acceptable salt thereof.

12. The compound according to paragraph 9, having the formula (IB)(i):

(IB)(i)

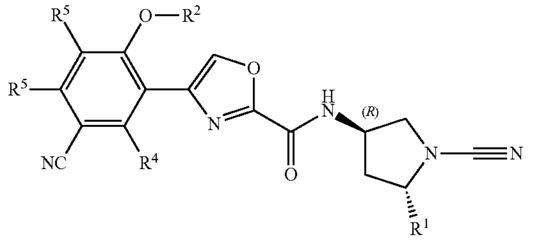

a tautomer thereof, or a pharmaceutically acceptable salt of said compound or tautomer.

13. The compound according to paragraph 12, which is selected from:

4-(5-cyano-2-methoxyphenyl)-N-((3R,5S)-1-cyano-5-(methoxymethyl)pyrrolidin-3-yl)oxazole-2-carboxamide and 4-(5-cyano-2-cyclopropoxyphenyl)-N-((3R,5S)-1-cyano-5-(methoxymethyl)pyrrolidin-3-yl)oxazole-2-carboxamide;

or a pharmaceutically acceptable salt thereof.

14. The compound according to any one of paragraphs 1 to 8, having the formula (I)(ii):

(I)(ii)

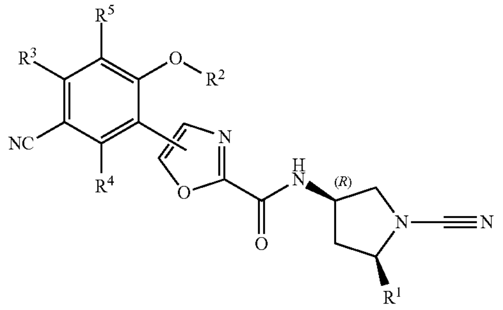

a tautomer thereof, or a pharmaceutically acceptable salt of said compound or tautomer.

15. The compound according to paragraph 14, having the formula (IA)(ii):

(IA)(ii)

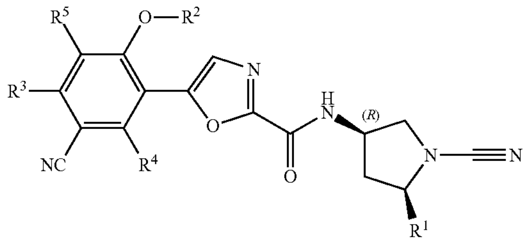

a tautomer thereof, or a pharmaceutically acceptable salt of said compound or tautomer.

16. The compound according to paragraph 15, which is selected from:

5-(5-cyano-2-cyclopropoxyphenyl)-N-((3R,5R)-1-cyano-5-(methoxymethyl)pyrrolidin-3-yl)oxazole-2-carboxamide;

5-(5-cyano-2-cyclopropoxyphenyl)-N-((3R,5S)-1-cyano-5-methylpyrrolidin-3-yl)oxazole-2-carboxamide;

5-(5-cyano-2-methoxyphenyl)-N-((3R,5S)-1-cyano-5-methylpyrrolidin-3-yl)oxazole-2-carboxamide;

5-(5-cyano-2-methoxyphenyl)-N-((3R,5R)-1-cyano-5-(methoxymethyl)pyrrolidin-3-yl)oxazole-2-carboxamide;

5-(5-cyano-2-(trifluoromethoxy)phenyl)-N-((3R,5R)-1-cyano-5-(methoxymethyl)pyrrolidin-3-yl)oxazole-2-carboxamide;

5-(5-cyano-2-(trifluoromethoxy)phenyl)-N-((3R,5S)-1-cyano-5-methylpyrrolidin-3-yl)oxazole-2-carboxamide;

5-(5-cyano-4-fluoro-2-methoxyphenyl)-N-((3R,5S)-1-cyano-5-methylpyrrolidin-3-yl)oxazole-2-carboxamide; and 5-(5-cyano-2-cyclopropoxyphenyl)-N-((3R,5R)-1-cyano-5-(fluoromethyl)pyrrolidin-3-yl)oxazole-2-carboxamide;

or a pharmaceutically acceptable salt thereof.

17. The compound according to paragraph 14, having the formula (IB)(ii):

(IB)(ii)

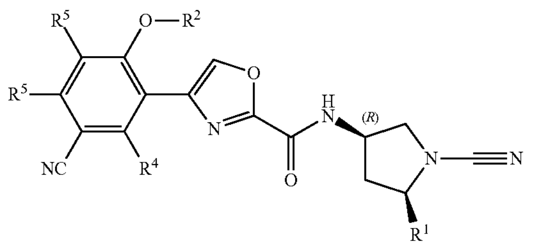

a tautomer thereof, or a pharmaceutically acceptable salt of said compound or tautomer.

18. The compound according to paragraph 17, which is selected from:

4-(5-cyano-2-cyclopropoxyphenyl)-N-((3R,5R)-1-cyano-5-(methoxymethyl)pyrrolidin-3-yl)oxazole-2-carboxamide; and 4-(5-cyano-2-methoxyphenyl)-N-((3R,5R)-1-cyano-5-(methoxymethyl)pyrrolidin-3-yl)oxazole-2-carboxamide;

or a pharmaceutically acceptable salt thereof.

19. A compound according to any one of paragraphs 1 to 18, a tautomer thereof, or a pharmaceutically acceptable salt of said compound or tautomer, for use as a medicament.

20. A compound according to any one of paragraphs 1 to 18, a tautomer thereof, or a pharmaceutically acceptable salt of said compound or tautomer, for use in the treatment or prevention of a condition involving mitochondrial dysfunction, a cancer, or fibrosis.

21. Use of a compound according to any one of paragraphs 1 to 18, a tautomer thereof, or a pharmaceutically acceptable salt of said compound or tautomer, in the manufacture of a medicament for use in the treatment or prevention of a condition involving mitochondrial dysfunction, a cancer, or fibrosis.

22. A method for the treatment or prevention of a condition involving mitochondrial dysfunction, a cancer, or fibrosis, comprising the step of administering an effective amount of a compound according to any one of paragraphs 1 to 18, a tautomer thereof, or a pharmaceutically acceptable salt of said compound or tautomer, to a patient in need thereof.

23. The compound, use, or method, according to paragraphs 20 to 22, wherein the condition involving mitochondrial dysfunction is selected from a CNS disorder; neurodegenerative disease; Parkinson's disease; Alzheimer's disease; amyotrophic lateral sclerosis; Huntington's disease; ischemia; stroke; dementia with Lewy bodies; frontotemporal dementia; multiple sclerosis; mitochondrial encephalopathy, lactic acidosis and stroke-like episodes syndrome; materially-inherited diabetes and deafness; Leber's hereditary optic neuropathy; neuropathy, ataxia, retinitis pigmentosa-maternally inherited Leigh syndrome; Danon disease; diabetes; diabetic nephropathy; metabolic disorders; heart failure; ischemic heart disease leading to myocardial infarction; psychiatric diseases, schizophrenia; multiple sulfatase deficiency; mucolipidosis II; mucolipidosis III; mucolipidosis IV; GM1-gangliosidosis; neuronal ceroid-lipofuscinoses; Alpers disease; Barth syndrome; beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome; CPT I deficiency; CPT II deficiency; glutaric aciduria type II; Kearns-Sayre syndrome; lactic acidosis; long-chain acyl-CoA dehydrogenase deficiency; Leigh disease or syndrome; Leigh syndrome French Canadian variant; lethal infantile cardiomyopathy; Luft disease; medium-chain acyl-CoA dehydrogenase deficiency; myoclonic epilepsy and ragged-red fiber syndrome; mitochondrial cytopathy; mitochondrial recessive ataxia syndrome; mitochondrial DNA depletion syndrome; myoneurogastrointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase deficiency; very long-chain acyl-CoA dehydrogenase deficiency; peroxisomal disorders; methylmalonic acidemia; mevalonate kinase deficiency; age-dependent decline in cognitive function and muscle strength; and cognitive impairment associated with all neurodegenerative and neuropsychiatric disorders.

24. The compound, use, or method, according to paragraph 23, wherein the neurodegenerative disease is selected from Parkinson's disease, Alzheimer's disease, amyotrophic lateral sclerosis, Huntington's disease, ischemia, stroke, dementia with Lewy bodies, multiple system atrophy, progressive supranuclear palsy, corticobasal degeneration, frontotemporal dementia; and Parkinson's disease related to mutations in α-synuclein, parkin, PINK1, GBA, and LRRK2, and autosomal recessive juvenile Parkinson's disease or early onset Parkinson's disease (EOPD), where parkin or PINK1 is mutated, truncated or deleted.

25. The compound, use, or method, according to paragraph 23, wherein the neurodegenerative disease is Leigh syndrome or disease, X-linked Leigh's disease, Leigh syndrome French Canadian variant, and/or the symptoms associated with Leigh's disease.

26. The compound, use, or method, according to paragraphs 20 to 22, wherein the cancer is selected from breast, ovarian, prostate, lung, kidney, gastric, colon, testicular, head and neck, pancreas, brain, melanoma, bone, liver, soft tissue, cancers of tissue organs, cancers of the blood cells, CML, AML, mantle cell lymphoma, neuroblastoma, melanoma, soft tissue sarcoma, liposarcoma, fibroblastic sarcoma, leiomyosarcoma, hepatocellular carcinoma, osteosarcoma, oesophageal cancer, leukaemia, lymphoma, multiple myeloma, metastatic carcinoma, osteosarcoma, chondosarcoma, Ewing's sarcoma, nasopharyngeal carcinoma, colorectal cancer, colorectal cancer, non-small cell lung carcinoma, cancer where apoptotic pathways are dysregulated, and cancer where proteins of the BCL-2 family are mutated, or over or under expressed.

27. The compound, use, or method, according to paragraphs 20 to 22, wherein the fibrosis is selected from fibrosis or a fibrotic disorder associated with the accumulation of extracellular matrix constituents that occurs following trauma, inflammation, tissue repair, immunological reactions, cellular hyperplasia, and neoplasia.

28. The compound, use, or method, according to paragraph 27, wherein the fibrosis is selected from fibrosis or a fibrotic disorder associated with major organ diseases, fibroproliferative disorders, and scarring associated with trauma.

29. The compound, use, or method, according to paragraph 28, wherein the fibrosis is selected from fibrosis or a fibrotic disorder associated with interstitial lung disease, liver cirrhosis, non-alcoholic fatty liver disease, non-alcoholic fatty liver disease, and non-alcoholic steatohepatitis, kidney disease, acute kidney disease, acute kidney injury, chronic kidney disease, delayed kidney graft function, heart or vascular disease, diseases of the eye, systemic and local scleroderma, keloids, hypertrophic scars, atherosclerosis, restenosis, Dupuytren's contracture, surgical complications, chemotherapeutics drug-induced fibrosis, radiation-induced fibrosis, accidental injury and burns, retroperitoneal fibrosis, and peritoneal fibrosis/peritoneal scarring.

30. The compound, use, or method, according to paragraph 29, wherein the fibrosis associated with interstitial lung disease is selected from sarcoidosis, silicosis, drug reactions, infections, collagen vascular diseases, rheumatoid arthritis, systemic sclerosis, scleroderma, pulmonary fibrosis, idiopathic pulmonary fibrosis, usual interstitial pneumonitis, interstitial lung disease, cryptogenic fibrosing alveolitis, bronchiolitis obliterans, and bronchiectasis.

31. The compound, use, or method, according to paragraph 29, wherein the kidney disease is acute kidney disease, acute kidney injury or chronic kidney disease.

32. A pharmaceutical composition comprising a compound of formula (I) as defined in any one of paragraphs 1 to 18, a tautomer thereof, or a pharmaceutically acceptable salt of said compound or tautomer, together with one or more pharmaceutically acceptable excipients.

33. A compound, which is selected from formulae (II)(i), (III)(i), (II)(ii) and (III)(ii):

(II)(i)

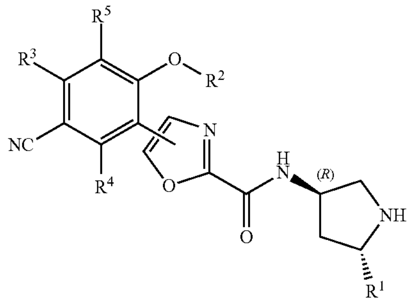

(III)(i)

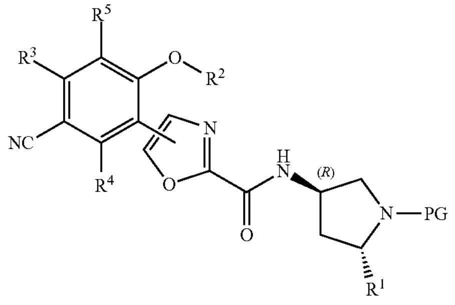

(II)(ii)

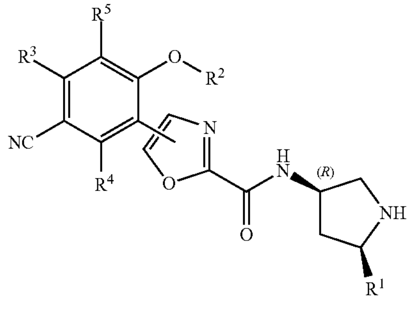

-continued (III)(ii)

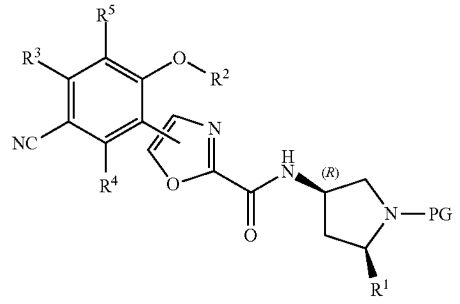

a tautomer thereof, or a salt of said compound or tautomer; wherein $R^1$, $R^2$, $R^3$, $R^4$ and $R^5$ are as defined for the compound of formula (I) in any one of paragraphs 1 to 18; and PG is a protecting group, which is preferably selected from tert-butyloxycarbonyl, benzyloxycarbonyl, p-methoxybenzyl carbonyl, 9-fluorenylmethyloxycarbonyl, acetyl, benzoyl, benzyl, carbamate, p-methoxybenzyl, 3,4-dimethoxybenzyl, p-methoxyphenyl, tosyl, trichloroethoxycarbonyl, 4-nitrobenzenesulfonyl and 2-nitrophenylsulfenyl.

The invention claimed is:

1. A compound of formula (I), which is selected from formula (I)(i) and formula (I)(ii):

(I)(i)

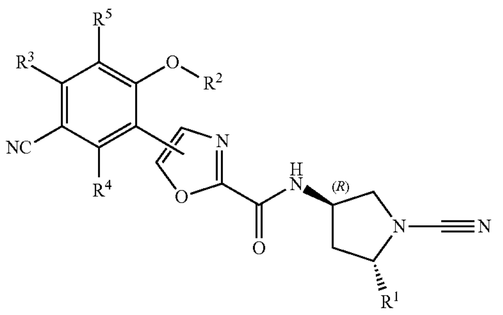

(I)(ii)

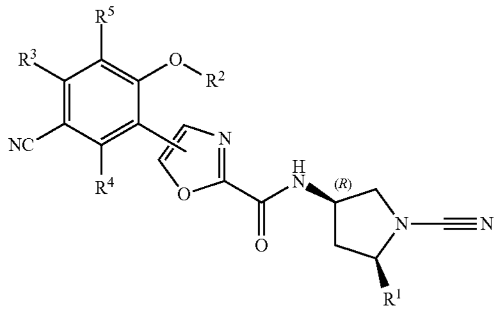

or a tautomer thereof, or a pharmaceutically acceptable salt of said compound or tautomer, wherein:

$R^1$ is selected from $(C_1-C_4)$alkyl, $(C_1-C_4)$fluoroalkyl and $CH_2OCH_3$;

$R^2$ is selected from $(C_1-C_4)$alkyl, $CF_3$ and cyclopropyl; and $R^3$, $R^4$ and $R^5$ are each independently selected from hydrogen and halogen.

2. The compound according to claim 1, wherein $R^1$ is selected from methyl, $CH_2F$, $CHF_2$, $CF_3$ and $CH_2OCH_3$.

3. The compound according to claim 2, wherein $R^1$ is selected from methyl and $CH_2OCH_3$.

4. The compound according to claim 1, wherein $R^2$ is selected from methyl, $CF_3$ and cyclopropyl.

5. The compound according to claim 4, wherein $R^2$ is selected from methyl and cyclopropyl.

6. The compound according to claim 1, wherein $R^3$ is selected from hydrogen and fluorine.

7. The compound according to claim 6, wherein $R^3$ is hydrogen.

8. The compound according to claim 1, wherein $R^4$ and $R^5$ are each hydrogen.

9. The compound according to claim 1, having the formula (I)(i):

(I)(i)

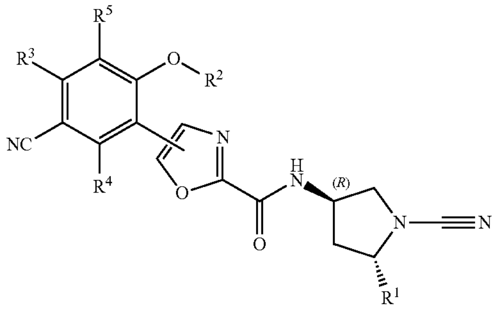

or a tautomer thereof, or a pharmaceutically acceptable salt of said compound or tautomer.

10. The compound according to claim 9, having the formula (IA)(i):

(IA)(i)

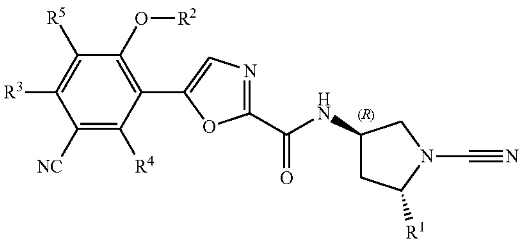

or a tautomer thereof, or a pharmaceutically acceptable salt of said compound or tautomer.

11. The compound according to claim 10, which is selected from:

5-(5-cyano-2-cyclopropoxyphenyl)-N-((3R,5R)-1-cyano-5-methylpyrrolidin-3-yl)oxazole-2-carboxamide;

5-(5-cyano-2-cyclopropoxyphenyl)-N-((3R,5S)-1-cyano-5-(methoxymethyl)pyrrolidin-3-yl)oxazole-2-carboxamide;

5-(5-cyano-2-cyclopropoxyphenyl)-N-((3R,5S)-1-cyano-5-(fluoromethyl)pyrrolidin-3-yl)oxazole-2-carboxamide;

5-(5-cyano-2-methoxyphenyl)-N-((3R,5R)-1-cyano-5-methylpyrrolidin-3-yl)oxazole-2-carboxamide;

5-(5-cyano-2-methoxyphenyl)-N-((3R,5S)-1-cyano-5-(methoxymethyl)pyrrolidin-3-yl)oxazole-2-carboxamide;

5-(5-cyano-2-(trifluoromethoxy)phenyl)-N-((3R,5S)-1-cyano-5-(methoxymethyl)pyrrolidin-3-yl)oxazole-2-carboxamide;

5-(5-cyano-2-(trifluoromethoxy)phenyl)-N-((3R,5R)-1-cyano-5-methylpyrrolidin-3-yl)oxazole-2-carboxamide; and 5-(5-cyano-4-fluoro-2-methoxyphenyl)-N-((3R,5R)-1-cyano-5-methylpyrrolidin-3-yl)oxazole-2-carboxamide;

or a pharmaceutically acceptable salt thereof.

12. The compound according to claim 9, having the formula (IB)(i):

(IB)(i)

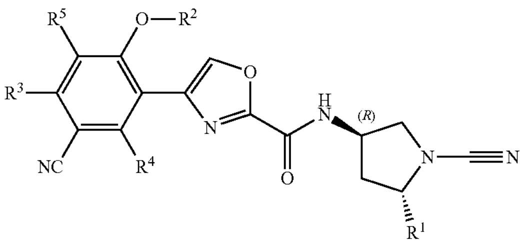

or a tautomer thereof, or a pharmaceutically acceptable salt of said compound or tautomer.

13. The compound according to claim 12, which is selected from:

4-(5-cyano-2-methoxyphenyl)-N-((3R,5S)-1-cyano-5-(methoxymethyl)pyrrolidin-3-yl)oxazole-2-carboxamide and 4-(5-cyano-2-cyclopropoxyphenyl)-N-((3R,5S)-1-cyano-5-(methoxymethyl)pyrrolidin-3-yl)oxazole-2-carboxamide;

or a pharmaceutically acceptable salt thereof.

14. The compound according to claim 1, having the formula (I)(ii):

(I)(ii)

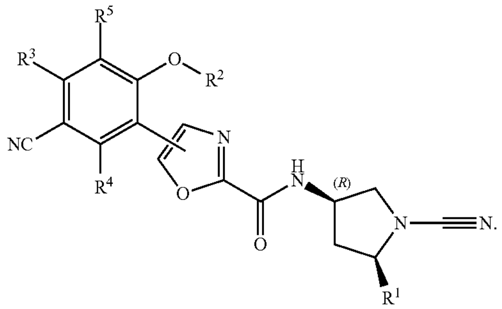

or a tautomer thereof, or a pharmaceutically acceptable salt of said compound or tautomer.

15. The compound according to claim 14, having the formula (IA)(ii):

(IB)(ii)

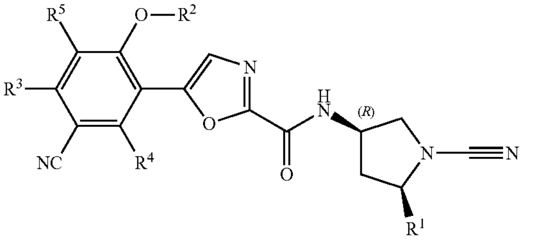

or a tautomer thereof, or a pharmaceutically acceptable salt of said compound or tautomer.

16. The compound according to claim 15, which is selected from:

5-(5-cyano-2-cyclopropoxyphenyl)-N-((3R,5R)-1-cyano-5-(methoxymethyl)pyrrolidin-3-yl)oxazole-2-carboxamide;

5-(5-cyano-2-cyclopropoxyphenyl)-N-((3R,5S)-1-cyano-5-methylpyrrolidin-3-yl)oxazole-2-carboxamide;

5-(5-cyano-2-methoxyphenyl)-N-((3R,5S)-1-cyano-5-methylpyrrolidin-3-yl)oxazole-2-carboxamide;

5-(5-cyano-2-methoxyphenyl)-N-((3R,5R)-1-cyano-5-(methoxymethyl)pyrrolidin-3-yl)oxazole-2-carboxamide;

5-(5-cyano-2-(trifluoromethoxy)phenyl)-N-((3R,5R)-1-cyano-5-(methoxymethyl)pyrrolidin-3-yl)oxazole-2-carboxamide;

5-(5-cyano-2-(trifluoromethoxy)phenyl)-N-((3R,5S)-1-cyano-5-methylpyrrolidin-3-yl)oxazole-2-carboxamide;

5-(5-cyano-4-fluoro-2-methoxyphenyl)-N-((3R,5S)-1-cyano-5-methylpyrrolidin-3-yl)oxazole-2-carboxamide; and 5-(5-cyano-2-cyclopropoxyphenyl)-N-((3R,5R)-1-cyano-5-(fluoromethyl)pyrrolidin-3-yl)oxazole-2-carboxamide;

or a pharmaceutically acceptable salt thereof.

17. The compound according to claim 14, having the formula (IB)(ii):

(IB)(ii)

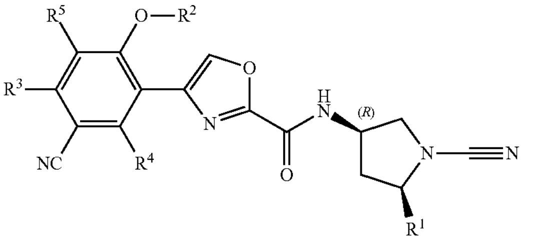

or a tautomer thereof, or a pharmaceutically acceptable salt of said compound or tautomer.

18. The compound according to claim 17, which is selected from:

4-(5-cyano-2-cyclopropoxyphenyl)-N-((3R,5R)-1-cyano-5-(methoxymethyl)pyrrolidin-3-yl)oxazole-2-carboxamide; and 4-(5-cyano-2-methoxyphenyl)-N-((3R,5R)-1-cyano-5-(methoxymethyl)pyrrolidin-3-yl)oxazole-2-carboxamide;

or a pharmaceutically acceptable salt thereof.

19. A pharmaceutical composition, comprising a compound of formula (I) according to claim 1, or a tautomer thereof, or a pharmaceutically acceptable salt of said compound or tautomer, together with one or more pharmaceutically acceptable excipients.

20. A compound, which is selected from formulae (II)(i), (III)(i), (II)(ii) and (III)(ii):

(II)(i)

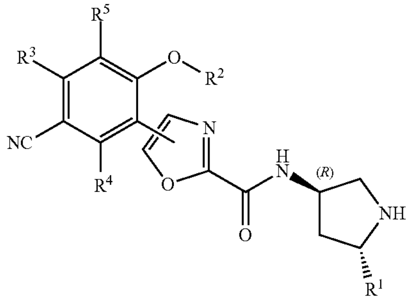

(III)(i)

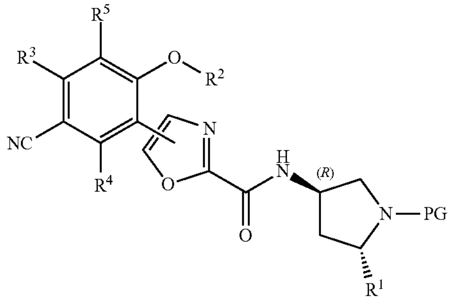

(II)(ii)

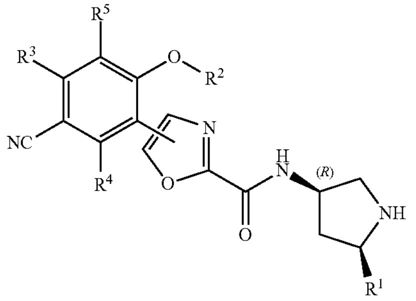

(III)(ii)

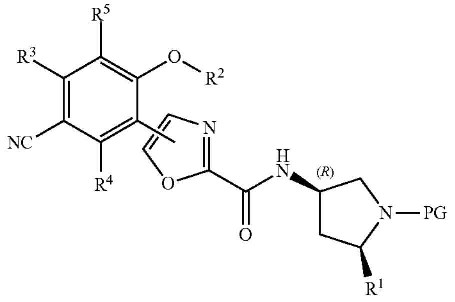

or a tautomer thereof, or a salt of said compound or tautomer;

wherein $R^1$ is selected from $(C_1\text{-}C_4)$alkyl, $(C_1\text{-}C_4)$fluoroalkyl and $CH_2OCH_3$; $R^2$ is selected from $(C_1\text{-}C_4)$alkyl, $CF_3$ and cyclopropyl; and $R^3$, $R^4$ and $R^5$ are each independently selected from hydrogen and halogen; and PG is a protecting group, which is selected from the group consisting of tert-butyloxycarbonyl, benzyloxycarbonyl, p-methoxybenzyl carbonyl, 9-fluorenylmethyloxycarbonyl, acetyl, benzoyl, benzyl, carbamate, p-methoxybenzyl, 3,4-dimethoxybenzyl, p-methoxyphenyl, tosyl, trichloroethoxycarbonyl, 4-nitrobenzenesulfonyl and 2-nitrophenylsulfenyl.

* * * * *